US006287569B1

(12) United States Patent
Kipps et al.

(10) Patent No.: US 6,287,569 B1
(45) Date of Patent: Sep. 11, 2001

(54) VACCINES WITH ENHANCED INTRACELLULAR PROCESSING

(75) Inventors: Thomas J. Kipps, Ranchos Santa Fe; Yunqi Wu, San Diego, both of CA (US)

(73) Assignee: The Regents of the University of California, La Jolla, CA (US)

( * ) Notice: Subject to any disclaimer, the term of this patent is extended or adjusted under 35 U.S.C. 154(b) by 0 days.

(21) Appl. No.: 09/056,105

(22) Filed: Apr. 6, 1998

Related U.S. Application Data

(60) Provisional application No. 60/043,467, filed on Apr. 10, 1997.

(51) Int. Cl.$^7$ .............................. A61K 39/12; C12N 15/00

(52) U.S. Cl. ..................................... 424/199.1; 424/204.1; 435/320.1; 435/235.1; 435/325; 435/343.2; 536/23.4; 536/23.2

(58) Field of Search .............................. 424/199.1, 204.1; 435/320.1, 235.1, 325, 343.2; 536/23.4, 23.2

(56) References Cited

U.S. PATENT DOCUMENTS 5,496,721   3/1996   Bachmair et al. .

FOREIGN PATENT DOCUMENTS

WO 94/17816   8/1994   (WO) .

OTHER PUBLICATIONS

Kipps, Thomas J. et al., "ERB 2NEU DNA Vaccines for Breast Cancer Immunotherapy," Grant No. CA66000 (1998).
McConnell, W. Michael et al., "Molecular Medicine, DNA Vaccines," *The New England Journal of Medicine*, 334(1):42–45 (1996).
Ulmer, Jeffrey B. et al., "Heterologous Protection Against Influenza by Injection of DNA Encoding a Viral Protein," *Science*, 259:1745–1749 (1993).
Watanabe, Akira et al., "Induction of Antibodies to a κ V Region by Gene Immunization," *The Journal of Immunology*, 151:2871–2876 (1993).
Bachmair, Andreas et al., "In Vitro Half–Life of a Protein Is a Function of Its Amino–Terminal Residue," *Science* 234:179–186 (1986).
Gonda, David K. et al., "University and Structure of the N–end Rule," *The Journal of Biological Chemistry*, 264:16700–16712 (1989).
Bachmair, Andreas et al., "The Degradation Signal in a Short–Lived Protein," *Cell*, 56:1019–1032 (1989).
Townsend, Alain et al., "Defective Presentation to Class I–Restricted Cytotoxic T Lymphocytes in Vaccinia–Infected Cells is Overcome by Enhanced Degradation of Antigen," *J. Exp. Med.*, 168:1211–1224 (1988).

Townsend, Alain R. M. et al., "Cytotoxic T Cells Recognize Fragments of the Influenza Nucleoprotein," *Cell*, 42:457–467 (1985).
Germain, Ronald N., "MHC–Dependent Antigen Processing and Peptide Presentation: Providing Ligands for T Lymphocyte Activation," *Cell*, 76:287–299 (1994).
Michalek, Michael T. et al., "A role for the ubiquitin–dependent proteolytic pathway in MHC class I–restricted antigen presentation," *Nature*, 363:552–554 (1993).
Cox, Josephine H. et al., "Presentation of Endogenous and Exogenous Antigens Is Not Affected by Inactivation of $E^1$ Ubiquitin–Activating Enzyme in Temperature–Sensitive Cell Lines," *The Journal of Immunology*, 154:511–519 (1995).
Goth, Samuel et al., "Generation of Naturally Processed Peptide/MHC Class I Complexes Is Independent of theStability of Endogenously Synthesized Precursors," *The Journal of Immunology*, 157:1894–1904 (1996).
de Groot, Raoul J. et al., "Sindbis virus RNA polymerase is degraded by the N–end rule pathway," *Proc. Natl. Acad. Sci. USA*, 88:8967–8971 (1991).
Lévy, Frédéric et al., "Using ubiquitin to follow the metabolic fate of a protein," *Proc. Natl. Acad. Sci. USA*, 93:4907–4912 (1996).
Grant, Ethan P. et al., "Rate of Antigen Degradation by the Ubiquitin–Proteasome Pathway Influences MHC Class I Presentation," *The Journal of Immunology*, 155:3750–3758 (1995).
Michalek, Michael T. et al., "Chemical Denaturation and Modification of Ovalbumin Alters Its Dependence on Ubiquitin Conjugation for Class I Antigen Presentation," *The Journal of Immunology*, 157:617–624 (1996).
Boon, Thierry et al., "Human Tumor Antigens Recognized by T Lymphocytes," *J. Exp. Med.*, 183:725–729 (1996).
Disis, Mary L. et al., "Oncogenic proteins as tumor antigens," *Current Opinion in Immunology*, 8:637–642 (1996).
Robbins, Paul F. et al., "Human tumor antigens recognized by T cells," *Current Opinion in Immunology*, 8:628–636 (1996b).
Wölfel, Thomas et al., "Two tyrosinase nonapeptides recognized on HLA–A2 melanomas by autologous cytolytic T Lymphocytes," *Eur. J. Immunol.*, 24:759–764 (1994).
Kawakami, Yukata et al., "Recognition of Multiple Epitopes in the Human Melanoma Antigen gp100 by Tumor Infiltrating T Lymphocytes Associated with In Vivo Tumor Regression," *J. Immunol.*, 154:3961–3968 (1995).

(List continued on next page.)

*Primary Examiner*—Ali R. Salimi
(74) *Attorney, Agent, or Firm*—Lyon & Lyon LLP

(57) ABSTRACT

Method for generating in a patient a cellular immune response to a target protein or portion thereof comprising the step of introducing into cells of the patient a vector containing a nucleotide sequence encoding a chimeric immunogen comprising a protein processing signal and the target protein or portion thereof, so that the chimeric immunogen is made within the cells and subsequently processed such that the target protein or portion thereof is presented to the patient's immune system so as to generate a cellular immune response.

7 Claims, 7 Drawing Sheets

OTHER PUBLICATIONS

Castelli, Chiara et al., "Mass Spectrometric Identification of a Naturally Processed Melanoma Peptide Recognized by CD8+ Cytotoxic T Lymphocytes," *J. Exp. Med.,* 181:363–368 (1995).

Wölfel, Thomas et al., "A p16$^{INK4a}$–Insensitive CDK4 Mutant Targeted by Cytolytic T Lymphocytes in a Human Melanoma," *Science,* 269:1281–1284 (1995).

Brichard, Vincent G. et al., "A tyrosinase nonapeptide presented by HLA–B44 is recognized on a human melanoma by autologous cytolytic T lymphocytes," *Eur. J. Immunol.,* 26:224–230 (1996).

Topalian, Suzanne L. et al., "Melanoma–specific CD4+ T Cells Recognize Nonmutated HLA–DR–restricted Tyrosinase Epitopes" *J. Exp. Med.,* 183:1965–1971 (1996).

Traversari, Catia et al., "A Nonapeptide Encoded by Human Gene MAGE–1 Is Recognized on HLA–A1 by Cytolytic T Lymphocytes Directed Against Tumor Antigen MZ2–E," *J. Exp. Med.,* 176:1453–1457 (1992).

Potter, Huntington et al., "Enhancer–dependent expression of human κ immunoglobulin genes introduced into mouse pre–B lymphocytes by electroporation," *Proc. Natl. Acad. Sci. USA,* 81:7161–7165 (1984).

Felgner, P. L. et al., "Cationic liposome–mediated transfection," *Nature,* 337:387–388 (1989).

Mannino, Raphael J. et al., "Lipsome Mediated Gene Transfer," *BioTechniques,* 6:682–690 (1988).

Plautz, Gregory E. et al., "Immunotherapy of malignancy by in vivo gene transfer into tumors," *Proc. Natl. Acad. Sci. USA,* 90:4645–4649 (1993).

Wolff, Jon A. et al., "Direct Gene Transfer into Mouse Muscle in Vivo," *Science,* 247:1465–1468 (1990).

Wu, George Y. et al., "Delivery systems for gene therapy," *Biotherapy,* 3:87–95 (1991).

Herweijer, Hans et al., "Direct Gene Transfer In Vivo," *Somatic Gene Therapy,* CRC Press, Inc., pp. 183–202 (1996).

Raz, Eyal et al., "Intradermal gene immunization: The possible role of DNA uptake in the induction of cellular immunity to viruses," *Proc. Natl. Acad. Sci. USA,* 91:9519–9523 (1994).

Waxman, Lloyd et al., "Demonstration of Two Distinct High Molecular Weight Proteases in Rabbit Reticulocytes, One of Which Degrades Ubiquitin Conjugates," *The Journal of Biological Chemistry,* 262:2451–2457 (1987).

Orlowski, Marian, "The Multicatalytic Proteinase Complex, a Major Extralysosomal Proteolytic System," *Biochemistry,* 29:10289–10297 (1990).

Selkoe, D. J. et al., "The Role of APP Processing and Trafficking Pathways in the Formation of Amyloid β–Protein," *Annals New York Academy of Sciences,* 777:57–64 (1996).

King, Randall W. et al., "Mutagenic Analysis of the Destruction Signal of Mitotic Cyclins and Structural Characterization of Ubiquitinated Intermediates," *Molecular Biology of the Cell,* 7:1343–1357 (1996).

King, Randall W. et al., "How Proteolysis Drives the Cell Cycle," *Science,* 274:1652–1659 (1996).

Bohley, Peter, "Surface Hydrophobicity and Intracellular Degradation of Proteins," *Biol. Chem.,* 377:425–435 (1996).

Yaglom, Julia A. et al., "The Molecular Chaperone Ydj1 Is Required for the p34$^{CDC28}$–Dependent Phosphorylation of the Cyclin Cln3 That Signals Its Degradation," *Molecular and Cellular Biology,* 16:3679–3684 (1996).

Yaglom, Julia et al., "p34$^{Cdc28}$–Mediated Control of Cln3 Cyclin Degradation," *Molecular and Cellular Biology,* 15:731–741 (1995).

Ferber, Sarah et al., "Role of arginine–tRNA in protein degradation by the ubiquitin pathway," *Nature,* 326:808–811 (1987).

van der Bruggen, P. et al., "A Gene Encoding an Antigen Recognized by Cytolytic T Lymphocytes on a Human Melanoma," *Science,* 254:1643–1647 (1991).

Gaugler, Béatrice et al., "Human Gene MAGE–3 Codes for an Antigen Recognized on a Melanoma by Autologous Cytolytic T Lymphocytes," *J. Exp. Med.,* 179:921–930 (1994).

Boël, Pascale et al., "BAGE: a New Gene Encoding an Antigen Recognized on Human Melanomas by Cytolytic T Lymphocytes," *Immunity,* 2:167–175 (1995).

Van den Eynde, Benoît et al., "A New Family of Genes Coding for an Antigen Recognized by Autologous Cytolytic T Lymphocytes on a Human Melanoma," *J. Exp. Med.,* 182:689–698 (1995).

Guilloux, Yannik et al., "A Peptide Recognized by Human Cytolytic T Lymphocytes on HLA–A2 Melanomas Is Encoded by an Intron Sequence of the N–Acetylglucosaminyltransferase V Gene," *J. Exp. Med.,* 183:1173–1183 (1996).

Robbins, Paul F. et al., "Cloning of a New Gene Encoding an Antigen Recognized by Melanoma–Specific HLA–A24–Restricted Tumor–Infiltrating Lymphocytes," *The Journal of Immunology,* 154:5944–5950 (1995).

Robbins, Paul F. et al., "A Mutated β–Catenin Gene Encodes a Melanoma–specific Antigen Recognized by Tumor Infiltrating Lymphocytes," *J. Exp. Med.,* 183:1185–1192 (1996).

Coulie, Pierre G. et al., "A mutated intron sequence codes for an antigenic peptide recognized by cytolytic T Lymphocytes on a human melanoma," *Proc. Natl. Acad. Sci. USA,* 92:7976–7980 (1995).

Kawakami, Yutaka et al., "Identification of a human melanoma antigen recognized by tumor infiltrating lymphocytes associated with in vivo tumor rejection," *Proc. Natl. Acad. Sci. USA,* 91:6458–6462 (1994).

Peoples, George E. et al., "Breast and ovarian cancer–specific cytotoxic T lymphocytes recognize the same HER2/neu–derived peptide," *Proc. Natl. Acad. Sci. USA,* 92:432–436 (1995).

Fisk, Bryan et al., "Identification of an Immunodominant Peptide of HER–2/neu Protooncogene Recognized by Ovarian Tumor–specific Cytotoxic T Lymphocyte Lines," *J. Exp. Med.,* 181:2109–2117 (1995).

Ressing, Maaike E. et al., "Occasional Memory Cytotoxic T–Cell Responses of Patients with Human Papillomarivus Type 16–positive Cervical Lesions against a Human Leukocyte Antigen–A *0201–restricted E7–encoded Epitope," *Cancer Research,* 56:582–588 (1996).

Alexander, Margaret et al., "Generation of tumor–specific cytolytic T lymphocytes from peripheral blood of cervical cancer patients by in vitro stimulation with a synthetic human papillomavirus type 16 E7 epitope," *Am. J. Obstet. Gynecol.,* 175:1586–1593 (1996).

Finn, Olivera J. et al., "MUC–1 Epithelial Tumor Mucin–Based Immunity and Cancer Vaccines," *Immunological Reviews,* 145:61–89 (1995).

Bohley, Peter et al., "Post–translational arginylation and intracellular proteolysis," *Biomed. Biochim. Acta.* 50:343–346 (1991).

Sadis, Seth et al., "Synthetic Signals for Ubiquitin–Dependent Proteolysis," *Molecular and Cellular Biology*, 15:4086–4094 (1995).

Ghoda, Lucy et al., "Structural Elements of Ornithine Decarboxylase Required for Intracellular Degradation and Polyamine–Dependent Regulation," *Molecular and Cellular Biology*, 12:2178–2185 (1992).

Li, Xianqiang et al., "Distinct Domains of Antizyme Required for Binding and Proteolysis of Ornithine Decarboxylase," *Molecular and Cellular Biology*, 14:87–92 (1994).

Keiler, Kenneth C. et al., "Role of Peptide Tagging System in Degradation of Proteins Synthesized from Damaged Messenger RNA," *Science*, 271:990–993 (1996).

Rogers, Scott W. et al., "Degradation of Structurally Characterized Proteins Injected into HeLa Cells," *J. Biol. Chem.*, 263:19833–19842 (1988).

Glotzer, Michael et al., "Cyclin is degraded by the ubiquitin pathway," *Nature*, 349:132–138 (1991).

Ordiz, Isabel et al., "Glucose–induced inactivation of isocitrate lyase in *Saccharomyces cerevisiae* is mediated by the cAMP–dependent protein kinase catalytic subunits Tpk1 and Tpk2," *FEBS Letters*, 385:43–46 (1996).

Iizuka, Tomomichi et al., "Intracellular Generation of Amyloid β–Protein from Amyloid β–Protein Precursor Fragment by Direct Cleavage with β– and γ–Secretase," *Biochemical and Biophysical Research Communications*, 218:238–242 (1996).

Wallin, Reidar et al., "Intracellular Proteolytic Processing of the Two–Chain Vitamin K–Dependent Coagulation Factor X," *Thrombosis Research*, 73:395–403 (1994).

Kipps, Thomas J., "Gene Therapy for Cancer," *Journal of Hematotherapy*, 2:367–372 (1993).

Raz, Eyal et al., "Systemic immunological effects of cytokine genes injected into skeletal muscle," *Proc. Natl. Acad. Sci. U.S.A.*, 90:4523–4527 (1993).

Rock, Kenneth L. et al., "Inhibitors of the Proteasome Block the Degradation of Most Cell Proteins and the Generation of Peptides Presented on MHC Class I Molecules," *Cell*, 78:761–771 (1994).

Raper, Steven E. et al., "Safety and Feasibility of Liver–Directed Ex Vivo Gene Therapy for Homozygous Familial Hypercholesterolemia," *Annals of Surgery*, 223:116–126 (1996).

Lu, Li et al., "Stem cells from bone marrow, umbilical cord blood and peripheral blood for clinical application: current status and future application," *Critical Reviews in Oncology/Hematology*, 22:61–78 (1996).

Koc, Omer N. et al., "Transfer of Drug Resistance Genes Into Hematopoietic Progenitors to Improve Chemotherapy Tolerance," *Seminars in Oncology*, 23:46–65 (1996).

Fisher, Lisa J. et al., "Disease, transplantation and regeneration, In vivo and ex vivo gene transfer to the brain," *Current Opinion in Neurobiology*, 4:735–741 (1994).

Goldspiel, Barry R. et al., "Human gene therapy," *Clinical Pharmacology*, 12:488–505 (1993).

Danko, Istvan et al., "Direct gene transfer into muscle," *Vaccine*, 12:1499–1502 (1994).

Davis, Heather L. et al., "Direct Gene Transfer into Skeletal Muscle In Vivo: Factors Affecting Efficiency of Transfer and Stability of Expression," *Human Gene Therapy*, 4:151–159 (1993).

Sugaya, Susumu et al., "Inhibition of Tumor Growth by Direct Intratumoral Gene Transfer of Herpes Simplex Virus Thymidine Kinase Gene with DNA–Liposome Complexes," *Human Gene Therapy*, 7:223–230 (1996).

Prentice, Howard et al., "Ischemic/Reperfused Myocardium Can Express Recombinant Protein Following Direct DNA or Retroviral Injection," *J. Mol. Cell Cardiol.*, 28:133–140 (1996).

Soubrane, C. et al., "Direct Gene Transfer of a Plasmid Carrying the Herpes Simplex Virus–Thymidine Kinase Gene (HSV–TK) in Transplanted Murine Melanoma: In Vivo Study," *European Journal of Cancer*, 32A:691–695 (1996).

Kass–Eisler, Alyson et al., "Prospects for Gene Therapy with Direct Injection of Polynucleotides," *Ann. N. Y. Acad. Sci.*, 772:232–240 (1995).

DeMatteo, Ronald P. et al., "Gene Transfer to the Thymus," *Annals of Surgery*, 222:229–242 (1995).

Addison, Christina L. et al., "Intratumoral injection of an adenovirus expressing interleukin 2 induces regression and immunity in a murine breast cancer model," *Proc. Natl. Acad. Sci. U.S.A.*, 92:8522–8526 (1995).

Hengge, Ulrich R. et al., "Expression of Naked DNA in Human, Pig, and Mouse Skin," *Journal of Clinical Investigation*, 97:2911–2916 (1996).

Felgner, Philip L. et al., "Improved Cationic Lipid Formulations for In Vivo Gene Therapy," *Ann. N. Y. Acad. Sci.*, 772:126–139 (1995).

Furth, Priscilla A. et al., "Gene Transfer into Mammalian Cells by Jet Injection," *Hybridoma*, 14:149–152 (1995).

Vile, R.G. et al., "Targeting of cytokine gene expression to malignant melanoma cells using tissue specific promoter sequences," *Annals of Oncology*, 5 Suppl 4:S59–S65 (1994).

Horton, Robert M., "PCR–mediated Recombination Mutagenesis," *Molecular Biotechnology*, 3:93–99 (1995).

Ali, Stuart Alvaro et al., "PCR–Ligation—PCR Mutagenesis: A Protocol for Creating Gene Fusions and Mutations," *BioTechniques*, 18:746–750 (1995).

Vilardaga, J. P. et al., "Improved PCR Method for High–Efficiency Site–Directed Mutagenesis Using Class 2S Restriction Enzymes," *BioTechniques*, 18:604–606 (1995).

Majumder, Kumud et al., "Background–minimized Cassette Mutagenesis by PCR Using Cassette–specific Selection Markers: A Useful General Approach for Studying Structure–Function Relationships of Multisubstrate Enzymes," *PCR Methods and Applications*, 4:212–218 (1995).

Boles, Eckhard et al., "A rapid and highly efficient method for PCR–based site–directed mutagenesis using only one new primer," *Curr. Genet.*, 28:197–198 (1995).

Vallejo, Abbe N. et al., "In Vitro Synthesis of Novel Genes: Mutagenesis and Recombination by PCR," *PCR Methods and Applications*, 4:S123–S130 (1994).

Henkel, Thomas et al., "Functional Analysis of Mutated cDNA Clones by Direct Use of PCR Products in in Vitro Transcription/Translation Reactions," *Analytical Biochemistry*, 214:351–352 (1993).

Tessier, Daniel C. et al., "PCR–Assisted Large Insertion/Deletion Mutagenesis," *BioTechniques*, 15:498–501 (1993).

Morrison, Hilary G. et al., "A PCR–Based Strategy for Extensive Mutagenesis of a Target DNA Sequence," *BioTechniques*, 14:454–457 (1993).

Cadwell, R. Craig et al., "Randomization of Genes by PCR Mutagenesis," *PCR Methods and Applications*, 2:28–33 (1992).

Stappert, Jörg et al., "A PCR method for introducing mutations into cloned DNA by joining an internal primer to a tagged flanking primer," *Nucleic Acids Research*, 20:624 (1992).

Kunkel, Thomas A., "Rapid and efficient site–specific mutagenesis without phenotypic selection," *Proc. Natl. Acad. Sci. USA*, 82:488–492 (1985).

Kunkel, Thomas A. et al., "Rapid and Efficient Site–Specific Mutagenesis without Phenotypic Selection," *Methods in Enzymology*, 154:367–382 (1987).

Okayama, Hiroto and Paul Berg, "A cDNA Cloning Vector That Permits Expression of cDNA Inserts in Mammalian Cells," *Molecular and Cellular Biology*, 3:280–289 (1983).

Cosman, David et al., "Cloning, Sequence and expression of human interleukin–2 receptor," *Nature*, 312:768–771 (1984).

Berman, Joan W. et al., "Gene transfer in lymphoid cells: Expression of the Thy–1.2 antigen by Thy–1.1 BW5147 lymphoma cells transfected with unfractionated cellular DNA," *Proc. Natl. Acad. Sci. USA*, 81:7176–7179 (1984).

Deans, Robert J. et al., "Expression of an immunoglobulin heavy chain gene transfected into lymphocytes," *Proc. Natl. Acad. Sci. USA*, 81:1292–1296 (1984).

Brody, Steven L. et al., "Adenovirus–mediated in Vivo Gene Transfer," *Ann. N. Y. Acad. Sci.*, 716:90–103 (1994).

Srivastava, Arun, "Parvovirus–Based Vectors for Human Gene Therapy," *Blood Cells*, 20:531–538 (1994).

Jolly, Douglas, "Viral vector systems for gene therapy," *Cancer Gene Therapy*, 1:51–64 (1994).

Russell, S. J., "Replicating Vectors for Gene Therapy of Cancer: Risks, Limitations and Prospects," *European Journal of Cancer*, 30A:1165–1171 (1994).

Yee, Jiing–Kuan et al., "Generation of High–Tier Pseudotyped Retroviral Vectors with Very Broad Host Range," *Methods in Cell Biology*, Chapter 5, 43:99–112 (1994).

Boris–Lawrie, Kathleen A. et al., "Recent advances in retrovirus vector technology," *Current Opinion in Genetics and Development*, 3:102–109 (1993).

Tolstoshev, Paul, "Gene therapy, concepts, current trials and future directions," *Annu. Rev. Pharmacol. Toxicol.*, 33:573–596 (1993).

Carter, Barrie J., "Adeno–associated virus vectors," *Current Opinion in Biotechnology*, 3:533–539 (1992).

Mori, Seijiro et al., "Degradation Process of Ligand–stimulated Platelet–derived Growth Factor β–Receptor Involves Ubiquitin–Proteasome Proteolytic Pathway," *The Journal of Biological Chemistry*, 270:29447–29452 (1995).

Goldberg, Alfred L. et al., "Proteolysis, proteasomes and antigen presentation," *Nature*, 357:375–379 (1992).

Padhy, Lakshmi C. et al., "Identification of a Phosphoprotein Specifically Induced by the Transforming DNA of Rat Neuroblastomas," *Cell*, 28:865–871 (1982).

Schechter, Alan L. et al., "The neu Gene: An erbB–Homologous Gene Distinct from and Unlinked to the Gene encoding the EGF Receptor," *Science*, 229:976–978 (1985).

Slamon, Dennis J. et al., "Human Breast Cancer: Correlation of Relapse and Survival with Amplification of the HER–2/neu Oncogene," *Science*, 235:177–182 (1987).

van de Vijver, Marc J. et al., "Neu–Protein Overexpression in Breast Cancer; Association with Comedo–type Ductal Carcinoma in Situ and Limited Prognostic Value in Stage II Breast Cancer," *The New England Journal of Medicine*, 319:1239–1245 (1988).

Kraus, Matthias H. et al., "Overexpression of the EGF receptor–related proto–oncogene erbB 2 in human mammary tumor cell lines by different molecular mechanisms," *The EMBO Journal*, 6:605–610 (1987).

King, C. Richter et al., "Heterogenous Expression of erbB–2 Messenger RNA in Human Breast Cancer," *Cancer Research*, 49:4185–4191 (1989).

Muller, William J. et al., "Single–Step Induction of Mammary Adenocarcinoma in Transgenic Mice Bearing the Activated c–neu Oncogene," *Cell*, 54:105–115 (1988).

Bouchard, Louise et al., "Stochastic Appearance of Mammary Tumors in Transgenic Mice Carrying the MMTV/c–neu Oncogene," *Cell*, 57:931–936 (1989).

Guy, Chantale T. et al., "Expression of the neu protooncogene in the mammary epithelium transgenic mice induces metastatic disease," *Proc. Natl. Acad. Sci. USA*, 89:10578–10582 (1992).

Fendly, Brian M. et al., "The Extracellular Domain of HER2/neu Is a Potential Immunogen for Active Specific Immunotherapy of Breast Cancer," *Journal of Biological Response Modifiers*, 9:449–455 (1990).

Fendly, Brian M. et al., "Successful Immunization of Rhesus Monkeys with the Extracellular Domain of $p185^{HER2}$: A Potential Approach to Human Breast Cancer," *Vaccine Research*, 2:129–139 (1993).

Abbas, A. K. et al., "Effector Mechanisms of T Cell–Mediated Immune Reactions," *Cellular and Molecular Immunology*, Chapter 13, Philadelphia: W. B. Saunders Co., pp. 261–277 (1994).

Abbas, A. K. et al., "Immunity to Tumors," *Cellular and Molecular Immunology*, Chapter 18, Philadelphia: W. B. Saunders Co., pp. 356–375 (1994).

STRUCTURE OF pcDNA3 Ub-X-lacI-lacZ

SEQUENCE LISTING

<160> NUMBER OF SEQ ID NOS: 35

<210> SEQ ID NO 1
<211> LENGTH: 2130

<210> SEQ ID NO 1
<211> LENGTH: 2130
<212> TYPE: DNA
<213> ORGANISM: Homo sapiens

<400> SEQUENCE: 1

```
cgcggaatcc ggaagaacac aatggatctg gtgctaaaaa gatgccttct tcatttggct      60
gtgataggtg ctttgctggc tgtgggggct acaaaagtac ccagaaacca ggactggctt     120
ggtgtctcaa ggcaactcag aaccaaagcc tggaacaggg agctgtatcc agagtggaca     180
gaagcccaga gacttgactg ctggagaggt ggtcaagtgt ccctcaaggt cagtaatgat     240
gggcctacac tgattggtgc aaatgcctcc ttctctattg ccttgaactt ccctggaagc     300
caaaaggtat tgccagatgg gcaggttatc tgggtcaaca ataccatcat caatgggagc     360
caggtgtggg gaggacagcc agtgtatccc caggaaactg acgatgcctg catcttccct     420
gatggtggac cttgcccatc tggctcttgg tctcagaaga aagctttgt ttatgtctgg     480
aagacctggg gccaatactg gcaagttcta ggggcccag tgtctgggct gagcattggg     540
acaggcaggg caatgctggg cacacacacc atggaagtga ctgtctacca cgccgggga     600
tcccggagct atgtgcctct tgctcattcc agctcagcct tcaccattac tgaccaggtg     660
cctttctccg tgagcgtgtc ccagttgcgg gccttggatg agggaacaa gcacttcctg     720
agaaatcagc tctgaccctt tgccctccag ctccatgacc ccagtggcta tctggctgaa     780
gctgacctct cctacacctg ggactttgga gacagtagtg aaccctgat ctctcgggca     840
cttgtggtca ctcatactta cctggagcct ggcccagtca ctgcccaggt ggtcctgcag     900
gctgccattc ctctcacctc ctgtggctcc tccccagttc caggcaccac agatgggcac     960
aggccaactg cagaggcccc taacaccaca gctggccaag tgcctactac agaagttgtg    1020
ggtactacac ctggtcaggc gccaactgca gagccctctg gaaccacatc tgtgcaggtg    1080
ccaaccactg aagtcataag cactgcacct gtgcagatgc caactgcaga gcacaggt    1140
atgacacctg agaaggtgcc agtttcagag gtcatgggta ccacactggc agagatgtca    1200
actccagagg ctacaggtat gacacctgca gaggtatcaa ttgtggtgct ttctggaacc    1260
acagctgcac aggtaacaac tacagagtgg gtggagacca cagctagaga gctacctatc    1320
cctgagcctg aaggtccaga tgccagctca atcatgtcta cggaaagtat tacaggttcc    1380
ctgggcccc tgctggatgg tacagccacc ttaaggctgg tgaagagaca gtcccctg    1440
gattgtgttc tgtatcgata tggttccttt tccgtcaccc tggacattgt ccagggtatt    1500
gaaagtgccg agatcctgca ggctgtgccg tccggtgagg gggatgcatt tgagctgact    1560
gtgtcctgcc aaggcgggct gcccaaggaa gcctgcatgg agatctcatc gccagggtgc    1620
cagcccctg cccagcggct gtgccagcct gtgctaccca gccagcctg ccagctggtt    1680
ctgcaccaga tactgaaggg tggctcgggg acatactgcc tcaatgtgtc tctggctgat    1740
accaacagcc tggcagtggt cagcacccag cttatcatgc ctggtcaaga agcaggcctt    1800
gggcaggttc cgctgatcgt gggcatcttg ctggtgttga tggctgtggt ccttgcatct    1860
ctgatatata ggcgcagact tatgaagcaa gacttctccg tacccagtt gccacatagc    1920
agcagtcact ggctgcgtct accccgcatc ttctgctctt gtcccattgg tgagaatagc    1980
cccctcctca gtgggcagca ggtctgagta ctctcatatg atgctgtgat tttcctggag    2040
ttgacagaaa cacctatatt tcccccagtc ttccctggga gactactatt aactgaaata    2100
aatactcaga gcctgaaaaa aaaaaaaaaa                                     2130
```

<210> SEQ ID NO 2

<211> LENGTH: 1524
<212> TYPE: DNA
<213> ORGANISM: Homo sapiens

<400> SEQUENCE: 2

```
agcagacaga ggactctcat taaggaaggt gtcctgtgcc ctgaccctac aagatgccaa      60
gagaagatgc tcacttcatc tatggttacc ccaagaaggg gcacgccac tcttacacca     120
cggctgaaga ggccgctggg atcggcatcc tgacagtgat cctgggagtc ttactgctca    180
tcggctgttg gtattgtaga agacgaaatg gatacagagc cttgatggat aaaagtcttc    240
atgttggcac tcaatgtgcc ttaacaagaa gatgcccaca agaagggttt gatcatcggg    300
acagcaaagt gtctcttcaa gagaaaaact gtgaacctgt ggttcccaat gctccacctg    360
cttatgagaa actctctgca gaacagtcac caccaccta ttcaccttaa gagccagcga    420
gacacctgag acatgctgaa attatttctc tcacactttt gcttgaattt aatacagaca    480
tctaatgttc tccttttggaa tggtgtagga aaaatgcaag ccatctctaa taataagtca    540
gtgttaaaat tttagtaggt ccgctagcag tactaatcat gtgaggaaat gatgagaaat    600
attaaattgg gaaaactcca tcaataaatg ttgcaatgca tgatactatc tgtgccagag    660
gtaatgttag taaatccatg gtgttatttt ctgagagaca gaattcaagt gggtattctg    720
ggccatcca atttctcttt acttgaaatt tggctaataa caaactagtc aggttttcga    780
accttgaccg acatgaactg tacacagaat tgttccagta ctatggagtg ctcacaaagg    840
atactttac aggttaagac aaagggttga ctggcctatt tatctgatca agaacatgtc    900
agcaatgtct ctttgtgctc taaaattcta ttatactaca ataatatatt gtaaagatcc    960
tatagctctt tttttttgag atggagtttc gcttttgttg cccaggctgg agtgcaatgg   1020
cgcgatcttg gctcaccata acctccgcct cccaggttca agcaattctc ctgccttagc   1080
ctcctgagta gctgggatta caggcgtgcg ccactatgcc tgactaattt tgtagtttta   1140
gtagagacgg ggtttctcca tgttggtcag gctggtctca aactcctgac ctcaggtgat   1200
ctgcccgcct cagcctccca agtgctggaa ttacaggcg tgagccacca cgcctggctg   1260
gatcctatat cttaggtaag acatataacg cagtctaatt acatttcact tcaaggctca   1320
atgctattct aactaatgac aagtattttc tactaaacca gaaattggta gaaggattta   1380
aataagtaaa agctactatg tactgccta gtgctgatgc ctgtgtactg ccttaaatgt    1440
acctatggca atttagctct cttgggttcc caaatccctc tcacaagaat gtgcagaaga   1500
aatcataaag gatcagagat tctg                                          1524
```

<210> SEQ ID NO 3
<211> LENGTH: 2384
<212> TYPE: DNA
<213> ORGANISM: Homo sapiens

<400> SEQUENCE: 3

```
tattgagttc ttcaaacatt gtagcctctt tatggtctct gagaaataac taccttaaac      60
ccataatctt taatacttcc taaactttct taataagaga agctctattc ctgacactac    120
ctctcatttg caaggtcaaa tcatcattag ttttgtagtc tattaactgg gtttgcttag    180
gtcaggcatt attattacta accttattgt taatattcta accataagaa ttaaactatt    240
aatggtgaat agagtttttc actttaacat aggcctatcc cactggtggg atacgagcca    300
attcgaaaga aaagtcagtc atgtgctttt cagaggatga aagcttaaga taaagactaa    360
aagtgtttga tgctggaggt gggagtggta ttatataggt ctcagccaag acatgtgata    420
```

```
atcactgtag tagtagctgg aaagagaaat ctgtgactcc aattagccag ttcctgcaga      480
ccttgtgagg actagaggaa gaatgctcct ggctgttttg tactgcctgc tgtggagttt      540
ccagacctcc gctggccatt tccctagagc ctgtgtctcc tctaagaacc tgatggagaa      600
ggaatgctgt ccaccgtgga gcggggacag gagtccctgt ggccagcttt caggcagagg      660
ttcctgtcag aatatccttc tgtccaatgc accacttggg cctcaatttc ccttcacagg      720
ggtggatgac cgggagtcgt ggccttccgt cttttataat aggacctgcc agtgctctgg      780
caacttcatg ggattcaact gtggaaactg caagtttggc ttttggggac aaactgcac       840
agagagacga ctcttggtga aagaaacat cttcgatttg agtgcccag agaaggacaa       900
atttttttgcc tacctcactt tagcaaagca taccatcagc tcagactatg tcatccccat    960
agggacctat ggccaaatga aaaatggatc aacacccatg tttaacgaca tcaatattta    1020
tgacctcttt gtctggatgc attattatgt gtcaatggat gcactgcttg ggggatctga    1080
aatctggaga gacattgatt ttgcccatga agcaccagct tttctgcctt ggcatagact    1140
cttcttgttg cggtgggaac aagaaatcca gaagctgaca ggagatgaaa acttcactat    1200
tccatattgg gactggcggg atgcagaaaa gtgtgacatt tgcacagatg agtacatggg    1260
aggtcagcac cccacaaatc ctaacttact cagcccagca tcattcttct cctcttggca    1320
gattgtctgt agccgattgg aggagtacaa cagccatcag tctttatgca atggaacgcc    1380
cgagggacct ttacgcgta atcctggaaa ccatgacaaa tccagaaccc caaggctccc    1440
ctcttcagct gatgtagaat tttgcctgag tttgacccaa tatgaatctg gttccatgga    1500
taaagctgcc aatttcagct ttagaaatac actggaagga tttgctagtc cacttactgg    1560
gatagcggat gcctctcaaa gcagcatgca caatgccttg cacatctata tgaatggaac    1620
aatgtcccag gtacagggat ctgccaacga tcctatcttc cttcttcacc atgcatttgt    1680
tgacagtatt tttgagcagt ggctccgaag gcaccgtcct cttcaagaag tttatccaga    1740
agccaatgca cccattggac ataaccggga atcctacatg gttccttttta taccactgta    1800
cagaaatggt gatttctttta tttcatccaa agatctgggc tatgactata gctatctaca    1860
agattcagac ccagactctt ttcaagacta cattaagtcc tatttggaac aagcgagtcg    1920
gatctggtca tggctccttg gggcggcgat ggtaggggcc gtcctcactg ccctgctggc    1980
agggcttgtg agcttgctgt gtcgtcacaa gagaaagcag cttcctgaag aaaagcagcc    2040
actcctcatg gagaaagagg attaccacag cttgtatcag agccatttat aaaaggctta    2100
ggcaatagag tagggccaaa aagcctgacc tcactctaac tcaaagtaat gtccaggttc    2160
ccagagaata tctgctggta ttttttctgta aagaccattt gcaaaattgt aacctaatac    2220
aaagtgtagc cttcttccaa ctcaggtaga acacacctgt ctttgtcttg ctgttttcac    2280
tcagccctt taacatttc ccctaagccc atatgtctaa ggaaaggatg ctatttggta    2340
atgaggaact gttatttgta tgtgaattaa agtgctctta tttt                     2384
```

<210> SEQ ID NO 4
<211> LENGTH: 2420
<212> TYPE: DNA
<213> ORGANISM: Homo sapiens

<400> SEQUENCE: 4

```
ggatccaggc cctgccagga aaaatataag ggccctgcgt gagaacagag ggggtcatcc      60
actgcatgag agtggggatg tcacagagtc cagcccaccc tcctggtagc actgagaagc     120
```

-continued

```
cagggctgtg cttgcggtct gcaccctgag ggcccgtgga ttcctcttcc tggagctcca    180
ggaaccaggc agtgaggcct tggtctgaga cagtatcctc aggtcacaga gcagaggatg    240
cacaggtgt gccagcagtg aatgtttgcc ctgaatgcac accaagggcc ccacctgcca     300
caggacacat aggactccac agagtctggc ctcacctccc tactgtcagt cctgtagaat    360
cgacctctgc tggccggctg taccctgagt accctctcac ttcctccttc aggttttcag    420
ggacaggcc aacccagagg acaggattcc ctggaggcca cagaggagca ccaaggagaa     480
gatctgtaag taggcctttg ttagagtctc caaggttcag ttctcagctg aggcctctca    540
cacactccct ctctccccag gcctgtgggt cttcattgcc cagctcctgc ccacactcct    600
gcctgctgcc ctgacgagag tcatcatgtc tcttgagcag aggagtctgc actgcaagcc    660
tgaggaagcc cttgaggccc aacaagaggc cctgggcctg gtgtgtgtgc aggctgccac    720
ctcctcctcc tctcctctgg tcctgggcac cctggaggag gtgcccactg ctgggtcaac    780
agatcctccc cagagtcctc agggagcctc cgcctttccc actaccatca acttcactcg    840
acagaggcaa cccagtgagg gttccagcag ccgtgaagag gaggggccaa gcacctcttg    900
tatcctggag tccttgttcc gagcagtaat cactaagaag gtggctgatt tggttggttt    960
tctgctcctc aaatatcgag ccagggagcc agtcacaaag gcagaaatgc tggagagtgt   1020
catcaaaaat tacaagcact gttttcctga gatcttcggc aaagcctctg agtccttgca   1080
gctggtcttt ggcattgacg tgaaggaagc agaccccacc ggccactcct atgtccttgt   1140
cacctgccta ggtctctcct atgatggcct gctgggtgat aatcagatca tgcccaagac   1200
aggcttcctg ataattgtcc tggtcatgat tgcaatggag ggcggccatg ctcctgagga   1260
ggaaatctgg gaggagctga gtgtgatgga ggtgtatgat gggagggagc acagtgccta   1320
tggggagccc aggaagctgc tcacccaaga tttggtgcag gaaaagtacc tggagtaccg   1380
gcaggtgccg gacagtgatc ccgcacgcta tgagttcctg tggggtccaa gggccctcgc   1440
tgaaaccagc tatgtgaaag tccttgagta tgtgatcaag gtcagtgcaa gagttcgctt   1500
tttcttccca tccctgcgtg aagcagcttt gagagaggag gaagagggag tctgagcatg   1560
agttgcagcc aaggccagtg ggagggggac tgggccagtg caccttccag ggccgcgtcc   1620
agcagcttcc cctgcctcgt gtgacatgag gcccattctt cactctgaag agagcggtca   1680
gtgttctcag tagtaggttt ctgttctatt gggtgacttg gagatttatc tttgttctct   1740
tttgaaattg ttcaaatgtt ttttttaag ggatggttga atgaacttca gcatccaagt    1800
ttatgaatga cagcagtcac acagttctgt gtatatagtt taagggtaag agtcttgtgt   1860
tttattcaga ttgggaaatc cattctattt tgtgaattgg gataataaca gcagtggaat   1920
aagtacttag aaatgtgaaa atgagcagt aaaatagatg agataaagaa ctaaagaaat    1980
taagagatag tcaattcttg ccttataccct cagtctattc tgtaaaattt ttaaagatat   2040
atgcatacct ggatttcctt ggcttctttg agaatgtaag agaaattaaa tctgaataaa   2100
gaattcttcc tgttcactgg ctcttttctt ctccatgcac tgagcatctg cttttgtgaa   2160
ggccctgggt tagtagtgga gatgctaagg taagccagac tcatacccac ccataggtc    2220
gtagagtcta ggagctgcag tcacgtaatc gaggtggcaa gatgtcctct aaagatgtag   2280
ggaaaagtga gagaggggtg agggtgtggg gctccgggtg agagtggtgg agtgtcaatg   2340
ccctgagctg gggcatttg ggctttggga aactgcagtt ccttctgggg gagctgattg    2400
taatgatctt gggtggatcc                                                2420
```

-continued

```
<210> SEQ ID NO 5
<211> LENGTH: 4559
<212> TYPE: DNA
<213> ORGANISM: Homo sapiens

<400> SEQUENCE: 5
attccttcat caaacagcca ggagtgagga agaggaccct cctgagtgag gactgaggat      60
ccaccctcac acatagtgg gaccacagaa tccagctcag ccctcttgt cagccctggt      120 acacactggc aatgatctca ccccgagcac acccctcccc caatgccac ttcgggccga      180 ctcagagtca gagacttggt ctgaggggag cagacacaat cggcagagga tggcggtcca      240
ggctcagtct ggcatccaag tcaggacctt gagggatgac caaaggcccc tcccaccccc      300
aactcccccg accccaccag gatctacagc ctcaggatcc ccgtcccaat ccctacccct      360
acaccaacac catcttcatg cttacccccca cccccccatc cagatcccca tccgggcaga      420
atccggttcc acccttgccg tgaacccagg gaagtcacgg gcccggatgt gacgccactg      480
acttgcacat tggaggtcag aggacagcga gattctcgcc ctgagcaacg gcctgacgtc      540
ggcggaggga agcaggcgca ggctccgtga ggaggcaagg taagacgccg agggaggact      600
gaggcgggcc tcaccccaga cagagggccc ccaataatcc agcgctgcct ctgctgccgg      660
gcctggacca ccctgcaggg gaagacttct caggctcagt cgccaccacc tcaccccgcc      720 acccccgcc gctttaaccg cagggaactc tggcgtaaga gctttgtgtg accagggcag      780
ggctggttag aagtgctcag ggcccagact cagccaggaa tcaaggtcag gaccccaaga      840
ggggactgag ggcaacccac ccctaccct cactaccaat cccatccccc aacaccaacc      900 ccaccccat ccctcaaaca ccaacccac ccccaaaccc cattcccatc tcctccccca      960
ccaccatcct ggcagaatcc ggctttgccc ctgcaatcaa cccacggaag ctccgggaat     1020
ggcggccaag cacgcggatc ctgacgttca catgtacggc taaggagggg aagggggttgg     1080 gtctcgtgag tatggccttt gggatgcaga ggaagggccc aggcctcctg aagacagtg      1140 gagtccttag ggacccagc atgccaggac agggggccca ctgtacccct gtctcaaact     1200
gagccacctt ttcattcagc cgagggaatc ctagggatgc agacccactt cagcaggggg     1260
ttggggccca gcctgcgagg agtcaagggg aggaagaaga gggaggactg aggggacctt     1320
ggagtccaga tcagtggcaa ccttgggctg ggggatcctg ggcacagtgg ccgaatgtgc     1380
cccgtgctca ttgcaccttc agggtgacag agagttgagg gctgtggtct gagggctggg     1440
acttcaggtc agcagaggga ggaatcccag gatctgccgg acccaaggtg tgccccttc     1500 atgaggactg gggataccc cggcccagaa agaaggatg ccacagagtc tggaagtccc     1560
ttgttcttag ctctggggga acctgatcag ggatggccct aagtgacaat ctcatttgta     1620
ccacaggcag gaggttgggg aaccctcagg gagataaggt gttggtgtaa agaggagctg     1680
tctgctcatt tcaggggggtt gggggttgag aaagggcagt ccctggcagg agtaaagatg     1740
agtaacccac aggaggccat cataacgttc accctagaac caaagggtc agccctggac     1800 aacgcacgtg ggggtaacag gatgtggccc ctcctcactt gtctttccag atctcaggga     1860
gttgatgacc ttgttttcag aaggtgactc aggtcaacac aggggcccca tctggtcgac     1920
agatgcagtg gttctaggat ctgccaagca tccaggtgga gagcctgagg taggattgag     1980
ggtacccctg ggccagaatg cagcaagggg gccccataga aatctgccct gcccctgcgg     2040
ttacttcaga gaccctgggc agggctgtca gctgaagtcc ctccattatc ctgggatctt     2100
tgatgtcagg gaaggggagg ccttggtctg aaggggctgg agtcaggtca gtagagggag     2160
```

-continued

```
ggtctcaggc cctgccagga gtggacgtga ggaccaagcg gactcgtcac ccaggacacc    2220
tggactccaa tgaatttgga catctctcgt tgtccttcgc gggaggacct ggtcacgtat    2280
ggccagatgt gggtcccctc atatccttct gtaccatatc agggatgtga gttcttgaca    2340
tgagagattc tcaagccagc aaaagggtgg gattaggccc tacaaggaga aaggtgaggg    2400
ccctgagtga gcacagaggg gaccctccac ccaagtagag tggggacctc acggagtctg    2460
gccaaccctg ctgagacttc tgggaatccg tggctgtgct tgcagtctgc acactgaagg    2520
cccgtgcatt cctctcccag gaatcaggag ctccaggaac caggcagtga ggccttggtc    2580
tgagtcagtg tcctcaggtc acagagcaga ggggacgcag acagtgccaa cactgaaggt    2640
ttgcctggaa tgcacaccaa gggccccacc cgcccagaac aaatgggact ccagagggcc    2700
tggcctcacc ctccctattc tcagtcctgc agcctgagca tgtgctggcc ggctgtaccc    2760
tgaggtgccc tcccacttcc tccttcaggt tctgaggggg acaggctgac aagtaggacc    2820
cgaggcactg gaggagcatt gaaggagaag atctgtaagt aagcctttgt cagagcctcc    2880
aaggttcagt tcagttctca cctaaggcct cacacacgct ccttctctcc ccaggcctgt    2940
gggtcttcat tgcccagctc ctgcccgcac tcctgcctgc tgcccctgacc agagtcatca    3000 tgcctcttga gcagaggagt cagcactgca agcctgaaga aggccttgag gcccgaggag    3060
aggccctggg cctggtgggt cgcaggctc ctgctactga ggagcagcag accgcttctt    3120
cctcttctac tctagtggaa gttaccctgg gggaggtgcc tgctgccgac tcaccgagtc    3180
ctccccacag tcctcaggga gcctccagct tctcgactac catcaactac actctttgga    3240
gacaatccga tgagggctcc agcaaccaag aagaggaggg gccaagaatg tttcccgacc    3300
tggagtccga gttccaagca gcaatcagta ggaagatggt tgagttggtt cattttctgc    3360
tcctcaagta tcgagccagg gagccggtca caaaggcaga aatgctggag agtgtcctca    3420
gaaattgcca ggacttcttt cccgtgatct tcagcaaagc ctcgagtac ttgcagctgg    3480 tctttggcat cgaggtggtg gaagtggtcc ccatcagcca cttgtacatc cttgtcacct    3540
gcctgggcct ctcctacgat ggcctgctgg gcgacaatca ggtcatgccc aagacaggcc    3600
tcctgataat cgtcctggcc ataatcgcaa tagagggcga ctgtgcccct gaggagaaaa    3660
tctgggagga gctgagtatg ttggaggtgt ttgaggggag ggaggacagt gtcttcgcac    3720
atcccaggaa gctgctcatg caagatctgg tgcaggaaaa ctacctggag taccggcagg    3780
tgcccggcag tgatcctgca tgctacgagt tcctgtgggg tccaagggcc ctcattgaaa    3840
ccagctatgt gaaagtcctg caccatacac taaagatcgg tggagaacct cacatttcct    3900 acccaccccct gcatgaacgg gctttgagag agggagaaga gtgagtctca gcacatgttg    3960
cagccagggc cagtgggagg gggtctgggc cagtgcacct tccagggccc catccattag    4020
cttccactgc ctcgtgtgat atgaggccca ttcctgcctc tttgaagaga gcagtcagca    4080
ttcttagcag tgagtttctg ttctgttgga tgactttgag atttatcttt ctttcctgtt    4140
ggaattgttc aaatgttcct tttaacaaat ggttggatga acttcagcat ccaagtttat    4200
gaatgacagt agtcacacat agtgctgttt atatagttta ggggtaagag tcctgttttt    4260
tattcagatt gggaaatcca ttccatttg tgagttgtca cataataaca gcagtggaat    4320
atgtatttgc ctatattgtg aacgaattag cagtaaaata catgatacaa ggaactcaaa    4380
agatagttaa ttcttgcctt atacctcagt ctattatgta aaattaaaaa tatgtgtatg    4440
tttttgcttc tttgagaatg caaaagaaat taaatctgaa taaattcttc ctgttcactg    4500
gctcatttct ttaccattca ctcagcatct gctctgtgga aggccctggt agtagtggg    4559
```

<210> SEQ ID NO 6
<211> LENGTH: 4204
<212> TYPE: DNA
<213> ORGANISM: Homo sapiens

<400> SEQUENCE: 6

| | | | | | |
|---|---|---|---|---|---|
| acgcaggcag | tgatgtcacc | cagaccacac | cccttccccc | aatgccactt | cagggggtac | 60 |
| tcagagtcag | agacttggtc | tgagggagc | agaagcaatc | tgcagaggat | ggcggtccag | 120 |
| gctcagccag | gcatcaactt | caggaccctg | agggatgacc | gaaggccccg | cccacccacc | 180 |
| cccaactccc | ccgaccccac | caggatctac | agcctcagga | cccccgtccc | aatccttacc | 240 |
| ccttgcccca | tcaccatctt | catgcttacc | tccaccccca | tccgatcccc | atccaggcag | 300 |
| aatccagttc | caccccctgcc | cggaacccag | ggtagtaccg | ttgccaggat | gtgacgccac | 360 |
| tgacttgcgc | attggaggtc | agaagaccgc | gagattctcg | ccctgagcaa | cgagcgacgg | 420 |
| cctgacgtcg | gcggagggaa | gccggcccag | gctcggtgag | gaggcaaggt | aagacgctga | 480 |
| gggaggactg | aggcgggcct | cacctcagac | agagggcctc | aaataatcca | gtgctgcctc | 540 |
| tgctgccggg | cctgggccac | cccgcagggg | aagacttcca | ggctgggtcg | ccactacctc | 600 |
| accccgccga | ccccgccgc | tttagccacg | ggaactctg | gggacagagc | ttaatgtggc | 660 |
| cagggcaggg | ctggttagaa | gaggtcaggg | cccacgctgt | ggcaggaatc | aaggtcagga | 720 |
| ccccgagagg | gaactgaggg | cagcctaacc | accaccctca | ccaccattcc | cgtcccccaa | 780 |
| cacccaaccc | caccccatc | ccccattccc | atccccaccc | ccaccccctat | cctggcagaa | 840 |
| tccgggctt | gccctggta | tcaagtcacg | gaagctccgg | gaatggcggc | caggcacgtg | 900 |
| agtcctgagg | ttcacatcta | cggctaaggg | agggaagggg | ttcggtatcg | cgagtatggc | 960 |
| cgttgggagg | cagcgaaagg | gcccaggcct | cctggaagac | agtggagtcc | tgaggggacc | 1020 |
| cagcatgcca | ggacagggg | cccactgtac | ccctgtctca | aaccgaggca | ccttttcatt | 1080 |
| cggctacggg | aatcctaggg | atgcagaccc | acttcagcag | ggggttgggg | cccagccctg | 1140 |
| cgaggagtca | tggggaggaa | gaagagggag | gactgagggg | accttggagt | ccagatcagt | 1200 |
| ggcaaccttg | gctggggga | tgctgggcac | agtggccaaa | tgtgctctgt | gctcattgcg | 1260 |
| ccttcagggt | gaccagagag | ttgagggctg | tggtctgaag | agtgggactt | caggtcagca | 1320 |
| gagggaggaa | tcccaggatc | tgcagggcc | aaggtgtacc | cccaaggggc | ccctatgtgg | 1380 |
| tggacagatg | cagtggtcct | aggatctgcc | aagcatccag | gtgaagagac | tgagggagga | 1440 |
| ttgagggtac | ccctgggaca | gaatgcggac | tgggggcccc | ataaaaatct | gccctgctcc | 1500 |
| tgctgttacc | tcagagagcc | tggcagggc | tgtcagctga | ggtccctcca | ttatcctagg | 1560 |
| atcactgatg | tcagggaagg | ggaagccttg | gtctgagggg | gctgcactca | gggcagtaga | 1620 |
| gggaggctct | cagaccctac | taggagtgga | ggtgaggacc | aagcagtctc | ctcacccagg | 1680 |
| gtacatggac | ttcaataaat | ttggacatct | ctcgttgtcc | tttccgggag | gacctgggaa | 1740 |
| tgtatggcca | gatgtgggtc | ccctcatgtt | tttctgtacc | atatcaggta | tgtgagttct | 1800 |
| tgacatgaga | gattctcagg | ccagcagaag | ggagggatta | ggccctataa | ggagaaaggt | 1860 |
| gagggccctg | agtgagcaca | gaggggatcc | tccaccccag | tagagtgggg | acctcacaga | 1920 |
| gtctggccaa | ccctcctgac | agttctggga | atccgtggct | gcgtttgctg | tctgcacatt | 1980 |
| gggggcccgt | ggattcctct | cccaggaatc | aggagctcca | ggaacaaggc | agtgaggact | 2040 |
| tggtctgagg | cagtgtcctc | aggtcacaga | gtagagggg | ctcagatagt | gccaacggtg | 2100 |

-continued

```
aaggtttgcc ttggattcaa accaagggcc ccacctgccc cagaacacat ggactccaga    2160
gcgcctggcc tcaccctcaa tactttcagt cctgcagcct cagcatgcgc tggccggatg    2220
taccctgagg tgccctctca cttcctcctt caggttctga ggggacaggc tgacctggag    2280
gaccagaggc ccccggagga gcactgaagg agaagatctg taagtaagcc tttgttagag    2340
cctccaaggt tccattcagt actcagctga ggtctctcac atgctccctc tctcccagg     2400 ccagtgggtc tccattgccc agctcctgcc cacactcccg cctgttgccc tgaccagagt    2460
catcatgcct cttgagcaga ggagtcagca ctgcaagcct gaagaaggcc ttgaggcccg    2520
aggagaggcc ctgggcctgg tgggtgcgca ggctcctgct actgaggagc aggaggctgc    2580
ctcctcctct tctactctag ttgaagtcac cctgggggag gtgcctgctg ccgagtcacc    2640
agatcctccc cagagtcctc agggagcctc cagcctcccc actaccatga actaccctct    2700
ctggagccaa tcctatgagg actccagcaa ccaagaagag gaggggccaa gcaccttccc    2760
tgacctggag tccgagttcc aagcagcact cagtaggaag gtggccgagt tggttcattt    2820
tctgctcctc aagtatcgag ccaggggagcc ggtcacaaag gcagaaatgc tggggagtgt    2880
cgtcggaaat tggcagtatt tctttcctgt gatcttcagc aaagcttcca gttccttgca    2940
gctggtcttt ggcatcgagc tgatggaagt ggaccccatc ggccacttgt acatctttgc    3000
cacctgcctg ggcctctcct acgatggcct gctgggtgac aatcagatca tgcccaaggc    3060
aggcctcctg ataatcgtcc tggccataat cgcaagagag ggcgactgtg ccctgagga    3120 gaaaatctgg gaggagctga gtgtgttaga ggtgtttgag gggagggaag acagtatctt    3180
gggggatccc aagaagctgc tcacccaaca tttcgtgcag gaaaactacc tggagtaccg    3240
gcaggtcccc ggcagtgatc ctgcatgtta tgaattcctg tggggtccaa gggccctcgt    3300
tgaaaccagc tatgtgaaag tcctgcacca tatggtaaag atcagtggag gacctcacat    3360
ttcctaccca cccctgcatg agtgggtttt gagagagggg gaagagtgag tctgagcacg    3420
agttgcagcc agggccagtg ggagggggtc tgggccagtg caccttccgg ggccgcatcc    3480 cttagttttcc actgcctcct gtgacgtgag gcccattctt cactctttga agcgagcagt    3540
cagcattctt agtagtgggt ttctgttctg ttggatgact ttgagattat tctttgtttc    3600
ctgttggagt tgttcaaatg ttccttttaa cggatggttg aatgagcgtc agcatccagg    3660
tttatgaatg acagtagtca cacatagtgc tgtttatata gtttaggagt aagagtcttg    3720 tttttttactc aaattgggaa atccattcca ttttgtgaat tgtgacataa taatagcagt    3780
ggtaaaagta tttgcttaaa attgtgagcg aattagcaat aacatacatg agataactca    3840
agaaatcaaa agatagttga ttcttgcctt gtacctcaat ctattctgta aaattaaaca    3900
aatatgcaaa ccaggatttc cttgacttct ttgagaatgc aagcgaaatt aaatctgaat    3960
aaataattct tcctcttcac tggctcgttt cttttccgtt cactcagcat ctgctctgtg    4020
ggaggccctg ggttagtagt ggggatgcta aggtaagcca gactcacgcc tacccatagg    4080
gctgtagagc ctaggacctg cagtcatata attaaggtgg tgagaagtcc tgtaagatgt    4140
agaggaaatg taagagaggg gtgagggtgt ggcgctccgg gtgagagtag tggagtgtca    4200
gtgc                                                                4204
```

<210> SEQ ID NO 7
<211> LENGTH: 945
<212> TYPE: DNA
<213> ORGANISM: Homo sapiens

<400> SEQUENCE: 7

-continued

```
atgcctcttg agcagaggag tcagcactgc aagcctgaag aaggccttga ggcccgagga      60
gaggccctgg gctggtgggt gcgcaggct cctgctactg aggagcagga ggctgcctcc     120
tcctcttcta ctctagttga agtcaccctg ggggaggtgc ctgctgccga gtcaccagat    180
cctccccaga gtcctcaggg agcctccagc ctccccacta ccatgaacta ccctctctgg    240
agccaatcct atgaggactc cagcaaccaa gaagaggagg ggccaagcac cttccctgac    300
ctggagtctg agttccaagc agcactcagt aggaaggtgg ccaagttggt tcattttctg    360
ctcctcaagt atcgagccag ggagccggtc acaaaggcag aaatgctggg gagtgtcgtc    420
ggaaattggc agtacttctt tcctgtgatc ttcagcaaag cttccgattc cttgcagctg    480
gtctttggca tcgagctgat ggaagtggac cccatcggcc acgtgtacat ctttgccacc    540
tgcctgggcc tctcctacga tggcctgctg ggtgacaatc agatcatgcc aagacaggc    600 ttcctgataa tcatcctggc cataatcgca aagagggcg actgtgcccc tgaggagaaa    660
atctgggagg agctgagtgt gttagaggtg tttgagggga gggaagacag tatcttcggg    720
gatcccaaga agctgctcac ccaatatttc gtgcaggaaa actacctgga gtaccggcag    780
gtccccggca gtgatcctgc atgctatgag ttcctgtggg gtccaagggc cctcattgaa    840
accagctatg tgaaagtcct gcaccatatg gtaaagatca gtggaggacc tcgcatttcc    900
tacccactcc tgcatgagtg ggctttgaga gaggggggaag agtga                  945
```

<210> SEQ ID NO 8
<211> LENGTH: 1022
<212> TYPE: DNA
<213> ORGANISM: Homo sapiens

<400> SEQUENCE: 8

```
gcctgtgggt ctccattgcc cagcttttgc ctgcactctt gcctgctgcc ctgaccagag     60
tcatcatgtc tcttgagcag aagagtcagc actgcaagcc tgaggaaggc gttgaggccc    120
aagaagaggc cctgggcctg gtgggtgcac aggctcctac tactgaggag caggaggctg    180
ctgtctcctc ctcctctcct ctggtcctgg gcaccctgga gaaagtgcct gctgctgagt    240
cagcagatcc tccccagagt cctcaggag cctctgcctt acccactacc atcagcttca    300
cttgctggag gcaacccaat gagggttcca gcagccaaga agaggaggag gccagcacct    360
cgcctgacgc agagtccttg ttccgagaag cactcagtaa caaggtggat gagttggctc    420
attttctgct ccgcaagtat cgagccaagg agctggtcac aaaggcagaa atgctggaga    480
gagtcatcaa aaattacaag cgctgctttc ctgtgatctt cggcaaagcc tccgagtccc    540
tgaagatgat ctttggcatt gacgtgaagg aagtggaccc cgccagcaac acctacaccc    600
ttgtcacctg cctgggcctt tcctatgatg gcctgctggg taataatcag atctttccca    660
agacaggcct cctgataatc gtcctgggca caattgcaat ggagggcgac agcgcctctg    720
aggaggaaat ctgggaggag ctgggtgtga tgggggtgta tgatgggagg gagcacactg    780
tctatgggga gccaggaaa ctgctcaccc aagattgggt gcaggaaaac tacctggagt    840
accggcaggt accggcagt aatcctgcgc gctatgagtt cctgtggggt ccaagggctc    900
tggctgaaac cagctatgtg aaagtcctgg agcatgtggt cagggtcaat gcaagagttc    960
gcattgccta cccatccctg cgtgaagcag ctttgttaga ggaggaagag ggagtctgag   1020
ca                                                                   1022
```

<210> SEQ ID NO 9

<211> LENGTH: 11495
<212> TYPE: DNA
<213> ORGANISM: Homo sapiens

<400> SEQUENCE: 9

```
cagctgggca aatgctcaga ggtgagagaa aaagagcatc tccaacccat cacttcaaca    60
aagagccagg acccaggaag aggaccctcc tgagtgaaga ctgagggtaa accccgctc    120
aaagagggc cacagaatcc agcttagtcc ctcctgtcag ccctggaaga ccccagcggc    180
tttgtcgccc aaggacacct ctccccccac tgtgacctca ggggactagg agtcagaacc    240
ttggtctgag gggagcagac accatccgca gagaacaggg gtccaggcta tgccaggaat    300
caaaggactg aggggcacgc ctacctcaac ccctaaccccc aggacctctt gcctcctccc    360
ccacccaac tccaccctg gccgaatccg gttccacccc tgctgtcaac ccaggtggcc    420
cggatgtgac atccctgact tgcgcattgg tctgaccagc aactcgagat ccacggaggg    480
aagcaggcgc aggctctgtg aggaggcaag gtgggggcag gctgtgccag gcgtgaaagt    540
caggaccccta agagagagct gagggttccc caccccatt cctatccccc acccccattcc    600
cattccttc cacactccta acccaatcca caccctcatc cctaccagc accccatcct    660
ccccaacccc gtgccaccct catacccca tccccaattc aaccccgca ccctcatccc    720
ccaccccaca cctgcaccccc cacccccaa acccatacc cccatccagg caggatcccc    780
ggttccgccc ccgctttcaa ccaaggaaag ccccagctgc ccggatgtga tgccactgac    840
ttgcgcactg ggggttagag acaagcgagc ttctgcgtct gactcgcagc ttgagactgg    900
cggagggaag cccgcccagg ctctataagg agacaaggtg agatgctgag gaggactca    960
ggaggacccc cacccacat agacgaccac aaaaaaatcca acaccacccc tgctgccagc   1020
cctgggccac tcctggagac ttctcagtct gtggtggggg ggccaccacc ccactgccac   1080
ttaagcctca gggggattctg aagtcagagc ttggggtgat cagtgcaaga ctggtggggg   1140
cgggctctgc caggcatcaa cctcaggacc ctaaaagcca gctgagcgta ccacaccgct   1200
attcccatcc cgcaaccccca ttcccatccc ctaacccctt cccattccca ttcgcactca   1260
caaacccatc tacactccca tcctccacca gctccccatc ctcccaaaca ccccaccacc   1320
ttcataccgc catctcccac ccccaaaaac cgcccccctc caccgacctc acccctccca   1380
ccccatcca cgctgaatcg ggttgcgctc cctctttcaa cccaagaaag ccccaggggc   1440
ccggatgtga tgccactgac ttgcgcattg ggggttagag agaagcgagc tgctctgtct   1500
gaccagcagc ttgggattgg cggagggaag cgggccaggc cctgtgagga gtcaaggtga   1560
gacgctgagg gaggactcag gaggccccca ccccagatag atgaccccaa ataatcccgc   1620
accactcctg ctaccagccg tgggccaacc cgtgggcgga cttctgagtc tggggcggcc   1680
caccacccca ctgcctctga agttgcaggg gactctggag tcagagcttg ggttgattag   1740
tgtaagacta gtgagggcag gctctgccag gcatggacct cagcaccta agagagggct   1800
aagcgtaccc caccctatt ccatccccc accacgtccc ctttccgatt accatttgca   1860
ctcccaaacc atccacgccc ccatccccca ccagcactcc tctcctcttc aaccccccac   1920
ctctctcata ccgccatctc ccaccccaac aacccgggcc cttctaccaa cctcacccct   1980
cccacccca tccacactga atcacgttcc gcttccgctt tcaacccacc cccaaaaacc   2040
cgccccctcc atcgacctca ccctcccac cccatccac gctgaatctg atttccgctt   2100
cctctttcaa cccaagaaag ccccaggggc ccggatgtga tgccactgac ttgcgcattg   2160
ggggttagag agaagcgagc tgctctgtct gaccagcagc ttgggattgg cggagggaag   2220
```

```
cgggccaggc cctgtgagga gtcaaggtga gacgctgagg gaggactcag gaggccccca    2280
ccccagatag acgaccccaa ataatcccgc accactcctg ctaccagccg tgggccaccc    2340
gtgggcggac ttctgagtct ggggcgccct ccacccccact gcgtctgaag tcgcatggga   2400
ctctggagtc cgagcttggg gtggttagtg taagactagt gagggcaggc tctacgaggc    2460
atcaacctca ggaccctaag agagggccaa gtgtacccca cccctatttc tatccccac    2520 cgcctcccct ttcccattac tatttgcact cccaaaccca tccgcgcccc tatccccac    2580 cagcactcct atcctcaacc ccgcacctct ctcacaccgc catctcccac cccaaaaact    2640
ggggcccctc caccaacctc acccctccca ccccatgga tgctgaattg ggttgcgctt    2700
ccgctttcaa cccaccccca aaacccgccc cctccaccg acctcacccc tcccaccccc    2760
ttccacgctg aatcgggttt ccgcttccgc tttcaaccca gaaagtccc aggtgcccgg    2820 atgtgatgcc actgacttgc gcattggggg ttagagagaa gcgagctgct ctgaccagcc    2880
gcttgggatt ggcggaggga agcgggccag gccctgtgag gagtcaaggt gagatgctga    2940
gggaggactc aggaggcccc caccccagat agacgacccc aaataatccc gcaccactcc    3000
tgctaccagc cgtgggccac ctgtgggcgg acttctgagt ctggggcgcc caccacccca    3060
ctgcctctga gtcgcagag gactctggag tcagagctta gggtgtttag tgtaagacta    3120
gtgaggccag gctctgccag gcatcaatct caggaccgta agagagggct aagcgtaccc    3180 caccccatt cccatccccc atcacgtccc ctttcccatt accatttgca ctcctaaacc    3240
catccgcgcc cccatccccc accagcactc ctcctcgacc cccacctct gtcataccgc    3300 catctgccac cccaaaaacc ggggcccctc caccaacctc accctccca ccccatcca    3360 cgctgaatcg ggttccgctt ccgctttcaa cccactccca aaacccgcc cctccaccg    3420 acctcccccc caccccatc cacgctgaat cgtgtttccg cttccgcttt caacccaaga    3480
aagcctcagg ggcccggatg tgatgccact gacttgcgca ttgggggtta gagagaagcg    3540
agctgctgtc tgaccagcag cttgggattg gtggaaggaa gcaggccagg ccctgtgagg    3600
agtcaaggtg agacgctgag gaggactcag gaggccacca ccccagatag aagacccaa    3660 ataatcccgc accactccta ccagccgtgg gccacctgtg gcggacttc tgagcttggg    3720 gcgcccacca cccccactgcc tctgaagtcg caggggactc tggagtcaga gcttggggtg    3780
tttagtgtaa gactagtgag gccaggctct gccgggcatc aatctcagga ccctaagaga    3840
gggctaagcg tacccccaccc ctattcccat ccccaccac gtcccctttc ccattaccat    3900
ttgcactcct aaaccatcc ccgcccccat ccccaccag cactcctcct cgacccccca    3960
cctctgtcat accgccatct gccacccaa aaaccgggggc cctccacca acctcaccc    4020 tcccacccccc atccacgctg aatcgggttc cgcttccgct ttcaacccac tcccaaaaac    4080 ccgcccccctc caccgacctc cccccacccc catccacgtg aatcgtgt ttccgcttcc    4140 gctttcaacc caagaaagcc tcaggggccc ggatgtgatg ccactgactt gcgcattggg    4200
ggttagagag aagcgagctg ctgtctgacc agcagcttgg gattggtgga aggaagcagg    4260
ccaggccctg tgaggagtca aggtgagacg ctgaggagga ctcaggaggc caccaccca    4320 gatagacgac cccaaataat cctgcaccac tcctacctgc cgtgggccac ctgtgggcgg    4380
acttctgagc ttggggcgcc caccaccca ctgcctctga gtcgcaggg gactctggag    4440 tcagagcttg gggtgtttag tgtaagacta gtgaggccag gctctgccgg gcatcaatct    4500
caggacccta agagagggct aagcgtaccc caccccctatt cccatccccc accacgtccc    4560
```

-continued

```
ctttcccatt accatttgca ctcccaaacc atccacgccc catcccccac cagcactcct    4620
ctcctcttca acccccacc tctctcatat cgccatctcc caccccaaca acccgggccc    4680
ttgtaccaac ctcacccctc ccaccccat ccacactgaa tcacgttccg cttccgcttt    4740
caacccaccc ccaaaaaccc gcccctcca ccgacctcac ccttcccacc ccatccacg     4800
ctgaatctga tttctggttt ctctttcaac caagaaagc cccaggggcc cggatgtgat    4860
gccactgact tgcgcattcg ggttagaga aagcgagct gctctgtgac cagccgcttg     4920
ggattggtgg agggaagcgg gccaggccct gtgaggagtc aaggtgagac gctgagggag   4980
gactcaggag gcccccaccc cagatagacg accccaaata atcccgcacc actcctgcta   5040
ccagccgtgg gccacccgtg ggctgacttc tgagtctggg gcgccctcca ccccactgcg   5100
tctgaagtca catgggactc tggagtccga gcttggggtg gttagtgtaa gactagtgag   5160
ggcaggctct acgaggcatc aacctcagga ccctaagaga gggctaagcg taccccaccc   5220
ccattcccat cccccacccc ctccccttc ccattactat ttgcactccc aaacccatcc    5280
gcgcccccat cccccaccag gctcctatcc tcctcaaccc cgcacctctc tcacaccacc   5340
atctcccacc ccaaaacccg ggcccctcca ccaacctcac ctctcccacc ccatccaca    5400
ctgaatcagg ttctgcttcc gctttcaacc caccccaaa acgcgccccc tccaccgacc    5460
tcactcctcc caccccatc cacgctgaat cgggttctgc ttccgctttc aacccaagaa    5520
agccgcaggt gccggaatgt gatgccactg acttgcgcat tgggggttag agaaaagcga   5580
gctgctctgt ctgaccagca gcttgggact ggtggaggga gcgggccag gccctgtgag    5640
gagtcaaggt gagacgctga gggaggactc aggaggcccc caccgcagat agacaatccc   5700
aaataatccc gaaccactca tgctcccagc cctgggccac tcgtgggggg acttctgagt   5760
ctggggcgcc caccacccca ctgcctctga agtcgcacgg gactctgcag tcagagcttg   5820
gggtgatcag tgcaagactg gtgagggcag gctctgccag gcatcaacct caggactgta   5880
agagagggcc gagggtcccc caccccatt cccatccccc ttcccattcc catccacact    5940
cccaacccca tctacacccct atccccacc agcaccccta tcctcccaa acccccacta    6000
cccttatgtc ctcatccccc accccaacac cactatcccc atccaggttg aatcgcattc   6060
cgtttctgct ttcaacccag ggaagctcca ggttcctgga tgtgatgcca gtgacttgtg   6120
cattggggt tagagagacg ctagcttctc agtctgacag gcagcttggg attggcagag    6180
ggaagccggt ccaggctctg tgaggtggca tagtgagaag ctgagggaga agtcgggagg   6240
ccctctccac cccagataga cgaccccaaa taatccggca cccctcctgc ttccagtcct   6300
gggccacccg tgggcggact tctgagtctg gacgcccac caccccactg ccgctgaagc    6360
cgcagggact atggagtcag agcttggtgt gatcagtgca ggactggtgg gggtaggctc   6420
tgccaggcat caacgtcagg accctaggag agggctgagt gtcccccacc cccattccta   6480
tccctaccc ctttcccatc tgcactccct accccatctg taccccatt ccccacctgt     6540
gcccctatcc tccccaaccc cccaaccagc ctcatacccc cctcccccac ccctaccttc   6600
atccccatca gtgcagcatc cggttccacc cctgctttca atccaggcaa gccctgggtg   6660
gccggatgtg atgccactga cttgtgaatt gagggttaga gagaagtgag tttctgggtc   6720
tgaagggtgg cttgagatcg gcagagggaa ggtggcccag gctttgtgaa gaggcaaagt   6780
gagactctga gggaggattc aggaaacccc tatccctgat agaggtccc agccctggac    6840
taccccgcgg aggctgactt tcagactggg gctgctcccc acctccgccc ccttcgcaac   6900
gcgtttgttt aagccacagg ggactctgga gtcagaggtt ggtgtgatca gggaagggct   6960
```

```
ggttaggaga ggcatggccc aggccctgcc aggaatcaaa gtcagaaacc tgagagggaa   7020
ctgaggtccc ccaagatcct agtctaaccc ccactccac  aaatccgctg ccatttcgct   7080
gctccatttc ccattccttg ccctccaccc tcaccaggca gaatccagtt cccttctgc    7140 tatcaatcca gggaaacccc aggcttggtg ctgggatgtt ttttgggggt cagagaatca   7200
agggcatagt cctgagggc  cagttgagat cggctgaggg gagcgggccc aagctctgtg   7260
gcgaggcaag gtgagactct gaggaaggac tgaggaggcc cccacccaag atagaggaac   7320
ccaaataatc cagcgcagct cctgctgcca gtcctggacc acccggggga agacttctca   7380
ggctaggcca tcccagctcc cactgccact aaagctacag gggactctag agtcaagagc   7440
ttggtgtgcc caaggcaggg cccaggctct gcctggcatc ggggtcagga ccttgagagg   7500
gaactgaggg cgctacaccc ccaccccatc cgcattccaa catgcccagc cccatcccca   7560
actccgtttt gcagaatcca tttttcccc  tgcagtcaac cccgggaaga cctgggaatg   7620
gtcaggcact cggatcttga catccacatc gagggctgaa ggagggagag ggtttggtat   7680
catgagcaga gcctcagggt agcagaggga ggaccctggc cctcctggga gatgaggaag   7740
gcctcaggag acccagcacc ccaaggcagg gagcccaccc caccctgtc  tgagaatgag   7800 gtgcctcctc ttttagcctc aggaatccaa gggatggcaa ctcaggtcag cagagggtg    7860 ggttccaagc ccttccagga tcaaggaaag gaagacgagg gaggattcag ggggccttgc    7920
attccagatc agtggagacc tgggccctgg gaggtcctgg gcaaggtagc cacctgtagc   7980
tcatacttcc tgcatcttcg aggtcacaga gaggagaggg ctatggtctg aggggtggta   8040
cttcaggtcc gcagagggag gagtcccagg atctacagga cccaaggtgt gccacacttc   8100
acgaggaatg gggatacctg tggctcagaa agacgggacc ccacagagtc tggctgtccc   8160
ctgttcttag ctcaggggg  accagaggag ggatggccct atgtgccaat ttcacttgtt   8220
ccacaggcag gaagttgggg aaccttcagg gagatgaggt tttggagtaa aggggcaatg   8280
tttgctcatc tcagggggtt gggggttgag gaagggcagg ccctgtcagg agcaaacatg   8340
agtacccaca ggaggccatc agaaccctca ccccagaacc aaaggggtca gccctgggca   8400
ccccacacag gggtgacagg atgtggctcc ttctcatttc tgattccaga tctcagtgag   8460
gtgaggacct tgttctcaga gggtgactca ggtcaccaca gggaccccca tctggtctac   8520
agacacagtg gtcccaggat ctgccaagag tcctggtgag gaatgtgagg gaggattgag   8580
ggtaccacag ggccagaacg cagatgatga ccccacagaa atcagccctg ctcctgttgt   8640
caccccagag agcatgggct tggctttctg ctgaggtccc tctcttatcc tgggatcact   8700
ggtgtcacgg agtgggaggc cttggtctga gggggctgca cccaggtcag tagagggagg   8760
gtcccaggct ctgccaggag ttgaggtgag gaccaagcag gctccgcatc caggacacat   8820
gggttccaat gaatttcgac atcttttgct gtcgttcttc ggaagaccta ggcacaggtg   8880
gccagatgtg gggtttctta ggtcctgttc cctctcaggc atgtgagctc ttgatctgag   8940
tttctcaggc cagcaaaaga gtgggatcca ggccctgcct ggagaaatgt gagggccctg   9000
agtgaacaca gtggggatca tccactccat gagagtgggg acctcacaga gtccagccta   9060
ccctcttgat ggcactgagg gaccgggct  gtgcttacag tctgcaccct aagggcccat   9120
ggattcctct cctaggagct ccaggaacaa ggcagtgagg ccttggtctg agacagtgtc   9180
ctcaggttac agagcagagg atgcacaggc tgtgccagca gtgaatgttt gccctgaatg   9240
cacaccaagg gccccacctg ccacaagaca cataggactc caaagagtct ggcctcacct   9300
```

```
ccctaccatc aatcctgcag aatcgacctc tgctggccgg ctatacc ctg aggtgctctc    9360
tcacttcctc cttcaggttc tgagcagaca ggccaaccgg aggacaggat tccctggagg    9420
ccacagagga gcaccaagga gaagatctgt aagtaagcct ttgttagagc ctctaagatt    9480
tggttctcag ctgaggtctc tcacatgctc cctctctccg taggcctgtg ggtccccatt    9540
gcccagcttt tgcctgcact cttgcctgct gccctgacca gagtcatcat gtcttctgag    9600
cagaagagtc agcactgcaa gcctgaggaa ggcgttgagg cccaagaaga ggccctgggc    9660
ctggtgggtg cacaggctcc tactactgag gagcaggagg ctgctgtctc ctcctcctct    9720
cctctggtcc ctggcaccct ggaggaagtg cctgctgctg agtcagcagg tcctccccag    9780
agtcctcagg gagcctctgc cttacccact accatcagct tcacttgctg gaggcaaccc    9840
aatgagggtt ccagcagcca agaagaggag gggccaagca cctcgcctga cgcagagtcc    9900
ttgttccgag aagcactcag taacaaggtg gatgagttgg ctcatttct gctccgcaag    9960
tatcgagcca aggagctggt cacaaaggca gaaatgctgg agagagtcat caaaaattac   10020
aagcgctgct ttcctgtgat cttcggcaaa gcctccgagt ccctgaagat gatctttggc   10080
attgacgtga aggaagtgga ccccgccagc aacacctaca cccttgtcac ctgcctgggc   10140
ctttcctatg atggcctgct gggtaataat cagatctttc ccaagacagg ccttctgata   10200
atcgtcctgg gcacaattgc aatggagggc gacagcgcct gaggagga aatctgggag    10260
gagctgggtg tgatgggggt gtatgatggg agggagcaca ctgtctatgg ggagcccagg   10320
aaactgctca cccaagattg ggtgcaggaa aactacctgg agtaccggca ggtacccggc   10380
agtaatcctg cgcgctatga gttcctgtgg ggtccaaggg ctctggctga aaccagctat   10440
gtgaaagtcc tggagcatgt ggtcagggtc aatgcaagag ttcgcattgc ctacccatcc   10500
ctgcgtgaag cagctttgtt agaggaggaa gagggagtct gagcatgagt tgcagccagg   10560
gctgtgggga aggggcaggg ctgggccagt gcatctaaca gccctgtgca gcagcttccc   10620
ttgcctcgtg taacatgagg cccattcttc actctgtttg aagaaaatag tcagtgttct   10680
tagtagtggg tttctatttt gttggatgac ttggagattt atctctgttt ccttttacaa   10740
ttgttgaaat gttccttta atggatggtt gaattaactt cagcatccaa gtttatgaat   10800
cgtagttaac gtatattgct gttaatatag tttaggagta agagtcttgt tttttattca   10860
gattgggaaa tccgttctat tttgtgaatt tgggacataa taacagcagt ggagtaagta   10920
tttagaagtg tgaattcacc gtgaaatagg tgagataaat taaagatac ttaattcccg   10980
ccttatgcct cagtctattc tgtaaaattt aaaaatatat atgcatacct ggatttcctt   11040
ggcttcgtga atgtaagaga aattaaatct gaataaaata ttctttctgt taactggctc   11100
atttcttctc tatgcactga gcatctgctc tgtggaaggc ccaggattag tagtggagat   11160
actagggtaa gccagacaca cacctaccga tagggtatta agagtctagg agcgcggtca   11220
tataattaag gtgacaagat gtcctctaag atgtagggga aaagtaacga gtgtgggtat   11280
ggggctccag gtgagagtgg tcgggtgtaa attccctgtg tggggccttt tgggcttttgg   11340
gaaactgcat tttcttctga gggatctgat tctaatgaag cttggtgggt ccaggccag   11400
attctcagag ggagagggaa aagcccagat tggaaaagtt gctctgagca gttcctttgt   11460
gacaatggat gaacagagag gagcctctac ctggg               11495
```

<210> SEQ ID NO 10
<211> LENGTH: 4895
<212> TYPE: DNA
<213> ORGANISM: Homo sapiens -continued

```
<400> SEQUENCE: 10
catccccatc agtgcagcat ccggttccac ccctgctttc aatccaggca agccctgggt        60
ggccggatgt gatgccactg acttgtgaat tgagggttag agagaagtga gtttctgggt       120
ctgaagggtg gcttgagatc ggcagaggga aggtggccca ggctttgtga agaggcaaag       180
tgagactctg agggaggatt caggaaaccc ctatccctga tagagggtcc cagccctgga       240
ctaccccgcg gaggctgact tctcagactg ggctgctccc cacctccgcc ccttcgcaa        300 cgcgtttgtt taagccacag gggactctgg agtcagaggt tggtgtgatc agggaagggc       360
tggttaggag aggcatggcc caggccctgc caggaatcaa agtcagaaac ctgagaggga       420
actgaggtcc cccaagatcc tagtctaacc cccactccca caaatccgct gccatttcgc       480
tgctccattt cccattcctt gccctccacc ctcaccaggc agaatccagt tccccttctg       540
ctatcaatcc agggaaaccc caggcttggt gctgggatgt tttttggggg tcagagaatc       600
aagggcatag tcctgagggg ccagttgaga tcggctgagg ggagcgggcc caagctctgt       660
ggcgaggcaa ggtgagactc tgaggaagga ctgaggaggc cccacccaa gatagaggaa        720 cccaaataat ccagcccacg tcctgctgcc agtcctggac cacccggggg aagacttctc       780
aggctaggcc atcccagctc ccactgccac taaagctaca ggggactcta gagtcaagag       840
cttggtgtgc ccaaggcagg gccaggctct gcctggcatc ggggtcagga ccttgagagg       900
gaactgaggc gctacacccc cacccccatc cgcattccaa catgcccagc ccatccccca       960
actccgtttt gcagaatcca ttttttcccc tgcagtcaac cccgggaaga cctgggaatg      1020
gtcaggcact cggatcttga catccacatc gagggctgaa ggagggagag agtttggtat      1080
catgagcaga gcctcagggt agcagaggga ggaccctggc cctcctggga gatgaggaag      1140
gcctcaggag accagcacc caaggcagg agcccaccc cacccctgtc tgagaatgag         1200
gtgcctcctc ctttagcctc aggaatccaa gggatggcaa ctcaggtcag cagaggggtg      1260
ggttccaagc ccttccagga tcaaggaaag gaagacgagg gaggattcag ggggccttgc      1320
attccagatc agtggagacc tgggccctgg gaggtcctgg gcaaggtagc cacctgtagc      1380
tcatacttcc tgcatcttcg aggtcacaga gaggagaggg ctatggtctg aggggtggta     1440
cttcaggtcc gcagagggag gagtcccagg atctacagga cccaaggtgt gccacacttc      1500
acgaggaatg gggatacctg tggctcagaa agacgggacc ccacagagtc tggctgtccc      1560
ctgttcttag ctcagggggg accagaggag ggatggccct atgtgccaat ttcacttgtt      1620
ccacaggcag gaagttgggg aaccttcagg gagatgaggt tttggagtaa aggggcaatg      1680
tttgctcatc tcagggggtt gggggttgag gaagggcagg ccctgtcagg agcaaacatg      1740 agtaccaca ggaggccatc agaaccctca cccagaacc aaagggtca gccctgggca        1800 ccccacacag gggtgacagg atgtggctcc ttctcatttc tgattccaga tctcagtgag      1860
gtgaggacct tgttctcaga gggtgactca ggtcaccaca gggacccca tctggtctac       1920 agacacagtg gtcccaggat ctgccaagag tcctggtgag aatgtgagg gaggattgag       1980 ggtaccacag ggccagaacg cagatgatga ccccacagaa atcagccctg ctcctgttgt      2040 cacccccagag agcatgggct tggctttctg ctgaggtccc tctcttatcc tgggatcact    2100
ggtgtcacgg agggggaggc cttggtctga ggggctgca cccaggtcag tagagggagg       2160
gtcccaggct ctgccaggag ttgaggtgag gaccaagcag gctccgcatc caggacacat      2220
gggttccaat gaatttcgac atctttttgct gtcgttcttc ggaagaccta ggcacaggtg      2280
```

-continued

| | |
|---|---|
| gccagatgtg gggtttctta ggtcctgttc cctctcaggc atgtgagctc ttgatctgag | 2340 |
| tttctcaggc cagcaaaaga gtgggatcca ggccctgcct ggagaaatgt gagggccctg | 2400 |
| agtgaacaca gtggggatca tccactccat gagagtgggg acctcacaga gtccagccta | 2460 |
| ccctcttgat ggcactgagg gaccggggct gtgcttacag tctgcaccct aagggcccat | 2520 |
| ggattcctct cctaggagct ccaggaacaa ggcagtgagg ccttggtctg agacagtgtc | 2580 |
| ctcaggttac agagcagagg atgcacaggc tgtgccagca gtgaatgttt gccctgaatg | 2640 |
| cacaccaagg gccccacctg ccacaagaca cataggactc caaagagtct ggcctcacct | 2700 |
| ccctaccatc aatcctgcag aatcgacctc tgctggccgg ctataccctg aggtgctctc | 2760 |
| tcacttcctc cttcaggttc tgagcagaca ggccaaccgg aggacaggat tccctggagg | 2820 |
| ccacagagga gcaccaagga gaagatctgt aagtaagcct tgttagagc ctctaagatt | 2880 |
| tggttctcag ctgaggtctc tcacatgctc cctctctccg taggcctgtg ggtccccatt | 2940 |
| gcccagcttt tgcctgcact cttgcctgct gccctgagca gagtcatcat gtcttctgag | 3000 |
| cagaagagtc agcactgcaa gcctgaggaa ggcgttgagg cccaagaaga ggccctgggc | 3060 |
| ctggtgggtg cgcaggctcc tactactgag gagcaggagg ctgctgtctc ctcctcctct | 3120 |
| cctctggtcc ctggcaccct ggaggaagtg cctgctgctg agtcagcagg tcctccccag | 3180 |
| agtcctcagg gagcctctgc cttacccact accatcagct tcacttgctg gaggcaaccc | 3240 |
| aatgagggtt ccagcagcca agaagaggag gggccaagca cctcgcctga cgcagagtcc | 3300 |
| ttgttccgag aagcactcag taacaaggtg gatgagttgg ctcatttctt gctccgcaag | 3360 |
| tatcgagcca aggagctggt cacaaaggca gaaatgctgg agagagtcat caaaaattac | 3420 |
| aagcgctgct ttcctgtgat cttcggcaaa gcctccgagt ccctgaagat gatctttggc | 3480 |
| attgacgtga aggaagtgga ccccaccagc aacacctaca cccttgtcac ctgcctgggc | 3540 |
| ctttcctatg atggcctgct gggtaataat cagatctttc ccaagacagg ccttctgata | 3600 |
| atcgtcctgg gcacaattgc aatggagggc gacagcgcct ctgaggagga aatctgggag | 3660 |
| gagctgggtg tgatggggt gtatgatggg agggagcaca ctgtctatgg ggagcccagg | 3720 |
| aaactgctca cccaagattg ggtgcaggaa aactacctgg agtaccggca ggtacccggc | 3780 |
| agtaatcctg cgcgctatga gttcctgtgg ggtccaaggg ctctggctga accagctat | 3840 |
| gtgaaagtcc tggagcatgt ggtcagggtc aatgcaagag ttcgcattgc ctacccatcc | 3900 |
| ctgcgtgaag cagcttttgt agaggaggaa gagggagtct gagcatgagt tgcagccagg | 3960 |
| gctgtgggga agggcaggg ctgggccagt gcatctaaca gccctgtgca gcagcttccc | 4020 |
| ttgcctcgtg taacatgagg cccattcttc actctgtttg aagaaaatag tcagtgttct | 4080 |
| tagtagtggg tttctatttt gttggatgac ttggagattt atctctgttt ccttttacaa | 4140 |
| ttgttgaaat gttccttta atggatggtt gaattaactt cagcatccaa gtttatgaat | 4200 |
| cgtagttaac gtatattgct gttaatatag tttaggagta agagtcttgt tttttattca | 4260 |
| gattgggaaa tccgttctat tttgtgaatt tgggacataa aacagcagt ggagtaagta | 4320 |
| tttagaagtg tgaattcacc gtgaaatagg tgagataaat taaagatac ttaattcccg | 4380 |
| ccttatgcct cagtctattc tgtaaaattt aaaaatatat atgcatacct ggatttcctt | 4440 |
| ggcttcgtga atgtaagaga aattaaatct gaataaataa ttctttctgt taactggctc | 4500 |
| atttcttctc tatgcactga gcatctgctc tgtggaaggc ccaggattag tagtggagat | 4560 |
| actagggtaa gccagacaca cacctaccga tagggtatta agagtctagg agcgcggtca | 4620 |
| tataattaag gtgacaagat gtcctctaag atgtagggga aaagtaacga gtgtgggtat | 4680 |

-continued

```
ggggctccag gtgagagtgg tcgggtgtaa attccctgtg tggggccttt tgggctttgg      4740
gaaactccat tttcttctga gggatctgat tctaatgaag cttggtgggt ccagggccag      4800
attctcagag ggagagggaa aagcccagat tggaaaagtt gctctgagcg gttcctttgt      4860
gacaatggat gaacagagag gagcctctac ctggg                                 4895
```

<210> SEQ ID NO 11
<211> LENGTH: 4741
<212> TYPE: DNA
<213> ORGANISM: Homo sapiens

<400> SEQUENCE: 11

```
gttctgctcc tgctttcaac ccagggaatc cctgggtgac cagatgtggt gccactgtct        60
tgcacatttg aggtcggaga gaagcaaggg cctcgctctc aggggcagct ggagatcagc       120
tgagggcagc tggccctggc tctgtgagga tgcaaggtga gatgctgagg gaggactaag       180
gagtatccca cccctggtag tggaccccaa ataatccagt gccacctctc ctgctgctag       240
ctctggacca tccagggcag gacttcttag gctgggccac ccccagtccc ccaccgctta       300
agccgcaggg gactcaggag acagagcttg gtatgaccag ggcaggactg gttaggagag       360
gacagctccc agctctgcca ggaaacaacg tcaggaacct aagggaaagc tgaggctacc       420
cccaccccaa actctattcc tgtccctacc tccgtcccccc acctacaccc cccattcccc      480
caccccttcc ctaccggcac ctctatccca catcccccac ccctatcctg gcagaatccg       540
attctgcccc tgatttcaac ccagggaagc cctaggggc cggatgtgat gctgctgact        600
tgtgcattgg gggtcagaga gaatcaaggg catggttctg agaagccgac tgagatcagc       660
agagggggaat gggcccgggc tctgtgagga ggcaaggtga dccccccgag aaggaatga       720
ggaagccctc acccagatag agaaccccaa ataatccagt actacctttg ctgccagccc       780
tggaccaccc agggcagact tctcaggctg aaccttcccc cctccccact gccacttaag       840
ccacaaggga ctctggagtc agaccttggt gtgaccaggg aagggccggt caggagaggg       900
caggggccag gctctgtcag gcatcaaaat caggaccctg agagagaatt gagggccccc       960
accccaaccc ctatacccat ccctaacccc atacccactc tacttgcatt cccagcccca      1020
tccccacacc ctacccccatc ttggcagaat ctgtttcttt ccctgcagtc aacccacaga    1080
agccccagga atgacagaca ggcacaccta ttctgacgtc cacatccagg gctgaaggag     1140
ggaaagggct tagtatcatg agcagggcct caggggagtc tctgctcctc aagccctgct     1200
gggagtaaag ggaggcctca gggaacccag gtcctcagga taggggtcc actccaaccc      1260
tgtctgagac tgaggcgcct cctctttcat cctcgggaat cacaggatg gagactcacg      1320
tcagcagagg gtgggcccca accctgccag gatcaaggag aggaagaaga gggaggactc     1380
agggtacctt tgagtccaga acaatgggga cctttgccct ggaggtcca gtgcacagtg     1440
gccacctgta gcccatgctt gctgcacctt ctgggtgaca aagaggagag ggctgtggtc     1500
agagcagtgg tgactcaggt cagcagaggg aggagtccca gcatctgcag gccccaatgt    1560
gtgcccccatt catgaagatt ggggatacct tggctcagaa agaagggacc ccacagagtc    1620
tggctgtccc ctgattttg ctcagagggg accaaatcaa ggatagccct atgtgccaac      1680
ctcatttgtg ccacaggaaa gaagttgaag agccctcagg gtgatggggt cttgcagtaa     1740
aggggagcta tctgctcatc tcagggggtt tcaggttgag gaatggcagg ccccatcacg     1800
atgaagagta acccacagga gccatagaaa cactcacccc agaaccaaag gggtcatacc     1860
```

```
tggacacccc atgtgggggt gacaggatgt agctccatct cattcctgtt ttcagatctc   1920
ggggaggtga ggaacttgtt ctccgaggat gactcaggtc aacacagggg cccccatctg   1980
gtggatagac agagtggtcc caggatctgt cagtagttcc ggtgaggaac atgagggacg   2040
attgagggca cccttgggcc agaacacaga tgaggacctc acggaaatct gccctgcccc   2100
tgctgtcact ccagagagca tgggcagggc tgtctgctgc agtccccccc acttaccctg   2160
ggatcattgg tgtcagggat ggggaggtct tgtcgaggg gtctgcactc aggtcagtag    2220
agggagcgtc ttaggccctg ccaggagaca aggtaagaac gaagcaggtt cctcacccag   2280
gacacatgaa ttccaatgca tttcagcatc tcttcctgtc cttcccaaga ggacctgggc   2340
acgtgtggcc agatgtgagt ctcctcatgt cctgttccct atcagggatg tgagctctta   2400
atctgagttt ctcaggccag caaaagggtg ggatccaggc cttgccagga gaaggtgag    2460 ggccctgtgt gagcacagag gggaccattc accccaagag ggtggagacc tcacagattc   2520
cagcctaccc tcctgttagc actgggggcc tgaggctgtg cttgcagtct gcaccctgag   2580
ggcccatgca ttcctcttcc aggagctcca ggaaacagac actgaggcct tggtctgagg   2640
ccgtgccctc aggtcacaga gcagaggaga tgcagacgtc tagtgccagc agtgaacgtt   2700
tgccttgaat gcacactaat ggcccccatc gccccagaac atatgggact ccagagcacc   2760
tggcctcacc ctctctactg tcagtcctgc agaatcagcc tctgcttgct tgtgtaccct   2820
gaggtgccct ctcacttttt ccttcaggtt ctcagggac aggctgacca ggatcaccag    2880
gaagctccag aggatcccca ggaggcccta gaggagcacc aaaggagaag atctgtaagt   2940
aagcctttgt tagagcctcc aaggttcagt ttttagctga ggcttctcac atgctccctc   3000
tctctccagg ccagtgggtc tccattgccc agctcctgcc cacactcctg cctgttgcgg   3060
tgaccagagt cgtcatgtct cttgagcaga agagtcagca ctgcaagcct gaggaaggcc   3120 ttgacacccca agaagaggcc ctgggcctgg tgggtgtgca ggctgccact actgaggagc   3180
aggaggctgt gtcctcctcc tctcctctgg tcccaggcac cctggggag gtgcctgctg    3240 ctgggtcacc aggtcctctc aagagtcctc agggagcctc cgccatcccc actgccatcg   3300
atttcactct atggaggcaa tccattaagg gctccagcaa ccaagaagag gaggggccaa   3360
gcacctcccc tgacccagag tctgtgttcc gagcagcact cagtaagaag gtggctgact   3420
tgattcattt tctgctcctc aagtattaag tcaaggagct ggtcacaaag gcagaaatgc   3480
tggagagcgt catcaaaaat tacaagcgct gctttcctga gatcttcggc aaagcctccg   3540
agtccttgca gctggtcttt ggcattgacg tgaaggaagc ggaccccacc agcaacacct   3600
acacccttgt cacctgcctg ggactcctat gatggcctgc tggttgataa taatcagatc   3660
atgcccaaga cgggcctcct gataatcgtc ttgggcatga ttgcaatgga gggcaaatgc   3720
gtccctgagg agaaaatctg ggaggagctg agtgtgatga aggtgtatgt tgggagggag   3780
cacagtgtct gtggggagcc caggaagctg ctcacccaag atttggtgca ggaaaactac   3840
ctggagtacc ggcaggtgcc cagcagtgat cccatatgct atgagttact gtggggtcca   3900
agggcactcg ctgcttgaaa gtactggagc acgtggtcag ggtcaatgca agagttctca   3960
tttcctaccc atccctgcgt gaagcagctt tgagagagga ggaagaggga gtctgagcat   4020
gagctgcagc cagggccact gcgagggggg ctgggccagt gcaccttcca gggctccgtc   4080
cagtagtttc ccctgcctta atgtgacatg aggcccattc ttctctcttt gaagagagca   4140
gtcaacattc ttagtagtgg gtttctgttc tattggatga ctttgagatt tgtctttgtt   4200
tccttttgga attgttcaaa tgtttctttt aatgggtggt tgaatgaact tcagcattca   4260
```

-continued

| | |
|---|---|
| aatttatgaa tgacagtagt cacacatagt gctgtttata tagtttagga gtaagagtct | 4320 |
| tgtttttat tcagattggg aaatccattc cattttgtga attgggacat agttacagca | 4380 |
| gtggaataag tattcattta gaaatgtgaa tgagcagtaa aactgatgac ataaagaaat | 4440 |
| taaaagatat ttaattcttg cttatactca gtctattcgg taaaattttt tttaaaaaat | 4500 |
| gtgcatacct ggatttcctt ggcttctttg agaatgtaag acaaattaaa tctgaataaa | 4560 |
| tcattctccc tgttcactgg ctcatttatt ctctatgcac tgagcatttg ctctgtggaa | 4620 |
| ggccctgggt taatagtgga gatgctaagg taagccagac tcaccctac ccacagggta | 4680 |
| gtaaagtcta ggagcagcag tcatataatt aaggtggaga gatgccctct aagatgtaga | 4740 |
| g | 4741 |

<210> SEQ ID NO 12
<211> LENGTH: 4736
<212> TYPE: DNA
<213> ORGANISM: Homo sapiens

<400> SEQUENCE: 12

| | |
|---|---|
| gttctgctcc tgctttcaac ccagggaatc cctgggtgac cagatgtggt gccactgtct | 60 |
| tgcacatttg aggtcggaga gaagcaaggg cctcgctctc aggggcagct ggagatcagc | 120 |
| tgagggcagc tggccctggc tctgtgagga tgcaaggtga gatgctgagg gaggactaag | 180 |
| gagtatccca cccctggtag tggaccccaa ataatccagt gccacctctc ctgctgctag | 240 |
| ctctggacca tccagggcag gacttcttag gctgggccac ccccagtccc ccaccgctta | 300 |
| agccgcaggg gactcaggag acagagcttg tatgaccag gcaggactg gttaggagag | 360 |
| gacagctccc agctctgcca ggaaacaacg tcaggaacct aagggaaagc tgaggctacc | 420 |
| cccacccccaa actctattcc tgtccctacc tccgtccccc acctacaccc ccattcccc | 480 |
| caccccttcc ctaccggcac ctctatccca catccccac cctatcctg gcagaatccg | 540 |
| attctgcccc tgatttcaac ccagggaagc cctaggggc cggatgtgat gctgctgact | 600 |
| tgtgcattgg gggtcagaga gaatcaaggg catggttctg agaagccgac tgagatcagc | 660 |
| agaggggaat gggcccgggc tctgtgagga ggcaaggtga daccccgag gaaggaatga | 720 |
| ggaagccctc acccagatag agaaccccaa ataatccagt actacctctg ctgccagccc | 780 |
| tggaccaccc agggcagact tctcaggctg aaccttcccc cctccccact gccacttaag | 840 |
| ccacaaggga ctctggagtc agaccttggt gtgaccaggg aagggccggt caggagaggg | 900 |
| caggggccag gctctgtcag gcatcaaaat caggaccctg agagagaatt gagggccccc | 960 |
| accccaaccc ctatacccat ccctaacccc atacccactc tacttgcatt cccagcccca | 1020 |
| tcccacacc ctaccccatc ttggcagaat ctgtttctt ccctgcagtc aacccacaga | 1080 |
| agccccagga atgacagaca ggcacaccca ttctgacgtc cacatccagg gctgaaggag | 1140 |
| ggaaagggct tagtatcatg agcagggcct caggggagtc tctgctcctc aagccctgct | 1200 |
| gggagtaaag ggaggcctca gggaacccag gtcctcagga tagggggtcc actccaaccc | 1260 |
| tgtctgagac tgaggcgcct cctctttcat cctcgggaat cacagggatg gagactcacg | 1320 |
| tcagcagagg gtggggccca accctgccag gatcaaggag aggaagaaga gggaggactc | 1380 |
| agggtaccttt tgagtccaga acaatgggga cctttgccct gggaggtcca gtgcacagtg | 1440 |
| gccacctgta gccatgcttt gctgcacctt ctgggtgaca aagaggagag ggctgtggtc | 1500 |
| agagcagtgg tgactcaggt cagcagaggg aggagtccca gcatctgcag gccccaatgt | 1560 |

```
gtgccccatt catgaagatt ggggacacct tggctcagaa agaagggacc ccacagagtc   1620
tggctgtccc ctgattttg  ctcagagggg accaaatcaa ggatagccct atgtgccaac   1680
ctcatttgtg ccacaggaaa gaagttgaag agccctcagg gtgatgggt  cttgcagtaa   1740
agggagcta  tctgctcatc tcaggggtt  tcaggttgag gaatggcagg ccccatcacg   1800
atgaagagta acccacagga gccatagaaa cactcacccc agaaccaaag ggtcatacc    1860
tggacacccc atgtgggggt gacaggatgt agctccatct cattcctgtt ttcagatctc   1920
ggggaggtga ggaacttgtt ctccgaggat gactcaggtc aacacagggg cccccatctg   1980
gtggatagac agagtggtcc caggatctgt cagtagttcc ggtgaggaac atgagggacg   2040
attgagggca cccttgggcc agaacacaga tgaggacctc acggaaatct gccctgcccc   2100
tgctgtcact ccagagagca tgggcagggc tgtctgctgc agtcccccc  acttaccctg   2160
ggatcattgg tgtcagtgat ggggaggtct ttgtcgaggg gtctgcactc aggtcagtag   2220
agggagcgtc ttaggccctg ccaggagaca aggtaagaac gaagcaggtt cctcacccag   2280
gacacatgaa ttccaatgca tttcagcatc tcttcctgtc cttcccaaga ggacctgggc   2340
acgtgtggcc agatgtgagt ctcctcatgt cctgttccct atcagggatg tgagctctta   2400
atctgagttt ctcaggccag caaaagggtg ggatccaggc cttgccagga gaaaggtgag   2460
ggccctgtgt gagcacagag gggaccattc accccaagag ggtggagacc tcacagattc   2520
cagcctaccc tcctgttagc actgggggcc tgaggctgtg cttgcagtct gcaccctgag   2580
ggcccatgca ttcctcttcc aggagctcca ggaaacagac actgaggcct tggtctgagg   2640
ccgtgccctc aggtcacaga gcagaggaga tgcagcgtc  tagtgccagc agtgaacgtt   2700
tgccttgaat gcacactaat ggcccccatc gccccagaac atatgggact ccagagcacc   2760
tggcctcacc ctctctactg tcagtcctgc agaatcagcc tctgcttgct tgtgtaccct   2820
gaggtgccct ctcactttt  ccttcaggtt ctcagggaca aggctgacca ggatcaccag   2880
gaagctccag aggatcccca ggaggcccta gaggagcacc aaaggagaag atctgtaagt   2940
aagcctttgt tagagcctcc aaggttcagt ttttagctga ggcttctcac atgctccctc   3000
tctctccagg ccagtgggtc tccattgccc agctcctgcc cacactcctg cctgttgcgg   3060
tgaccagagt cgtcatgtct cttgagcaga agagtcagca ctgcaagcct gaggaaggcc   3120
ttgacaccca agaagaggcc ctgggcctgg tgggtgtgca ggctgccact actgaggagc   3180
aggaggctgt gtcctcctcc tctcctctgg tcccaggcac cctgggggag gtgcctgctg   3240
ctgggtcacc aggtcctctc aagagtcctc agggagcctc cgccatcccc actgccatcg   3300
atttcactct atggaggcaa tccattaagg gctccagcaa ccaagaagag gaggggccaa   3360
gcacctcccc tgacccagag tctgtgttcc gagcagcact cagtaagaag gtggctgact   3420
tgattcattt tctgctcctc aagtattaag tcaaggagcc ggtcacaaag gcagaaatgc   3480
tggagagcgt catcaaaaat tacaagcgct gctttcctga gatcttcggc aaagcctccg   3540
agtccttgca gctggtcttt ggcattgacg tgaaggaagc ggacccccacc agcaacacct   3600
acacccttgt cacctgcctg ggactcctat gatggcctgg tggtttaatc agatcatgcc   3660
caagacgggc ctcctgataa tcgtcttggg catgattgca atggagggca aatgcgtccc   3720
tgaggagaaa atctgggagg agctgggtgt gatgaaggtg tatgttggga gggagcacag   3780
tgtctgtggg gagcccagga agctgctcac ccaagatttg gtgcaggaaa actacctgga   3840
gtaccgcagg tgcccagcag tgatcccata tgctatgagt tactgtgggg tccaagggca   3900
ctcgctgctt gaaagtactg gagcacgtgg tcagggtcaa tgcaagagtt ctcatttcct   3960
```

-continued

```
acccatccct gcatgaagca gctttgagag aggaggaaga gggagtctga gcatgagctg    4020
cagccagggc cactgcgagg ggggctgggc cagtgcacct tccagggctc cgtccagtag    4080
tttcccctgc cttaatgtga catgaggccc attcttctct ctttgaagag agcagtcaac    4140
attcttagta gtgggtttct gttctattgg atgactttga gatttgtctt tgtttccttt    4200
tggaattgtt caaatgttcc ttttaatggg tggttgaatg aacttcagca ttcaaattta    4260
tgaatgacag tagtcacaca tagtgctgtt tatatagttt aggagtaaga gtcttgtttt    4320
ttattcagat tgggaaatcc attccatttt gtgaattggg acatagttac agcagtggaa    4380
taagtattca tttagaaatg tgaatgagca gtaaaactga tgagataaag aaattaaaag    4440
atatttaatt cttgccttat actcagtcta ttcggtaaaa ttttttttta aaaatgtgca    4500
tacctggatt tccttggctt ctttgagaat gtaagacaaa ttaaatctga ataaatcatt    4560
ctccctgttc actggctcat ttattctcta tgcactgagc atttgctctg tggaaggccc    4620
tgggttaata gtggagatgc taaggtaagc cagactcacc cctacccaca gggtagtaaa    4680
gtctaggagc agcagtcata taattaaggt ggagagatgc cctctaagat gtagag        4736
```

<210> SEQ ID NO 13
<211> LENGTH: 1019
<212> TYPE: DNA
<213> ORGANISM: Homo sapiens

<400> SEQUENCE: 13

```
gccagtgggt ctccattgcc cagctcctgc ccacactccc gcctgttgcc ctgaccagag     60
tcatcatgcc tcttgagcag aggagtcagc actgcaagcc tgaagaaggc cttgaggccc    120
gaggagaggc cctgggcctg gtgggtgcgc aggctcctgc tactgaggag caggaggctg    180
cctcctcctc ttctactcta gttgaagtca ccctggggga ggtgcctgct gccgagtcac    240
cagatcctcc ccagagtcct cagggagcct ccagcctccc cactaccatg aactaccctc    300
tctggagcca atcctatgag gactccagca accaagaaga ggaggggcca agcaccttcc    360
ctgacctgga gtctgagttc caagcagcac tcagtaggaa ggtggccaag ttggttcatt    420
ttctgctcct caagtatcga gccagggagc cggtcacaaa ggcagaaatg ctggggagtg    480
tcgtcggaaa ttggcagtac ttctttcctg tgatcttcag caaagcttcc gattccttgc    540
agctggtctt tggcatcgag ctgatggaag tggaccccat cggccacgtg tacatctttg    600
ccacctgcct gggcctctcc tacgatggcc tgctgggtga caatcagatc atgcccaaga    660
caggcttcct gataatcatc ctggccataa tcgcaaaaga gggcgactgt gcccctgagg    720
agaaaatctg ggaggagctg agtgtgttag aggtgtttga ggggagggaa gacagtatct    780
tcggggatcc caagaagctg ctcacccaat atttcgtgca ggaaaactac ctggagtacc    840
ggcaggtccc cggcagtgat cctgcatgct atgagttcct gtggggtcca agggccctca    900
ttgaaaccag ctatgtgaaa gtcctgcacc atatggtaaa gatcagtgga ggacctcgca    960
tttcctaccc actcctgcat gagtgggctt tgagagaggg ggaagagtga gtctgagca    1019
```

<210> SEQ ID NO 14
<211> LENGTH: 3839
<212> TYPE: DNA
<213> ORGANISM: Homo sapiens

<400> SEQUENCE: 14

```
agtctcagat cactggagag aggtgcccca gagcccttaa ggaggactca gcagacctcc     60
```

-continued

| | |
|---|---|
| catcatggcc taggaaacct gctcccactc tcaggtctgg gcacccaagg caggacagtg | 120 |
| gggaagggat gtggccccc cactttctgg tagggggcc tcaaggagat ggtggccttg | 180 |
| gcatgcaaga cacatccacg gttcagcagg aaggaaaggg ccatgccttg tcgtggagta | 240 |
| aatatgaata cctggatgac acccagacag agaaagaccc catgaaacct actacttctg | 300 |
| tcagccgtgg gaatcccatg cagggttgtc catgtagtgc ctccttactt ctgcctcctg | 360 |
| ggtctcaggg aggtagcaac ctgggtctga agggcgtcct cagctcagca gagggagcca | 420 |
| cacctgttca acagagggac ggggtcacag gatctgcagg acccaagatg tgctcacttt | 480 |
| gtgatgaatg ggggtactcc tggcctggaa agaagggacc ccacaaagtc tggctaactt | 540 |
| tggttattat ctctgggga acccgatcaa gggtggccct aagtggagat ctcatctgta | 600 |
| ctgtgggcag gaagttgggg aaacgcagga agataaggtc ttggtggtaa ggggagatgt | 660 |
| ctgctcatat caggtgttg tgggttgagg aagggcgggc tccatcaggg gaaagatgaa | 720 |
| taacccctg aagaccttag aacccaccac tcaagaacaa gtagggacag atcctagtgt | 780 |
| caccctggaa caccccaccc agtggtcatc agatgtggtg gctcctcatt tctctcttga | 840 |
| gtctcaggga agtgaggacc ttgttctcag agggcaactc aggacaaaac agggaccccc | 900 |
| atgtgggcaa cagactcagt ggtccaagaa tctaccaaga gtctaggtga caacactgag | 960 |
| ggaagattga gggtaccctc gatggttctc ctagcaggca aaaaacagat gggggcccaa | 1020 |
| cagaaatctg cccggcctct tttgtcaccc ctgagagcat gagcaggact atcagctgag | 1080 |
| gccctgtgt tataccagac tcattggtct cagggagaag aaggccttgg tctgagggca | 1140 |
| ctgcattcag gtcagcagag cggggtcca aggccctgcc aggagtcagg gactcagagg | 1200 |
| acaccactca ccaaacacac aggaccgaac cccacccgc accttctgtc agccatggga | 1260 |
| agtgcaggga aggtggggtg gatggaatcc cctcatttgc tcttccagtg tctcctggag | 1320 |
| ataggtcctt ggattaagga agtggcctca ggtcagccca ggacacatgg gccccaatgt | 1380 |
| attttgtgta gctattgctt ttttctcacc ctaggacaga cacgtgggcc ccattgcatt | 1440 |
| ttgtgtagct attgcttttt tcccaggagg ccttgggcat gtggggccag atgtgggtcc | 1500 |
| cttcatatcc ttgtcttcca tatcagggat ataaactctt gatctgaaag tttctcaggc | 1560 |
| cagcaaaagg gccagatcca ggccctgcca ggagaaagat gagggccctg aatgagcaca | 1620 |
| gaaaggacca tccacacaaa atagtgggga gctcacagag tcaggctcac cctcctgaca | 1680 |
| gcactggggt gctggggctg tgcttgcagt ctgcagcctg agttccctc gatttatctt | 1740 |
| ctaggagctc caggaaccag gctgtgaggt cttggtctga ggcagtatct tcaatcacag | 1800 |
| agcataagag gcccaggcag tagtagcagt caagctgagg tggtgtttcc cctgtatgta | 1860 |
| taccagaggc ccctctggca tcagaacagc aggaacccca cagttcctgg ccctaccagc | 1920 |
| ccttttgtca gtcctggagc cttggccttt gccaggaggc tgcaccctga gatgccctct | 1980 |
| caatttctcc ttcaggttcg cagagaacag gccagccagg aggtcaggag gccccagaga | 2040 |
| agcactgaag aagacctgta agtagacctt tgttagggca tccagggtgt agtacccagc | 2100 |
| tgaggcctct cacacgcttc ctctctcccc aggcctgtgg gtctcaattg cccagctccg | 2160 |
| gcccacactc tcctgctgcc ctgacctgag tcatcatgct tcttgggcag aagagtcagc | 2220 |
| gctacaaggc tgaggaaggc cttcaggccc aaggagaggc accagggctt atggatgtgc | 2280 |
| agattcccac agctgaggag cagaaggctg catcctcctc ctctactctg atcatgggaa | 2340 |
| cccttgagga ggtgactgat tctgggtcac caagtcctcc ccagagtcct gagggtgcct | 2400 |
| cctcttccct gactgtcacc gacagcactc tgtggagcca atccgatgag ggttccagca | 2460 |

```
gcaatgaaga ggaggggcca agcacctccc cggacccagc tcacctggag tccctgttcc    2520
gggaagcact tgatgagaaa gtggctgagt tagttcgttt cctgctccgc aaatatcaaa    2580
ttaaggagcc ggtcacaaag gcagaaatgc ttgagagtgt catcaaaaat tacaagaacc    2640
actttcctga tatcttcagc aaagcctctg agtgcatgca ggtgatcttt ggcattgatg    2700
tgaaggaagt ggaccctgcc ggccactcct acatccttgt cacctgcctg ggcctctcct    2760
atgatggcct gctgggtgat gatcagagta cgcccaagac cggcctcctg ataatcgtcc    2820
tgggcatgat cttaatggag ggcagccgcg ccccggagga ggcaatctgg gaagcattga    2880
gtgtgatggg ggctgtatga tgggagggag cacagtgtct attggaagct caggaagctg    2940
ctcacccaag agtgggtgca ggagaactac ctggagtacc gccaggcgcc cggcagtgat    3000
cctgtgcgct acgagttcct gtgggtccaa agggcccttg ctgaaaccag ctatgtgaaa    3060
gtcctggagc atgtggtcag ggtcaatgca agagttcgca tttcctaccc atccctgcat    3120
gaagaggctt tgggagagga gaaggagtt tgagcaggag ttgcagctag gccagtggg    3180 gcaggttgtg ggagggcctg ggccagtgca cgttccaggg ccacatccac cactttccct    3240
gctctgttac atgaggccca ttcttcactc tgtgtttgaa gagagcagtc acagttctca    3300
gtagtgggga gcatgttggg tgtgagggaa cacagtgtgg accatctctc agttcctgtt    3360
ctattgggcg atttggaggt ttatctttgt ttccttttgg aattgttcca atgttccttc    3420
taatggatgg tgtaatgaac ttcaacattc attttatgta tgacagtaga cagacttact    3480 gcttttata tagtttagga gtaagagtct tgcttttcat ttatactggg aaacccatgt    3540
tatttcttga attcagacac tacaagagca gaggattaag gttttttttag aaatgtgaaa    3600 caacatagca gtaaaatca tgagataaag acataaagaa attaaacaat agttaattct    3660
tgccttacct gtacctctta gtgtacccta tgtacctgaa tttgcttggc ttctttgaga    3720
atgaaattga attaaatatg aataaataag tcccctgct cactggctca ttttttccca    3780
aaatattcat tgagcttccg ctatttggaa ggccctgggt tagtattgga gatgctaca    3839

<210> SEQ ID NO 15
<211> LENGTH: 2931
<212> TYPE: DNA
<213> ORGANISM: Homo sapiens

<400> SEQUENCE: 15
ggatccggcc ggatctcagg gaggtgagga ctttgttctc agagggtgtg tgtggacaaa      60
acagggaggc cctgtgttcg acagacacag tggtcccagg attggagagc agtccaggtg     120
aggaacctaa gggaggatcg agggtacctc caggccagag aaactctcag atcaagagag     180
tttgccctgc ccctactgtc accccagaga gcccgggcag ggctgtctgc tgaggtccct     240
cctttatcct gggatcactg gtgtcgggga gggctggcct tggtctgagg gggctgcact     300
cacgtcagca gagggagggt cccaggccct gccaggagtc caggtgcaga ctgaggggac     360
cccactcacc aaacacagag gacctagccc caccctgccc cttgtgtcag ctgagggaag     420
ccgctgggtg gatggactcc cctcacttcc tcttcaggtg tctcctggag atagggcctc     480
aggtcaacag agggagggtt ccagaccctg caggcatcaa gatgaggacc aggcagtatc     540
ctcaccccag gacacatgga ccccattgaa tttagacatc tcttactgta cttccgagga     600
aaccctgggc aggtgtgggc agatgttggt tggggcatgt ccttctgttc catatcaggg     660
atgtgagctc ctgatctgag agactctcag gcaagtagag gagtagagtc cagtccctgc     720
```

-continued

```
caggagaaag gtcagggccc tgagtgagcg cagaggggac catccacccc aaaagtgtgt    780
agaactcaag agtgtccagc ccgccctctt gacagcactg agggaccggg gctctgcctg    840
cagtctgcag cctaagggcc cctcgattcc tcttccagga gctccaggaa gcaggcaggc    900
cttggtctga cacagtgtcc tcaggtcgca gagcagagga gacccaggca gtgtcagcag    960
tgaaggtgaa gtgttcaccc tgaatgtgca ccaagggccc cacctgcccc agcacacatg   1020 ggacccata gcacctggcc ccattccccc tactgtcact catagagcct tgatctctgc    1080
aggctagctg cacgctgagt agccctctca cttcctccct caggttctcg ggacaggcta   1140
accaggagga caggagcccc aagaggcccc agagcagcac tgacgaagac ctgtaagtca   1200
gcctttgtta gaacctccaa ggttcggttc tcagctgaag tctctcacac actccctctc   1260
tccccaggcc tgtgggtctc catcgcccag ctcctgccca cgctcctgac tgctgccctg   1320
accagagtca tcatgtctct cgagcagagg agtccgcact gcaagcctga tgaagacctt   1380
gaagcccaag gagaggactt gggcctgatg ggtgcacagg aacccacagg cgaggaggag   1440
gagactacct cctcctctga cagcaaggag gaggaggtgt ctgctgctgg gtcatcaagt   1500
cctccccaga gtcctcaggg aggcgcttcc tcctccattt ccgtctacta cactttatgg   1560
agccaattcg atgagggctc cagcagtcaa gaagaggaag agccaagctc ctcggtcgac   1620
ccagctcagc tggagttcat gttccaagaa gcactgaaat tgaaggtggc tgagttggtt   1680
catttcctgc tccacaaata tcgagtcaag gagccggtca caaaggcaga aatgctggag   1740
agcgtcatca aaaattacaa gcgctacttt cctgtgatct tcggcaaagc ctccgagttc   1800
atgcaggtga tctttggcac tgatgtgaag gaggtggacc ccgccggcca ctcctacatc   1860
cttgtcactg ctcttggcct ctcgtgcgat agcatgctgg gtgatggtca tagcatgccc   1920
aaggccgccc tcctgatcat tgtcctgggt gtgatcctaa ccaaagacaa ctgcgcccct   1980
gaagaggtta tctgggaagc gttgagtgtg atggggtgt atgttgggaa ggagcacatg   2040
ttctacgggg agcccaggaa gctgctcacc caagattggg tgcaggaaaa ctacctggag   2100
taccggcagg tgcccggcag tgatcctgcg cactacgagt tcctgtgggg ttccaaggcc   2160
cacgctgaaa ccagctatga gaaggtcata aattatttgg tcatgctcaa tgcaagagag   2220
cccatctgct acccatccct ttatgaagag gttttgggag aggagcaaga gggagtctga   2280
gcaccagccg cagccggggc caaagtttgt ggggtcaggg ccccatccag cagctgccct   2340
gccccatgtg acatgaggcc cattcttcgc tctgtgtttg aagagagcaa tcagtgttct   2400
cagtggcagt gggtggaagt gagcacactg tatgtcatct ctgggttcct tgtctattgg   2460
gtgatttgga gatttatcct tgctcccttt tggaattgtt caaatgttct tttaatggtc   2520
agtttaatga acttcaccat cgaagttaat gaatgacagt agtcacacat attgctgttt   2580
atgttattta ggagtaagat tcttgctttt gagtcacatg gggaaatccc tgttattttg   2640
tgaattggga caagataaca tagcagagga attaataatt tttttgaaac ttgaacttag   2700
cagcaaaata gagctcataa agaaatagtg aaatgaaaat gtagttaatt cttgccttat   2760
acctctttct ctctcctgta aaattaaaac atatacatgt atacctggat ttgcttggct   2820
tctttgagca tgtaagagaa ataaaaattg aaagaataat ttttcctgtt cactggctca   2880 tttttcttc agacacgcac tgaacatctg ttattcggaa caccctgggt t             2931
```

<210> SEQ ID NO 16
<211> LENGTH: 3510
<212> TYPE: DNA
<213> ORGANISM: Homo sapiens

<400> SEQUENCE: 16

| | | | | | |
|---|---|---|---|---|---|
| cagggagatg | gtggctttgg | cgtgcaagac | ccatacacga | ttcagcagga | gggaaaggct | 60 |
| gggctgtcgg | gagtaaatct | gaatacctgg | aggacaccca | aataaaggaa | gtccccgtct | 120 |
| tgtccccctc | ccctgcccac | caccccccc | cccccgcca | aatgtctgct | ccttctgtca | 180 |
| gctttgggaa | tcccatgcag | gtgtgatcgt | gtggtgcccc | tccccacttc | tgcctgccgg | 240 |
| gtctcaggga | ggtgaggacc | ttggtctgag | ggttgctaag | aagttattac | agggttccac | 300 |
| acttggtcaa | cagagggagg | agtcccagaa | tctgcaggac | ccaaggggtg | ccccttagt | 360 |
| gaggactgga | ggtacctgca | gcccagaaag | aagggatgtc | acagagtctg | gctgtcccct | 420 |
| gttcttagct | ctgaggggac | ctgatcagga | ttggcactaa | gtggcaagct | caattttacc | 480 |
| acaggcagga | agatgaggaa | ccctcaggga | aatggagttt | tggtgtaaag | gggagatatc | 540 |
| agccctggac | accccacagg | gatgacagga | tgtggctcct | tcttactttt | gttttggaat | 600 |
| ctcagggagg | tgagaacctt | gctctcagag | ggtgactcaa | gtcaacacag | gaacccctc | 660 |
| ttttctacag | acacagtggg | tcgcaggatc | tgacaagagt | ccaggtaagg | aacctgaggg | 720 |
| aaatctgagg | gtaccccag | cccataacac | agatgggtc | cccacagaaa | tctgccatga | 780 |
| ccctactgtc | actctggaga | acccagtcag | ggctgtccgc | tgagtctccc | tgtcttatac | 840 |
| aaggatcact | ggtctctggg | agggagaggt | gttggtctaa | gggagctgca | ctcgggtcag | 900 |
| cagagggagg | gtcccagacc | ctgccaggag | tcaaggtgag | gactgagggg | acaccattct | 960 |
| ccaaacgcac | aggactcagc | cccaccctac | cccttctgtc | agccacggga | attcatgggg | 1020 |
| aactgggggt | agatggactc | ccctcacttc | ctctttccat | gtctcctgga | ggtaggacct | 1080 |
| tggtttaagg | aagtggcctc | agatcaacaa | agggagggtc | ccaggtcgta | tcaggcatca | 1140 |
| agaagaggac | caagcaggct | cctcacccca | gtacacatgg | acccagctga | atatggccac | 1200 |
| ctcttgctgt | cttttctggg | aggacctctg | cagttgtggc | cagatgtggg | tcccctcatg | 1260 |
| tcttctattt | cgtatcaggg | atgtaagctt | ttgatctgag | agtttcttag | accagcaaag | 1320 |
| gagcagggtc | taggcttttc | caggagaaag | gtgagagccc | cacgtgagca | cagaggctcc | 1380 |
| ccacccagg | gtagtgggga | actcacagag | tccagcccac | cctcctgaca | cactgggag | 1440 |
| gctgggcctg | tgcttgcagc | ctgaaccctg | agggcccctc | aattcctctt | tcaggagctc | 1500 |
| cagggactgt | gaggtgaggc | cttggtctaa | ggcagtgttt | tcaggtcaca | gagcagaaag | 1560 |
| ggcccagaca | gtgccaggag | tcaaggtgag | gtgcatgccc | tgaatgtgta | ccaagggccc | 1620 |
| cacctgctcc | aggacaaagt | ggaccccact | gcatcagctc | cacctaccct | actgtcagtc | 1680 |
| ctggagcctt | ggcctctgcc | ggctgcatcc | tgaggagcca | tctctcactt | ccttcttcag | 1740 |
| gttctcaggg | gacagggaga | gcaagaggtc | aagagctgtg | ggacaccaca | gagcagcact | 1800 |
| gaaggagaag | acctgtaagt | tggcctttgt | tagaacctcc | agggtgtggt | tctcagctgt | 1860 |
| ggccacttac | accctccctc | tctccccagg | cctgtgggtc | ccatcgccc | aagtcctgcc | 1920 |
| cacactccca | cctgctaccc | tgatcagagt | catcatgcct | cgagctccaa | agcgtcagcg | 1980 |
| ctgcatgcct | gaagaagatc | ttcaatccca | aagtgagaca | cagggcctcg | agggtgcaca | 2040 |
| ggctcccctg | gctgtggagg | aggatgcttc | atcatccact | tccaccagct | cctcttttcc | 2100 |
| atcctctttt | ccctcctcct | cctcttcctc | ctcctcctcc | tgctatcctc | taataccaag | 2160 |
| cacccccagag | gaggtttctg | ctgatgatga | gacaccaaat | cctccccaga | gtgctcagat | 2220 |
| agcctgctcc | tccccctcgg | tcgttgcttc | ccttccatta | gatcaatctg | atgagggctc | 2280 |

-continued

| | |
|---|---|
| cagcagccaa aaggaggaga gtccaagcac cctacaggtc ctgccagaca gtgagtcttt | 2340 |
| acccagaagt gagatagatg aaaaggtgac tgatttggtg cagtttctgc tcttcaagta | 2400 |
| tcaaatgaag gagccgatca caaaggcaga aatactggag agtgtcataa aaaattatga | 2460 |
| agaccacttc cctttgttgt ttagtgaagc ctccgagtgc atgctgctgg tctttggcat | 2520 |
| tgatgtaaag gaagtggatc ccactggcca ctccttttgtc cttgtcacct ccctgggcct | 2580 |
| cacctatgat gggatgctga gtgatgtcca gagcatgccc aagactggca ttctcatact | 2640 |
| tatcctaagc ataatcttca tagagggcta ctgcaccccct gaggaggtca tctgggaagc | 2700 |
| actgaatatg atggggctgt atgatgggat ggagcacctc atttatgggg agcccaggaa | 2760 |
| gctgctcacc caagattggg tgcaggaaaa ctacctggag taccggcagg tgcctggcag | 2820 |
| tgatcctgca cggtatgagt ttctgtgggg tccaagggct catgctgaaa ttaggaagat | 2880 |
| gagtctcctg aaatttttgg ccaaggtaaa tgggagtgat ccaagatcct tcccactgtg | 2940 |
| gtatgaggag gctttgaaag atgaggaaga gagagcccag gacagaattg ccaccacaga | 3000 |
| tgatactact gccatggcca gtgcaagttc tagcgctaca ggtagcttct cctaccctga | 3060 |
| ataaagtaag acagattctt cactgtgttt taaaaggcaa gtcaaatacc acatgatttt | 3120 |
| actcatatgt ggaatctaaa aaaaaaaaaa aaaaagttg gtatcatgga agtagagagt | 3180 |
| agagcagtag ttacattaca attaaatagg aggaataagt tctagtgttc tattgcacag | 3240 |
| taggatgact atagttaaca ttaagatatt gtatattaca aaacagctag aaggaaggct | 3300 |
| tttcaatatt gtcaccaaaa agaaatgata aatgcatgag gtgatggata cactacctga | 3360 |
| tttgatcatt atactacata tacatgaatc agaacatcaa attgtacctc ataaatatct | 3420 |
| acaattacat gtcagttttt gtttatgttt ttgttttttt ttaatttatg aaaacaaatg | 3480 |
| agaatggaaa tcaatgatgt atgtggtgga | 3510 |

<210> SEQ ID NO 17
<211> LENGTH: 3672
<212> TYPE: DNA
<213> ORGANISM: Homo sapiens

<400> SEQUENCE: 17

| | |
|---|---|
| agtccaggat ctgccagtag tcaaggagag gaaaattgat gaagactgaa ggtaagaatg | 60 |
| taccctccca catgccaaag aaaaagggac ctcaccaatc cttgcttcct ctgttttcat | 120 |
| ccctcggagg cccaagttgg ggaggcatgt gccatgctca catttctgcc acgaggttgg | 180 |
| gggtggcacc ttgctcaggg aggtgagcac cgttgtttca agggggtgat gacaggtcag | 240 |
| caggtggagc cacacctgat cagcagaggg aggagtccca ggatctttag gactcaaggt | 300 |
| gtatgtgtcc ccttggtgag gactggagag cccacatccc ataatgaagg gatcccacag | 360 |
| agtctctctg tccccatgtc cttggctgtg tggggacctc atcacgggtg ccccaagtg | 420 |
| gcaaggtcac ttgtaccaca ggcagaaagt tgggaaacct tcagggagat gaggtcttgg | 480 |
| tgtaaaggga tatgtctgct catctcaggg gttgggagtc aaggaaggac aggccctggc | 540 |
| agaagtaaag atgaaaaacc cacaggagga ctttggaatc cccagaaccg aagggtccag | 600 |
| cctctgctgt cagccctgga caaccacatg atggggtgat gggacgtggg gccccttact | 660 |
| tctgttttgg aatcttgggc aggtgagcac tatgttctca gaggacgact tccagtcaac | 720 |
| agaaagagcc ccatatggtc cacaactaca gtggtcccag gatctgccaa gagtccaggt | 780 |
| gagaaacctg agggaggatt gagggttcct cctggccaga acacagaggg ctgcttagaa | 840 |
| atctgctctg cccctgctgt ctccccagag agcatgtgca ggactatgtg ctgagacccc | 900 |

```
tctcttatac tgggatcatt ggtctcaggg agcgggagac attggtctga gagggctgca      960
cttaggtcag cagtgggagg gtcccaggcc atgaccagaa tcaaggtggg ggctgacggg     1020
acagcactta ccaaaaacat gggactcagc ccttccctgc cccttctgtc agctatggga     1080
agtccctggg accatgggtg tttctatttc cctgatttcc tcttctgata tctcctggag     1140
gtagagcttt ggtttaagga gatggcgtca ggtcaacaga gggagggtcc caggccaaga     1200
taggcatcaa gatgggaacc aaacaggctc cttacccgag gacacatgga ccctgctgac     1260
tgtcaccatc tcttgctgtc cttcctgggt agccctgtgt acatgtggcc agatgtgtat     1320
ccccacatgt cctctttcat atcaggaaag agctattgat ctgagagttt ctcaggtcag     1380
gagagctgtg tcttccaggc cctggcagga gaaaggtgag ggccctgagc acagagggga     1440
ccatccactc caaaaagtg agaaactcac agagtttggc acctttct gacagtgctg        1500
gggtgccagg atgggtgctt gcagtctgca gcctgatggc cccatgattc ctcttctaga     1560
agctccaaaa actgagcagt gaggccttgg tctcaagcaa tgtcttcaga tctcagaaca     1620
caggaagcct aggcagtgcc agtagtcaag atgagatgtt cacccttaat ctacaaatgg     1680
ccccacctgc cccagtacag aaagggaccc ccagcttgca acctcacctg ccctacctca     1740
gtcctggagc ctcctgctct gatgtccagc tgcatcttga gcagccttct cacttccttt     1800
ttcaggtttt tagagaacag gccaacctgg aggacaggag tcccaggaga acccaggaga    1860
tcactggagg agaacaagtg taagtaggcc tttgttagat tctccatggt tcatatctca     1920
tctgagtctg ttctcacgct ccctctctcc ccaggctgtg gggcccatc acccagatat      1980
ttcccacagt tcggcctgct gacctaacca gagtcatcat gcctcttgag caaagaagtc     2040
agcactgcaa gcctgaggaa ggccttcagg cccaagaaga agacctgggc ctggtgggtg     2100
cacaggctct ccaagctgag gagcaggagg ctgccttctt ctcctctact ctgaatgtgg     2160
gcactctaga ggagttgcct gctgctgagt caccaagtcc tccccagagt cctcaggaag     2220
agtccttctc tcccactgcc atggatgcca tctttgggag cctatctgat gagggctctg     2280
gcagccaaga aaaggagggg ccaagtacct cgcctgacct gatagaccct gagtccttt     2340
cccaagatat actacatgac aagataattg atttggttca tttattgctc cgcaagtatc     2400
gagtcaaggg gctgatcaca aaggcagaaa tgctgggag tgtcatcaaa aattatgagg      2460
actactttcc tgagatattt agggaagcct ctgtatgcat gcaactgctc tttggcattg     2520
atgtgaagga agtggacccc actagccact cctatgtcct tgtcacctcc ctcaacctct     2580
cttatgatgg catacagtgt aatgagcaga gcatgcccaa gtctggcctc ctgataatag     2640
tcctgggtgt aatcttcatg gagggaact gcatccctga agaggttatg tgggaagtcc      2700
tgagcattat gggggtgtat gctggaaggg agcacttcct ctttggggag cccaagaggc     2760
tccttaccca aaattgggtg caggaaaagt acctggtgta ccggcaggtg cccggcactg     2820
atcctgcatg ctatgagttc ctgtggggtc caagggccca cgctgagacc agcaagatga     2880
aagttcttga gtacatagcc aatgccaatg ggagggatcc cacttcttac ccatcctgt      2940
atgaagatgc tttgagagag gagggagagg gagtctgagc atgagatgca accagggcca     3000
gcgggcaggg aaatgggcca atgcatgctt cagggccaca cccagcagtt tccctgtcct     3060
gtgtgaaatc aggcccattc ttccctctgt gtttgatgag agaagtcagt gttctcagta     3120
gtagaaggca cagtgaatgg aagggaacac attgtatact gcctttaggt ttctcttcca     3180
tcgggtgact tggagatttg ttttgtttc cctttggtaa ttttcaaata ttgttcctgt      3240
```

-continued

```
aataaaagtt ttagttagct tcaacatcta agtgtatgga tgatactgac cacacatgtt      3300
gttttgctta tccatttcaa gtgcaagtgt ttgccatttt gtaaaacatt ttgggaaatc      3360
ttccatcttg ctgtgatttg caataggtat tttcttggag aatgtaagaa cttaacaata      3420
aagctgaact ggtgttgtga acagagaaa taaaaggaga aggtcattaa ttcttgtctt       3480
cttatccata ttaatctgtt gttctatgaa agtacacacc catacacaca tgtacacccc      3540
cctcccccca catacatatt caccaaggaa atgcagtttc ctactgagtt gcagattctc      3600
tgagatgtcc tggacaataa aaatattcc aaagtagaga gtggtagcac cgtggggtca       3660
cagtaatact ag                                                          3672
```

<210> SEQ ID NO 18
<211> LENGTH: 1022
<212> TYPE: DNA
<213> ORGANISM: Homo sapiens

<400> SEQUENCE: 18

```
gcctgtgggt ccccattgcc cagcttttgc ctgcactctt gcctgctgcc ctgagcagag        60
tcatcatgtc ttctgagcag aagagtcagc actgcaagcc tgaggaaggc gttgaggccc       120
aagaagaggc cctgggcctg gtgggtgcgc aggctcctac tactgaggag caggaggctg       180
ctgtctcctc ctcctctcct ctggtccctg gcaccctgga ggaagtgcct gctgctgagt       240
cagcaggtcc tccccagagt cctcaggag cctctgcctt acccactacc atcagcttca        300
cttgctggag caacccaat gagggttcca gcagccaaga agaggagggg ccaagcacct        360
cgcctgacgc agagtccttg ttccgagaag cactcagtaa caaggtggat gagttggctc       420
attttctgct ccgcaagtat cgagccaagg agctggtcac aaaggcagaa atgctggaga       480
gagtcatcaa aaattacaag cgctgctttc ctgtgatctt cggcaaagcc tccgagtccc      540
tgaagatgat ctttggcatt gacgtgaagg aagtggaccc caccagcaac acctacaccc       600
ttgtcacctg cctgggcctt tcctatgatg gcctgctggg taataatcag atctttccca       660
agacaggcct tctgataatc gtcctgggca caattgcaat ggaggcgac agcgcctctg        720 aggaggaaat ctgggaggag ctgggtgtga tgggggtgta tgatgggagg gagcacactg       780
tctatgggga gccaggaaa ctgctcaccc aagattgggt gcaggaaaac tacctggagt        840
accggcaggt accggcagt aatcctgcgc gctatgagtt cctgtggggt ccaagggctc        900
tggctgaaac cagctatgtg aaagtcctgg agcatgtggt cagggtcaat gcaagagttc       960
gcattgccta cccatccctg cgtgaagcag ctttgttaga ggaggaagag ggagtctgag      1020
ca                                                                    1022
```

<210> SEQ ID NO 19
<211> LENGTH: 1866
<212> TYPE: DNA
<213> ORGANISM: Homo sapiens

<400> SEQUENCE: 19

```
gagtgttgca actgggcctg gcatgtttca gcgtggtgtc cagcagtgtc tcccactcct        60
tgtgaagtct gaggttgcaa aaggactgtg atcatatgaa gatcatccag gagtacaact       120
cgaaattctc agaaaacagg accttgatgt gagaggagca ggttcaggta acaaagggc        180 gaggacccga gcgagcttaa ggccagtggg gtgcagcgtc tggtcagccg agggtgaatt      240
ctcaggactg gtcgggagtc aaggtgccac atctcctgcc tttctgctca ctttcctgcc       300
tgttttgcct gaccacagcc atcatgcctc ggggtcagaa gagtaagctc cgtgctcgtg      360
```

```
agaaacgccg caaggcgcga gaggagaccc agggtctcaa ggttcgtcac gccactgcag    420
cagagaaaga ggagtgcccc tcctcctctc ctgttttagg ggatactccc acaagctccc    480
ctgctgctgg cattccccag aagcctcagg gagctccacc caccaccact gctgctgcag    540
ctgtgtcatg taccgaatct gacgaaggtg ccaaatgcca aggtgaggaa aatgcaagtt    600
tctcccaggc cacaacatcc actgagagct cagtcaaaga tcctgtagcc tgggaggcag    660
gaatgctgat gcacttcatt ctacgtaagt ataaaatgag agagcccatt atgaaggcag    720
atatgctgaa ggttgttgat gaaaagtaca aggatcactt cactgagatc ctcaatggag    780
cctctcgccg cttggagctc gtctttggcc ttgatttgaa ggaagacaac cctagtagcc    840
acacctacac cctcgtcagt aagctaaacc tcaccaatga tggaaacctg agcaatgatt    900
gggactttcc caggaatggg cttctgatgc ctctcctggg tgtgatcttc ttaaagggca    960
actctgccac cgaggaagag atctggaaat tcatgaatgt gttgggagcc tatgatggag    1020
aggagcactt aatctatggg gaacccgta agttcatcac ccaagatctg gtgcaggaaa    1080
aatatctgaa gtacgagcag gtgcccaaca gtgatccccc acgctatcaa ttcctatggg    1140
gtccgagagc ctatgctgaa accaccaaga tgaaagtcct cgagtttttg gccaagatga    1200
atggtgccac tccccgtgac ttcccatccc attatgaaga ggctttgaga gatgaggaag    1260
agagagccca agtccgatcc agtgttagag ccaggcgtcg cactactgcc acgactttta    1320
gagcgcgttc tagagcccca ttcagcaggt cctcccaccc catgtgagaa ctcaggcaga    1380
ttgttcactt tgtttttgtg gcaagatgcc aaccttttga agtagtgagc agccaagata    1440
tggctagaga gatcatcata tatatctcct ttgtgttcct gttaaacatt agtatctttc    1500
aagtgttttt cttttaatag aatgtttatt tagagttggg atctatgtct atgagcgaca    1560
tggatcacac atttattggt gctgccagct ttaagcataa gagttttgat attctatatt    1620

tttcaaatcc ttgaatcttt tttgggttga agaagaagaa agcatagctt tagaatagag    1680

attttctcag aaatgtgtga agaacctcac acaacataat tggagtctta aaatagagga    1740
agagtaagca aagcatgtca gttttttgtt ttctgcattc agttttgttt ttgtaaaatc    1800
caaagataca tacctggttg tttttagcct tttcaagaat gcagataaaa taaatagtaa    1860

таааттт                                                              1866

<210> SEQ ID NO 20
<211> LENGTH: 1004
<212> TYPE: DNA
<213> ORGANISM: Homo sapiens

<400> SEQUENCE: 20
cgccaattta gggtctccgg tatctcccgc tgagctgctc tgttcccggc ttagaggacc     60
aggagaaggg ggagctggag gctggagcct gtaacaccgt ggctcgtctc actctggatg    120
gtggtggcaa cagagatggc agcgcagctg gagtgttagg agggcggcct gagcggtagg    180
agtggggctg gagcagtaag atggcggcca gagcggtttt tctggcattg tctgcccagc    240
tgctccaagc caggctgatg aaggaggagt cccctgtggt gagctggagg ttggagcctg    300
aagacggcac agctctgtgc ttcatcttct gaggttgtgg cagccacggt gatggagacg    360
gcagctcaac aggagcaata ggaggagatg gagtttcact gtgtcagcca ggatggtctc    420
gatctcctga cctcgtgatc cgcccgcctt ggccttccaa agtgccgaga ttacagcgat    480
gtgcattttg taagcacttt ggagccacta tcaaatgctg tgaagagaaa tgtacccaga    540
```

```
tgtatcatta tccttgtgct gcaggagccg gctcctttca ggatttcagt cacatcttcc    600
tgctttgtcc agaacacatt gaccaagctc ctgaaagatg taagtttact acgcatagac    660
ttttaaactt caaccaatgt atttactgaa ataacaaat gttgtaaatt ccctgagtgt    720
tattctactt gtattaaaag gtaataatac ataatcatta aaatctgagg gatcattgcc    780
agagattgtt ggggagggaa atgttatcaa cggtttcatt gaaattaaat ccaaaaagtt    840
atttcctcag aaaaatcaaa taaagtttgc atgttttta ttcttaaaac attttaaaaa    900
ccactgtaga atgatgtaaa tagggactgt gcagtatttc tgacatatac tataaaatta    960
ttaaaaagtc aatcagtatt caacatcttt tacactaaaa agcc                    1004

<210> SEQ ID NO 21
<211> LENGTH: 1424
<212> TYPE: DNA
<213> ORGANISM: Homo sapiens

<400> SEQUENCE: 21
attgctgtga aaagaccgag ggaaaaacag aaccaagctt gcagctaaat ctagttgagc     60
catctccttc attctcaaca cctggccttg tggttgggtg atgctctgtg atggcagaag    120
gtaaggacgc cctggggccc agttatcttt tctcacttaa tgtgccctg ggggctgaaa    180 cagaacaggc ttttatgtgg gtagagagga cacagcttcg tcaagcccag acctggaccc    240
tgcccatcaa caacctgcag tgctccagca gtgtgaagta cacccactgt gatggtacgt    300
gccgaggcat ttctgtgagc agttatttca ttttggacc caggaaatca gcaccactga    360
actgcagctt gtccccttg tcatcgtggc ttccagctgc tgtggttgct ctgaggactg    420
agagcaagtt gttgctgcca tctatggtct gtcttggggg aagcacatgg tttgcctgct    480
ggagagggaa gcagctgcct tgcagattca gcaacacagc accctctctc ccctctgagg    540
ggaaaatcaa caccaagatg ttggtgtccc cagtgtaaac cccattatga aaacctgtgt    600
ttactgacct accatcattt taaagcagtt ccgtttgaac tgcaatcaaa cctccaagtg    660
acctttctgt ccctccgccc agcattcctg aaagggcctg ttgtttcttt ggttcaatga    720
agaaaccttc tgtgtagtta agcaagtgtt tttccagtca tgtctcctgg tgagttacag    780
aaggattatt gttgggtctt ggtggtggtg gtggttgttt ttcttttaat actccatcct    840
ccctaccccg tgataccct agacactaat ttttagttc cttggtggag gagagcatag    900
tgagttgagc agctttgtgg gactttaaaa gttcgtagtt tttcagatcc tggtgtaagc    960
tgaattctct ctgccccacc ccccagggcc tgggagcctt ccaaagtgag gtgtccacac   1020
gggaatgggc cacagaatcg ccgcctgcaa gctaggaatg cccgtcctgc ctgatggtcc   1080
tgcctgatgt gttcatacgc tgtgtggttt tctgtcttac agttgtttgt tggacttggg   1140
ttcccttacg agggcccagc tcccctggaa gctatcgcaa atggatgtgc ttttctgaat   1200
cccaagttca acccacccaa aagcagcaaa aacacagact ttttcattgg caagccaact   1260
ctgagagagg taagcatcta tcaaaattat tccattttga ataatatgaa taatagctat   1320
ttattgagtg ctcatgtagg tattaacctt tccatctaac atgattgggg gggagggtga   1380
gggtatagag gctcagagag gcaaatgacc tgatcctcga gctc                   1424

<210> SEQ ID NO 22
<211> LENGTH: 809
<212> TYPE: DNA
<213> ORGANISM: Homo sapiens

<400> SEQUENCE: 22
```

```
agcggcgagg gctggatcct gggccaaata tatgccaaca acgacaagct ctccaagagg      60
ctgaagaaag tgtggaagcc acagctgttt gagcgagagt tctacagtga gatcctggac     120
aagaagttca cagtgactgt gaccatgcgg accctggacc tcatcgatga ggcttacggg     180
ctcgactttt acatcctcaa gaccccgaag gaggacctgt gctccaagtt tgggatggag     240
ctgaagcgag ggatgctgct gcggcttgcc cggcaggacc cccagctgca ccccgaggac     300
cccgagcggc gggcagccat ctacgacaag tacaaggaat tgccatccc agaggaggag      360 gcagagtggg tgggcctcac gctggaggag gccattgaga agcagagact tttggaggag     420
aaggaccctg taccctgtt caagatctat gtggcggagc tgatccagca gctgcagcag      480
caggcactgt cagagccggc ggtggtgcag aagacagcca gtggccagtg accacacagc     540
tcctccatgc ctgaccaaca ggcccagctt tccctgccag gccctttgca ctgaggacac     600 agatcccgg gagctgtgag gccaccggt gggcagtggg tggatcctgg tttcgtgtgc       660
tgcccatgca ccttccagcc cggggccagc ttggcaggga tccccaggag gcctgggccg     720
cccagaggct cctctcaggc tgggccccga cgtttgcggc agtgttcctt gtcccgtggg     780
gccgggagcg agtaaagtct gggccaggc                                        809

<210> SEQ ID NO 23
<211> LENGTH: 1821
<212> TYPE: DNA
<213> ORGANISM: Homo sapiens

<400> SEQUENCE: 23
actagtttga ttttatgtca gtttggaagc tgaagatcca aacgaggcat tctgtgagat      60
ctatggagag attggtacaa acactgaata catgtaaatt atactcaggg tagaccctat     120
ttgtggttaa aatagggata tttccttttt tttttttttt ttttgactg tttcttaatc      180 agtgccatgc caggaaaata gggatgtttc cttcccagag atctgtgtgt cttttttcag     240
aaacgtctgt gacaggccca tcaattttga aatatttggt ttttgagcct gtcactctaa     300
accagcgttt aacgttcaaa aggcaaataa ctgatgacca ggcggcacat tgttctgctc     360
cgtgagtgtc tggcactggg aaaggtgtag attgtctaga atgacagcaa ttccgacgcc     420
ccagtcagtc ctgcgtgatt gtggcgaggg cgcgtctggc accgggaagg tgtagatcat     480
ctagaatgac ggcgattccg acgccccggt cagtcctgcg tgattggcga gggtgcatct     540
gtcgtgagaa ttcccagttc tgaagagagc aaggagactg atcccgcgta gtccaaggca     600
ttggctcccc tgttgctctt ccttgtggag ctcccccctgc ccactccct cctgcctgca     660 tcttcagagc tgcctctgaa gctcgcttgg tccctagctc acacttccc tgcggctggg      720 aaggtaattg aatactcgag tttaaaagga agcacatcc ttttaaacca aaacacacct      780
gctgggctgt aaacagcttt tagtgacatt accatctact ctgaaaatct aacaaggag      840 tgatttgtgc agttgaaagt aggatttgct tcataaaagt cacaatttga attcatttttt    900 gcttttaaat ccagccaacc ttttctgtct taaaaggaaa aaaaaaaaaa aaccattcac     960
cagggttctt gctgcctgta acctcaggca gatgaattcc tagttggctg tgacttttgg    1020
tttaagtgga aggttgagga ggaaaatgaa ataattctt ttgttatcta aaggaaaaca     1080
tgtttgaaaa tgtcttggcg gcgttggctg gtggtgtgta acgtcgattt tgtctctgca    1140
gaattaaggt gaaaagcact gaagttgaga tcctagagaa gtctcaaatt gaagccattg    1200
cttcctcgtt agggaacgcg aatcccctga gctgaaggag aaggaaaaat ggatccgctt    1260
```

-continued

| | |
|---|---|
| tcttaaacct tccagaatt tgccctaga accactccta ttcttgacgc ccagaatggt | 1320 |
| cagtgcctca cagaatgagg ttcctgcggc gcacccctgg aagaactggc ctacagacgg | 1380 |
| tcttcgcgtg gctctggacg ttctgagcga gggctcgatt tggagtcaag aaagctctgc | 1440 |
| agggacaggt agagctgacc ggtctctgcg agggaagccc atggagcatg tctcctcgcc | 1500 |
| ctgtgattcg aactcctcat ctcttccccg cggagacgtg ttgggcagtt ccagacctca | 1560 |
| caggaggagg ccatgtgtgc aacaaagcct gtcaagttcg ttcacttgtg aaaaggaccc | 1620 |
| cgagtgcaaa gtggaccaca agaagggggct caggaaaagt gaaaacccaa gaggcccgtt | 1680 |
| ggtcctccca gctggaggtg gtgcccaaga tgagagtggg tccagaatcc accacaaaaa | 1740 |
| ttggactctt gcaagtaaga ggggaagaaa ctcagcgcag aaggctagct tgtgcctgaa | 1800 |
| tggatcttcc ctttcagagg a | 1821 |

<210> SEQ ID NO 24
<211> LENGTH: 1316
<212> TYPE: DNA
<213> ORGANISM: Homo sapiens

<400> SEQUENCE: 24

| | |
|---|---|
| gcggtggcgg aggcggacac attggcgtga gacctgggag tacgttgtgc caaatcattg | 60 |
| ccacttgcca catgagtgta aatgatggcg gatgcaagta tgtcctctgc cgatgggaaa | 120 |
| agcgattatg gcctgcgaag gttttggccc gaaccgcgac ttcaacaaaa aataagagaa | 180 |
| gaaaggaata ttttctagct gtgcaaatcc tctccctaga ggaaaaaatt aaggtgaaaa | 240 |
| gcactgaagt tgagatccta gagaagtctc aaattgaagc cattgcttcc tcgttagcct | 300 |
| cacagaatga ggttcctgcg gcaccccctgg aagaactggc ctacagacgg tcgcttcgcg | 360 |
| tggctctgga cgttctgagc gagggctcga tttggagtca agaaagctct gcagggacag | 420 |
| gtagagctga ccggtctctg cgagggaagc ccatggagca tgtctcctcg ccctgtgatt | 480 |
| cgaactcctc atctcttccc cgcggagacg tgttgggcag ttccagacct cacaggagga | 540 |
| ggccatgtgt gcaacaaagc ctgtcaagtt cgttcacttg tgaaaaggac cccgagtgca | 600 |
| aagtggacca caagaagggg ctcaggaaaa gtgaaaaccc aagaggcccg ttggtcctcc | 660 |
| cagctggagg tggtgcccaa gatgagagtg ggtccagaat ccaccacaaa aattggactc | 720 |
| ttgcaagtaa gaggggaaga aactcagcgc agaaggctag cttgtgcctg aatggatctt | 780 |
| ccctttcaga ggacgacacg gagagagaca tggggagcaa aggaggcagc tgggcagccc | 840 |
| cgtccttgcc ctccggggtc aggaggacg atccctgtgc caacgctgag ggacacgacc | 900 |
| ccggtctgcc gttgggcagc ctcactgcgc ccccagcccc tgagccctcg gcctgctcag | 960 |
| agcctggaga atgccctgcg aaaaagaggc cgcgcctgga tggcagccaa aggccgcctg | 1020 |
| ccgtgcagct ggagcccatg gcagcagggg ccgcaccatc cccgggccg gggccagggc | 1080 |
| ccagagagtc tgtgacccccg cgcagcaccg ccaggctggg cccgcctccc tcccacgcct | 1140 |
| ctgcggatgc aaccagatgt cttccttgcc cggattccca gaagctggag aaagagtgcc | 1200 |
| agtcttccga agagtccatg gggtctaatt ccatgcgttc tatcctggag gaagacgagg | 1260 |
| aagacgagga gccaccaaga gtcctttat accacgaacc acgttcgttt gaagta | 1316 |

<210> SEQ ID NO 25
<211> LENGTH: 1896
<212> TYPE: DNA
<213> ORGANISM: Homo sapiens

<400> SEQUENCE: 25

```
gcggcggtgg cggaggcgga cacattggcg tgagacctgg gagtacgttg tgccaaatca      60
ttgccacttg ccacatgagt gtaaatgatg gcggatgcaa gtatgtcctc tgccgatggg     120
aaaagcgatt atggcctgcg aaggtgacag ccattattct gtaacttcag gacttagaaa     180
tgactttcgg gtgacaagta aaatcttgat caggagatac ctaggatttg cttcagtgaa     240
ataattgagc cagaacacgg ttggcactga ttctcgttcc ccatttaatg gggttttggt     300
ctagtgcttc caaggttaca cttccagaaa tgtcttttt ttttcacact aaaaaaaaaa     360
aaaagaatca gctgtaaaaa ggcatgtaag gctgtaactc aaggaaagat ctggcaagca     420
gccctgtgat agtaaattat ggtcgtgttc agggaatgct ttccagcaat tcagtagaca     480
gtgctcagct gcaatgcaaa agcccaggtc cttgtctttg tctgccactg gcctctcatg     540
cctcagtttc cccatctgtg aaacaatggg gattggacca atatctgaa atcccatggt     600
tataggcctt caggattacc tgctgcattt gtgctaaagt ttgccactgt ttctcactgt     660
cagctgttgt aataacaagg attttctttt gttttaaatg taggttttgg cccgaaccgc     720
gacttcaaca aaaaataaga gaagaaagga atatttcta gctgtgcaaa tcctctccct     780
agaggaaaag ttaattgttg tgttgttta atactgtttt ttcccgtgta gatttctgat     840
acttcaatcc cctactcccc caaaacagtt gaagcccagc ccactcttaa tgggcttatt     900
caccatttgt gtaattcatt aatgctcata ataacctcat gagaaagcaa ctagtttgat     960
tttatgtcag tttggaagct gaagatccaa acgaggcatt ctgtgagatc tatggagaga    1020
ttggtacaaa cactgaatac atgtaaatta tactcagggt agaccctatt tgtggttaaa    1080
atagggatat ttccttttt tttttttttt ttttgactgt ttcttaatca gtgccatgcc    1140
aggaaaatag ggatgtttcc ttcccagaga tctgtgtgtc ttttttcaga aacgtctgtg    1200
acaggcccat caattttgaa atatttggtt tttgagcctg tcactctaaa ccagcgttta    1260
acgttcaaaa ggcaaataac tgatgaccag gcggcacatt gttctgctcc gtgagtgtct    1320
ggcactggga aagtgtagaa ttgtctagaa tgacagcaat tccgacgccc cagtcagtcc    1380
tgcgtgattg tggcgagggc gcgtctggca ccgggaaggt gtagatcatc tagaatgacg    1440
gcgattccga cgcccggtc agtcctgcgt gattggcgag ggtgcatctg tcgtgagaat    1500
tcccagttct gaagagagca aggagactga tcccgcgtag tccaaggcat ggctcccct    1560
gttgctcttc cttgtggagc tccccctgcc ccactccctc ctgcctgcat cttcagagct    1620
gcctctgaag ctcgcttggt ccctagctca cactttccct cgcggctggga aggtaattga    1680
atactcgagt ttaaaaggaa agcacatcct tttaaaccaa aacacacctg ctgggctgta    1740
aacagctttt agtgacatta ccatctactc tgaaaatcta acaaaggagt gatttgtgca    1800
gttgaaagta ggatttgctt cataaaagtc acaatttgaa ttcattttg cttttaaatc    1860
cagccaacct tttctgtctt aaaaggaaaa aaaaaa                              1896
```

<210> SEQ ID NO 26
<211> LENGTH: 4473
<212> TYPE: DNA
<213> ORGANISM: Homo sapiens

<400> SEQUENCE: 26

```
aaggggaggt aaccctggcc cctttggtcg ggccccggg cagccgcgcg cccccttccca     60
cggggccctt tactgcgccg cgcgccggc ccccaccct cgcagcaccc cgcgccccgc    120
gccctcccag ccgggtccag ccggagccat ggggccggag ccgcagtgag caccatggag    180
```

-continued

| | |
|---|---|
| ctggcggcct tgtgccgctg ggggctcctc ctcgccctct tgcccccgg agccgcgagc | 240 |
| acccaagtgt gcaccggcac agacatgaag ctgcggctcc ctgccagtcc cgagacccac | 300 |
| ctggacatgc tccgccacct ctaccagggc tgccaggtgg tgcagggaaa cctggaactc | 360 |
| acctacctgc ccaccaatgc cagcctgtcc ttcctgcagg atatccagga ggtgcagggc | 420 |
| tacgtgctca tcgctcacaa ccaagtgagg caggtcccac tgcagaggct gcggattgtg | 480 |
| cgaggcaccc agctctttga ggacaactat gccctggccg tgctagacaa tggagacccg | 540 |
| ctgaacaata ccacccctgt cacagggcc tccccaggag cctgcggga gctgcagctt | 600 |
| cgaagcctca cagagatctt gaaggaggg gtcttgatcc agcggaaccc ccagctctgc | 660 |
| taccaggaca cgattttgtg gaaggacatc ttccacaaga caaccagct ggctctcaca | 720 |
| ctgatagaca ccaaccgctc tcgggcctgc caccctgtt ctccgatgtg taagggctcc | 780 |
| cgctgctggg gagagagttc tgaggattgt cagagcctga cgcgcactgt ctgtgccggt | 840 |
| ggctgtgccc gctgcaaggg gccactgccc actgactgct gccatgagca gtgtgctgcc | 900 |
| ggctgcacgg gccccaagca ctctgactgc ctggcctgcc tccacttcaa ccacagtggc | 960 |
| atctgtgagc tgcactgccc agccctggtc acctacaaca cagacacgtt tgagtccatg | 1020 |
| cccaatcccg agggccggta cattcggc gccagctgtg tgactgcctg tccctacaac | 1080 |
| tacctttcta cggacgtggg atcctgcacc ctcgtctgcc cctgcacaa ccaagaggtg | 1140 |
| acagcagagg atggaacaca gcggtgtgag aagtgcagca gccctgtgc ccgagtgtgc | 1200 |
| tatggtctgg gcatggagca cttgcgagag gtgagggcag ttaccagtgc caatatccag | 1260 |
| gagtttgctg gctgcaagaa gatctttggg agcctggcat ttctgccgga gagctttgat | 1320 |
| ggggacccag cctccaacac tgccccgctc agccagagc agctccaagt gtttgagact | 1380 |
| ctggaagaga tcacaggtta cctatacatc tcagcatggc cggacagcct gcctgacctc | 1440 |
| agcgtcttcc agaacctgca gtaatccgg ggacgaattc tgcacaatgg cgcctactcg | 1500 |
| ctgaccctgc aagggctggg catcagctgg ctggggctgc gctcactgag ggaactgggc | 1560 |
| agtggactgg ccctcatcca ccataacacc cacctctgct tcgtgcacac ggtgccctgg | 1620 |
| gaccagctct ttcggaaccc gcaccaagct ctgctccaca ctgccaaccg ccagaggac | 1680 |
| gagtgtgtgg gcgagggcct ggcctgccac cagctgtgcg cccagggca ctgctggggt | 1740 |
| ccagggccca cccagtgtgt caactgcagc cagttccttc ggggccagga gtgcgtggag | 1800 |
| gaatgccgag tactgcaggg gctccccagg gagtatgtga atgccaggca ctgtttgccg | 1860 |
| tgccacccctg agtgtcagcc ccagaatggc tcagtgacct gttttggacc ggaggctgac | 1920 |
| cagtgtgtg cctgtgccca ctataaggac cctcccttct gcgtggcccg ctgccccagc | 1980 |
| ggtgtgaaac ctgacctctc ctacatgccc atctggaagt ttccagatga ggagggcgca | 2040 |
| tgccagcctt gccccatcaa ctgcacccac tcctgtgtgg acctggatga caaggcctgc | 2100 |
| cccgccgagc agagagccag ccctctgacg tccatcatct ctgcggtggt ggcattctg | 2160 |
| ctggtcgtgg tcttgggggt ggtctttggg atcctcatca agcgacgca gcagaagatc | 2220 |
| cggaagtaca cgatgcggag actgctgcag gaaacggagc tggtggagcc gctgacacct | 2280 |
| agcggagcga tgcccaacca ggcgcagatg cggatcctga agagacgga gctgaggaag | 2340 |
| gtgaaggtgc ttggatctgg cgcttttggc acagtctaca agggcatctg gatccctgat | 2400 |
| ggggagaatg tgaaaattcc agtggccatc aaagtgttga gggaaaacac atccccaaa | 2460 |
| gccaacaaag aaatcttaga cgaagcatac gtgatggctg tgtgggctc cccatatgtc | 2520 |
| tcccgccttc tgggcatctg cctgacatcc acggtgcagc tggtgacaca gcttatgccc | 2580 |

```
tatggctgcc tcttagacca tgtccgggaa aaccgcggac gcctgggctc ccaggacctg      2640
ctgaactggt gtatgcagat tgccaagggg atgagctacc tggaggatgt gcggctcgta      2700
cacagggact tggccgctcg gaacgtgctg gtcaagagtc ccaaccatgt caaaattaca      2760
gacttcgggc tggctcggct gctggacatt gacgagacag agtaccatgc agatgggggc      2820
aaggtgccca tcaagtggat ggcgctggag tccattctcc gccggcggtt cacccaccag      2880
agtgatgtgt ggagttatgg tgtgactgtg tgggagctga tgacttttgg ggccaaacct      2940
tacgatggga tcccagcccg ggagatccct gacctgctgg aaaagggggga gcggctgccc      3000 cagccccca tctgcaccat tgatgtctac atgatcatgg tcaaatgttg gatgattgac      3060
tctgaatgtc ggccaagatt ccgggagttg gtgtctgaat ctcccgcat ggccagggac      3120 ccccagcgct tgtggtcat ccagaatgag gacttgggcc cagccagtcc cttggacagc      3180
accttctacc gctcactgct ggaggacgat gacatggggg acctggtgga tgctgaggag      3240
tatctggtac cccagcaggg cttcttctgt ccagaccctg cccgggcgc tgggggcatg      3300 gtccaccaca gcaccgcag ctcatctacc aggagtggcg gtgggaccct gacactaggg      3360
ctggagccct ctgaagagga ggcccccagg tctccactgg caccctccga agggctggc      3420 tccgatgtat tgatggtga cctgggaatg ggggcagcca aggggctgca aagcctcccc      3480
acacatgacc ccagccctct acagcggtac agtgaggacc ccacagtacc cctgccctct      3540
gagactgatg gctacgttgc cccctgacc tgcagcccc agcctgaata tgtgaaccag      3600
ccagatgttc ggccccagcc cccttcgccc cgagagggcc ctctgcctgc tgcccgacct      3660
gctggtgcca ctctggaaag gcccaagact ctctccccag ggaagaatgg ggtcgtcaaa      3720
gacgtttttg cctttggggg tgccgtggag aaccccgagt acttgacacc ccaggagga      3780 gctgcccctc agccccaccc tcctcctgcc ttcagcccag ccttcgacaa cctctattac      3840
tgggaccagg acccaccaga gcgggggggct ccacccagca ccttcaaagg gacacctacg      3900
gcagagaacc cagagtacct gggtctggac gtgccagtgt gaaccagaag gccaagtccg      3960
cagaagccct gatgtgtcct cagggagcag ggaaggcctg acttctgctg gcatcaagag      4020
gtgggagggc cctccgacca cttccagggg aacctgccat gccaggaacc tgtcctaagg      4080
aaccttcctt cctgcttgag ttcccagatg gctggaaggg gtccagcctc gttggaagag      4140
gaacagcact ggggagtctt tgtggattct gaggccctgc ccaatgagac tctagggtcc      4200
agtggatgcc acagcccagc ttggcccttt ccttccagat cctgggtact gaaagccta      4260 gggaagctgg cctgagaggg gaagcggccc taagggagtg tctaagaaca aaagcgaccc      4320
attcagagac tgtccctgaa acctagtact gcccccatg aggaaggaac agcaatggtg      4380
tcagtatcca ggctttgtac agagtgcttt tctgtttagt ttttactttt tttgttttgt      4440 tttttttaaag atgaaataaa gacccagggg gag                                 4473
```

<210> SEQ ID NO 27
<211> LENGTH: 4233
<212> TYPE: DNA
<213> ORGANISM: Homo sapiens

<400> SEQUENCE: 27

```
ccctcctccc agtcgaagca cctcctgtcc gcccctcagc gcatgggtgg cggtcacgtg        60
cccagaacgt ccggcgttcg ccccgccctc ccagtttccg cgcgcctctt tggcagctgg       120
tcacatggtg agggtggggg tgagggggcc tctctagctt gcggcctgtg tctatggtcg       180
```

```
ggccctctgc gtccagctgc tccggaccga gctcggtgt atgggccgt aggaaccggc     240
tccggggccc cgataacggg ccgcccccac agcacccgg gctggcgtga ggtaagtgca    300
gtcccttccc aggaatgaga accagtgccc gcccccctca cagctttcca cgcgttcgtt   360
tcgcgagctg gttatggaag ggtcgctcaa gggcgggaag tggggccttt gtggtcatgg   420
gaaagtataa ttttagggac tgaggtgtag gatcttcgat gcaaggcatg tgtcatgtgt   480
gatctttgtg cggggcgcga ttgtcccaaa ggaaaaagcg ttttctattg cagggcctca   540
cgtggctgga ggggttggta ttgagtcatt gtgttatctc tggggccggc cccaaggaag   600
actgggagcg ggggatggga tgctggtggt gttctttgcg cttttttttt gggagtccct   660
ttgttgctgc aggtcatacc atcctaactc tgtaagcgac ttttggtgat aggagtctgt   720
gattgtaggg tctcccttga tctgagaatg gctacctctc gatatgagcc agtggctgaa   780
attggtgtcg gtgcctatgg gacagtgtac aaggcccgtg atccccacag tggccacttt   840
gtggccctca agagtgtgag agtccccaat ggaggaggag gtggaggagg ccttcccatc   900
agcacagttc gtgaggtggc tttactgagg cgactggagg cttttgagca tcccaatgtt   960
gtccggtgag aaggtggtgg agggttgggc gtggggagta aagggaaaag acagcctata  1020
ggtggggtgt gatgatctgt agagaagtgg ggaccctgag gaaataatga gaggccatgt  1080
tgggttaaag gggattgaaa agtgagcatt tactctggtc aggctgatgg acgtctgtgc  1140
cacatcccga actgaccggg agatcaaggt aaccctggtg tttgagcatg tagaccagga  1200
cctaaggaca tatctggaca aggcaccccc accaggcttg ccagccgaaa cgatcaaggt  1260
gagtgggggtt ggtaggcatt gagaggtgga ttgggaccctt tgtagtagaa ccttctggga  1320
tttcaggtat ggtgcctagt ttccagtgca tctgtacctc ccccttgaa actaggatct   1380
gatgcgccag tttctaagag gcctagattt ccttcatgcc aattgcatcg ttcaccgaga  1440
tctgaagcca gagaacattc tggtgacaag tggtggaaca gtcaagctgg ctgactttgg  1500
cctggccaga atctacagct accagatggc acttacaccc gtggtcagta gaaagatggt  1560
accaaaatgg gttctggttg ggaataggag agtgattgcc cgtagcaatt gagaagtcat  1620
gtgcttcatg tgttcagtca agcaagttgt gtttcatggt aacccatggg gtccccatcc  1680
attcttccta ttcccttag gttgttacac tctggtaccg agctcccgaa gttcttctgc   1740
agtccacata tgcaacacct gtggacatgt ggagtgttgg ctgtatcttt gcagagatgt  1800
tcgtcgaaa gtatgggacc cacatacccct ggactacctt gaattcccca aatcgcttgt  1860
tcataaacca catccatacc ttgcccattc ttttttttg agaccagggc ttgctgtgtt   1920
gcccaggctg gattgcaatg gcatgatcac agctcactgc agcttcaacc tcctgggctc  1980
aagtgatcct cccatctcag cttcccaact agctgacact acaggcacgc acctccatgc  2040
ttggctagtt tgttaatatt tttatagaga tggggtctca gtatattgcc caggctggtc  2100
ttgaactctt gcactcaagc aatcctccca ccctacctc ccaaagtagc ataagctact   2160
gcatctggcc ccattctttt acttgcgtac tactaacttg cccatagcag aaagctctga  2220
aatgttctgg aattaggaac ttcatatccc tttattctct ttatttttta tttatttatt  2280
tatttattta tttatttatt gagataaggt ttcactctgn nacccaggct ggagtncagt  2340
ggcccaatta nagctcactg tanccctctac ctcctgggct aaagmaatcc tcccatctca  2400
gccccttgag tanctgagac taaaggtgca cgccaccatg actggctttt tttttttta   2460
gatggagtct tgctctgtcg ccaggctgga gtgcagtagt gcgatctctg ctcactgcaa  2520
cctccacctc ccagattcaa gcaattctct tgactcagcc tcccaagtag ctgggaccac  2580
```

-continued

```
aggtgcacgc caccatgctc agctaatttt tgtactttta gtaatgacag gtttcaccat    2640
gttggccagg atggtctcga tctcttgacc tcatgatcca cccacatcag actcccaaag    2700
tgctaggatt acaggcgtga gcnnnngcac ctggcatttc ttttttttta aaaaagaga     2760
caaggtcttg cttgcccagg ctgatctaga actcctgggc tcaagcagtc ctctcacctc    2820
agcatcccaa agtgctggaa ttgttggcct ttattcccta tacttcctat tttgagccac    2880
taagcagtaa ccattcaact aagatatctt tgaaaatgac tgctacctta tatcccttct    2940
caccttaggc ctctcttctg tggaaactct gaagccgacc agttgggcaa aatctttgag    3000
taagtgacca acatgggaga aaagattttt ctattctgag tcctctttct gctgaaccca    3060
ggatggcaac tggctctgcc atggggatgg gaactggagg accctcctga ccagagttct    3120
cctgtccccc acagcctgat tgggctgcct ccagaggatg actggcctcg agatgtatcc    3180
ctgccccgtg gagcctttcc ccccagaggg ccccgcccag tgcagtcggt ggtacctgag    3240
atggaggagt cgggagcaca gctgctgctg gtaactggag atggctgtgg gcacagggaa    3300
agaaatagag actggggaaa gaaatagagc agtatgcagg gccctggcca ctgtggttaa    3360
tgaaacttgg ttggtagatg gtctgtagtt tttattacag ctgcaaatag ccacccacag    3420
agaaggatat agaagagaac ccatcctggc tgggcacggt ggctcacgcc tgtaatccca    3480
gcactttggg aggccaaggt gggcgtatca cctgaggtca ggagttcgag accagcctgg    3540
ccaacatggt gaaaccctcgt ctctactaaa agtacaaaaa taagccgggg gtggtggcac    3600
acgcctgtaa tctcagctac ttgggaggct gagataggag aatcacttca actcaggagg    3660
cggaggttgc agtgagctga gatcatacca ttggcactcc agcctgggtg atagagcgag    3720
actccgtctn caaaaaaaaa aaaaagaaa aagaagaaa gctcatccca ggtattgttg     3780
tgggtggcag aagctgtttt cttcatggtt ttctgacctt tgcctctccc ctcaggaaat    3840
gctgactttt aacccacaca agcgaatctc tgcctttcga gctctgcagc actcttatct    3900
acataaggat gaaggtaatc cggagtgagc aatggagtgg ctgccatgga aggaagaaaa    3960
gctgccattt cccttctgga cactgagagg gcaatctttg cctttatctc tgaggctatg    4020
gagggtcctc ctccatcttt ctacagagat tactttgctg ccttaatgac attccccctcc    4080
cacctctcct tttgaggctt ctccttctcc ttcccatttc tctacactaa ggggtatgtt    4140
ccctcttgtc cctttcccta cctttatatt tggggtcctt ttttatacag gaaaaacaaa    4200
accaaaagaa awaatggccc tttttttttt ttt                                 4233
```

<210> SEQ ID NO 28
<211> LENGTH: 714
<212> TYPE: DNA
<213> ORGANISM: Homo sapiens

<400> SEQUENCE: 28

```
gcatgatttg tgccaagcat tggagacaac tatacacaac attgaactac agtgcgtgga     60
atgcaaaaaa cctttgcaac gatctgaggg cgctgtgcgg cgtgttggag gtcccgacgt    120
agagaaactg cactgtgacg tgtaaaaacg ccatgagagg cacaagcca acgttaaagg    180
aatatgtttt agatttatat cctgaaccaa ctgacctata ctgctatgag caattaagtg    240
acagctcaga tgaggatgaa ggcttggacc ggccagatgg acaagcacaa ccagccacag    300
ctgattacta cattgtaacc tgttgtcaca cttgtaacac cacagttcgt ttatgtgtca    360
acagtacagc aagtgaccta cgaaccatac agcaactact tatgggcaca gtgaatattg    420
```

-continued

| tgtgccctac ctgtgcacaa caataaacat catctacaat ggccgatcct gaagcaacca | 480 |
| aatatccact actgaaactg ctgacataca gacagacaac gataaccgac caccacaagc | 540 |
| agcggccaaa cgacgacgac ctgcagacac cacagacacc gcccagcccc ttacaaagct | 600 |
| gttctgtgca gaccccgcct tggacaatag aacagcacgt actgcaacta actgcacaaa | 660 |
| caagcagcgg actgtgtgta gttctaacgt tgcacctata gtgcatttaa aagg | 714 |

<210> SEQ ID NO 29
<211> LENGTH: 456
<212> TYPE: DNA
<213> ORGANISM: Homo sapiens

<400> SEQUENCE: 29

| atgtttcagg acccacagga gcgacccaga aagttaccac atttatgcac agagctgcaa | 60 |
| acaactatac atgatataat attagaatgt gtgtactgca agcaacagtt actgcgacgt | 120 |
| gaggtatatg actttgcttt tcgggattta tgcatagtat atagagatgg gaatccatat | 180 |
| gcagtgtgtg ataaatgttt aaagttttat tctaaaatta gtgagtatag atattattgt | 240 |
| tatagtgtgt atggaacaac attagaacag caatacaaca aaccgttgtg tgatttgtta | 300 |
| attaggtgta ttaactgtca aaagccactg tgtcctgaag aaaagcaaag acatctggac | 360 |
| aaaaagcaaa gattccataa tataagggt cggtggaccg gtcgatgtat gtcttgttgc | 420 |
| agatcatcga gaacacgtag agaaacccag ctgtaa | 456 |

<210> SEQ ID NO 30
<211> LENGTH: 297
<212> TYPE: DNA
<213> ORGANISM: Homo sapiens

<400> SEQUENCE: 30

| atgcatggag atacacctac attgcatgaa tatatgttag atttgcaacc agagacaact | 60 |
| gatctctact gttatgagca attaaatgac agctcagagg aggaggatga aatagatggt | 120 |
| ccagctggac aagcagaacc ggacagagcc cattacaata ttgtaacctt ctgttgcaag | 180 |
| tgtgactcta cgcttcggtt gtgcgtacaa agcacacacg tagacatccg tacgttggaa | 240 |
| gacctgttaa tgggcacact aggaattgtg tgccccatct gttctcagaa accataa | 297 |

<210> SEQ ID NO 31
<211> LENGTH: 7130
<212> TYPE: DNA
<213> ORGANISM: Homo sapiens

<400> SEQUENCE: 31

| gaattccaca ttgtttgctg cacgttggat tttgaaatgc tagggaactt tgggagactc | 60 |
| atatttctgg gctagaggat ctgtggacca caagatcttt ttatgatgac agtagcaatg | 120 |
| tatctgtgga gctggattct gggttgggag tgcaaggaaa agaatgtact aaatgccaag | 180 |
| acatctattt caggagcatg aggaataaaa gttctagttt ctggtctcag agtggtgcag | 240 |
| ggatcaggga gtctcacaat ctcctgagtg ctggtgtctt agggcacact gggtcttgga | 300 |
| gtgcaaagga tctaggcacg tgaggctttg tatgaagaat cggggatcgt acccaccccc | 360 |
| tgtttctgtt tcatcctggg catgtctcct ctgcctttgt cccctagatg aagtctccat | 420 |
| gagctacaag ggcctggtgc atccaggtgt atctagtaat tgcagaacag caagtgctag | 480 |
| ctctccctcc ccttccacag ctctgggtgt ggagggggt tgtccagcct ccagcagcat | 540 |
| ggggagggcc ttggtcagcc tctgggtgcc agcagggcag gggcggagtc ctggggaatg | 600 |

-continued

```
aaggttttat agggctcctg ggggaggctc cccagcccca agcttaccac ctgcacccgg      660
agagctgtgt caccatgtgg gtcccggttg tcttcctcac cctgtccgtg acgtggattg      720
gtgagagggg ccatggttgg ggggatgcag gagagggagc cagccctgac tgtcaagctg      780
aggctctttc cccccaacc cagcacccca gcccagacag ggagctgggc tcttttctgt       840
ctctcccagc cccacttcaa gcccataccc ccagcccctc catattgcaa cagtcctcac      900
tcccacacca ggtccccgct ccctcccact taccccagaa ctttctcccc attgcccagc      960
cagctccctg ctcccagctg ctttactaaa ggggaagttc ctgggcatct ccgtgtttct     1020
ctttgtgggg ctcaaaacct ccaaggacct ctctcaatgc cattggttcc ttggaccgta     1080
tcactggtcc atctcctgag cccctcaatc ctatcacagt ctactgactt ttcccattca     1140
gctgtgagtg tccaacccta tcccagagac cttgatgctt ggcctcccaa tcttgcccta     1200
ggatacccag atgccaacca gacacctcct tcttcctagc caggctatct ggcctgagac     1260
aacaaatggg tccctcagtc tggcaatggg actctgagaa ctcctcattc cctgactctt     1320 agccccgac tcttcattca gtggcccaca ttttccttag gaaaaacatg agcatcccca      1380
gccacaactg ccagctctct gattccccaa atctgcatcc ttttcaaaac ctaaaaacaa     1440
aaagaaaaac aaataaaaca aaaccaactc agaccagaac tgttttctca acctgggact     1500
tcctaaactt tccaaaacct tcctcttcca gcaactgaac ctggccataa ggcacttatc     1560
cctggttcct agcacccctt atccctcag aatccacaac ttgtaccaag tttcccttct      1620
cccagtccaa gaccccaaat caccacaaag gacccaatcc ccagactcaa gatatggtct     1680
gggcgctgtc ttgtgtctcc taccctgatc cctgggttca actctgctcc cagagcatga     1740
agcctctcca ccagcaccag ccaccaacct gcaaacctag ggaagattga cagaattccc     1800
agcctttccc agctccccct gcccatgtcc caggactccc agccttggtt ctctgccccc     1860
gtgtcttttc aaacccacat cctaaatcca tctcctatcc gagtcccca gttccccctg      1920 tcaaccctga ttcccctgat ctagcacccc ctctgcaggc gctgcgcccc tcatcctgtc     1980
tcggattgtg ggaggctggg agtgcgagaa gcattcccaa ccctggcagg tgcttgtggc     2040
ctctcgtggc agggcagtct gcggcggtgt tctggtgcac ccccagtggg tcctcacagc     2100
tgcccactgc atcaggaagt gagtagggc ctggggtctg gggagcaggt gtctgtgtcc      2160
cagaggaata acagctgggc attttcccca ggataacctc taaggccagc cttgggactg     2220
ggggagagag ggaaagttct ggttcaggtc acatggggag gcaggttgg ggctggacca      2280 ccctccccat ggctgcctgg gtctccatct gtgtccctct atgtctcttt gtgtcgcttt     2340
cattatgtct cttggtaact ggcttcggtt gtgtctctcc gtgtgactat tttgttctct     2400
ctctccctct cttctctgtc ttcagtctcc atatctcccc ctctctctgt ccttctctgg     2460
tccctctcta gccagtgtgt ctcaccctgt atctctctgc caggctctgt ctctcggtct     2520
ctgtctcacc tgtgccttct ccctactgaa cacacgcacg ggatgggcct gggggaccc     2580 tgagaaaagg aagggctttg gctgggcgcg gtggctcaca cctgtaatcc cagcactttg     2640
ggaggccaag gcaggtagat cacctgaggt caggagttcg agaccagcct ggccaactgg     2700
tgaaacccca tctctactaa aaatacaaaa aattagccag gcgtggtggc gcatgcctgt     2760
agtcccagct actcaggagg ctgagggagg agaattgctt gaacctggga ggttgaggtt     2820
gcagtgagcc gagaccgtgc cactgcactc cagcctgggt gacagagtga gactccgcct     2880
caaaaaaaaa aaaaaaaaaa aaaaaaaaaa agaaaagaaa agaaagaaa aggaatcttt     2940
```

```
tatccctgat gtgtgtgggt atgagggtat gagagggccc ctctcactcc attccttctc    3000
caggacatcc ctccactctt gggagacaca gagaagggct ggttccagct ggagctggga    3060
ggggcaattg agggaggagg aaggagaagg gggaaggaaa acagggtatg ggggaaagga    3120
ccctggggag cgaagtggag gatacaacct tgggcctgca ggccaggcta cctacccact    3180
tggaaaccca cgccaaagcc gcatctacag ctgagccact ctgaggcctc ccctccccgg    3240
cggtccccac tcagctccaa agtctctctc ccttttctct cccacactttt atcatccccc    3300 ggattcctct ctacttggtt ctcattcttc ctttgacttc ctgcttccct ttctcattca    3360
tctgtttctc actttctgcc tggttttgtt cttctctctc tctttctctg gcccatgtct    3420
gtttctctat gtttctgtct tttctttctc atcctgtgta ttttcggctc accttgtttg    3480
tcactgttct cccctctgcc ctttcattct ctctgtcctt ttaccctctt cctttttccc    3540
ttggtttctc tcagtttctg tatctgccct tcaccctctc acactgctgt ttcccaactc    3600
gttgtctgta ttttggcct gaactgtgtc ttccccaacc ctgtgttttt ctcactgttt    3660 cttttctct tttggagcct cctccttgct cctctgtccc ttctctcttt ccttatcatc    3720
ctcgctcctc attcctgcgt ctgcttcctc cccagcaaaa gcgtgatctt gctgggtcgg    3780
cacagcctgt ttcatcctga agacacaggc caggtatttc aggtcagcca cagcttccca    3840
cacccgctct acgatatgag cctcctgaag aatcgattcc tcaggccagg tgatgactcc    3900
agccacgacc tcatgctgct ccgcctgtca gagcctgccg agctcacgga tgctgtgaag    3960
gtcatggacc tgcccaccca ggagccagca ctggggacca cctgctacgc ctcaggctgg    4020
ggcagcattg aaccagagga gtgtacgcct gggccagatg gtgcagccgg gagcccagat    4080
gcctgggtct gagggaggag gggacaggac tcctgggtct gagggaggag ggccaaggaa    4140
ccaggtgggg tccagcccac aacagtgttt ttgcctggcc cgtagtcttg accccaaaga    4200
aacttcagtg tgtggacctc catgttattt ccaatgacgt gtgtgcgcaa gttcaccctc    4260
agaaggtgac caagttcatg ctgtgtgctg gacgctggac aggggcaaaa agcacctgct    4320
cggtgagtca tccctactcc caagatcttg agggaaagg tgagtgggga ccttaattct    4380 gggctgggt ctagaagcca acaaggcgtc tgcctcccct gctccccagc tgtagccatg    4440
ccacctcccc gtgtctcatc tcattccctc cttccctctt ctttgactcc ctcaaggcaa    4500
taggttattc ttacagcaca actcatctgt tcctgcgttc agcacacggt tactaggcac    4560
ctgctatgca cccagcactg ccctagagcc tgggacatag cagtgaacag acagagagca    4620
gcccctccct tctgtagccc ccaagccagt gagggcaca ggcaggaaca gggaccacaa    4680
cacagaaaag ctggagggtg tcaggaggtg atcaggctct cggggaggga aaggggtgg    4740 ggagtgtgac tgggaggaga catcctgcag aaggtgggag tgagcaaaca cctgccgcag    4800
gggaggggag ggccctgcgg cacctggggg agcagaggga acagcatctg gccaggcctg    4860
ggaggagggg cctagagggc gtcaggagca gagaggaggt tgcctggctg gagtgaagga    4920
tcggggcagg gtgcgagagg gaagaaagga cccctcctgc agggcctcac ctgggccaca    4980
ggaggacact gcttttcctc tgaggagtca ggaactgtgg atggtgctgg acagaagcag    5040
gacagggcct ggctcaggtg tccagaggct gccgctggcc tccctatggg atcagactgc    5100
agggagggag ggcagcaggg atgtggaggg agtgatgatg gggctgacct ggggtggct    5160 ccaggcattg tccccacctg ggcccttacc cagcctccct cacaggctcc tggccctcag    5220
tctctcccct ccactccatt ctccacctac ccacagtggg tcattctgat caccgaactg    5280
accatgccag ccctgccgat ggtcctccat ggctccctag tgccctggag aggaggtgtc    5340
```

```
tagtcagaga gtagtcctgg aaggtggcct ctgtgaggag ccacgggac agcatcctgc      5400 agatggtcct ggcccttgtc ccaccgacct gtctacaagg actgtcctcg tggaccctcc      5460
cctctgcaca ggagctggac cctgaagtcc cttccctacc ggccaggact ggagcccta       5520 cccctctgtt ggaatccctg cccaccttct tctggaagtc ggctctggag acatttctct      5580
cttcttccaa agctgggaac tgctatctgt tatctgcctg tccaggtctg aaagatagga      5640
ttgcccaggc agaaactggg actgacctat ctcactctct ccctgctttt acccttaggg      5700
tgattctggg ggcccacttg tctgtaatgg tgtgcttcaa ggtatcacgt catggggcag      5760
tgaaccatgt gccctgcccg aaaggccttc cctgtacacc aagtggtgc attaccggaa       5820 gtggatcaag acaccatcg tggccaaccc ctgagcaccc ctatcaactc ctattgtag        5880 taaacttgga accttggaaa tgaccaggcc aagactcaag cctccccagt tctactgacc      5940
tttgtcctta ggtgtgaggt ccagggttgc taggaaaaga aatcagcaga cacaggtgta      6000
gaccagagtg tttcttaaat ggtgtaattt tgtcctctct gtgtcctggg aatactggc       6060 catgcctgga gacatatcac tcaatttctc tgaggcacaa gataggatgg ggtgtctgtg      6120
ttatttgtgg gatacagaga tgaaagaggg gtgggatcca cactgagaga gtggagagtg      6180
acatgtgctg gacactgtcc atgaagcact gagcagaagc tggaggcaca acgcaccaga     6240
cactcacagc aaggatggag ctgaaaacat aacccactct gtcctggagg cactgggaag     6300
cctagagaag gctgtgagcc aaggagggag ggtcttcctt tggcatggga tggggatgaa     6360
gtaaggagag ggactggacc ccctggaagc tgattcacta tgggggagg tgtattgaag      6420 tcctccagac aaccctcaga tttgatgatt tcctagtaga actcacagaa ataaagagct     6480
cttatactgt ggtttattct ggtttgttac attgacagga gacacactga atcagcaaa      6540 ggaaacaggc atctaagtgg ggatgtgaag aaaacaggga aaatctttca gttgttttct     6600
cccagtgggg tgttgtggac agcacttaaa tcacacagaa gtgatgtgtg accttgtgta     6660
tgaagtattt ccaactaagg aagctcacct gagccttagt gtccagagtt cttattgggg      6720
gtctgtagga taggcatggg gtactggaat agctgacctt aacttctcag acctgaggtt     6780
cccaagagtt caagcagata cagcatggcc tagagcctca gatgtacaaa acaggcatt      6840 catcatgaat cgcactgtta gcatgaatca tctggcacgg cccaaggccc caggtatacc     6900
aaggcacttg ggccgaatgt tccaagggat taaatgtcat ctcccaggag ttattcaagg    6960
gtgagccctg tacttggaac gttcaggctt tgagcagtgc agggctgctg agtcaacctt     7020
ttactgtaca gggggtgag ggaaagggag aagatgagga accgcctag ggatctggtt        7080 ctgtcttgtg gccgagtgga ccatgggct atcccaagaa ggaggaattc                 7130
```

<210> SEQ ID NO 32
<211> LENGTH: 5
<212> TYPE: PRT
<213> ORGANISM: Murine

<400> SEQUENCE: 32

Ala Arg Ile Asn Val
 1               5

<210> SEQ ID NO 33
<211> LENGTH: 11
<212> TYPE: PRT
<213> ORGANISM: E.Coli

<400> SEQUENCE: 33

-continued

```
Ala Ala Asn Asp Glu Asn Tyr Ala Leu Ala Ala
 1               5                   10

<210> SEQ ID NO 34
<211> LENGTH: 9
<212> TYPE: PRT
<213> ORGANISM: Artificial Sequence
<220> FEATURE:
<223> OTHER INFORMATION: Synthesized
<220> FEATURE:
<223> OTHER INFORMATION: "Xaa" in positions 2 and 6 stand for any amino
      acid;

<400> SEQUENCE: 34

Arg Xaa Ala Leu Gly Xaa Ile Xaa Asn
 1               5

<210> SEQ ID NO 35
<211> LENGTH: 10
<212> TYPE: PRT
<213> ORGANISM: S. cerivisiae

<400> SEQUENCE: 35

Lys Thr Lys Arg Asn Tyr Ser Ala Arg Asp
 1               5                   10
```

VACCINES WITH ENHANCED INTRACELLULAR PROCESSING

RELATED APPLICATION

This application claims priority to Kipps et al., VACCINES WITH ENHANCED INTRACELLULAR PROCESSING, U.S. Provisional Application No. 60/043,467, filed Apr. 10, 1997, which is incorporated herein by reference including drawings.

FEDERAL SPONSORSHIP

This work is supported by the U.S. government, under CA66000 awarded by the National Institutes of Health-NCI. The government may have certain rights in the invention.

FIELD OF THE INVENTION

This invention relates to the field of immunology, vaccination and immunotherapy.

BACKGROUND OF THE INVENTION

The following is a discussion of the relevant art, none of which is admitted to be prior art to the appended claims.

DNA vaccination is a technique whereby somatic cells are transfected in vivo with DNA directing synthesis of a target antigen. Ulmer et al. disclose hereologous protection against influenza by injection of DNA encoding a viral protein (*Science* 259:1745, 1993). Watanabe et al. disclose the induction of antibodies to a kappa variable region by gene immunization (*J. Immunol.* 151:2871, 1993). The expressed protein either can be secreted by the transfected cell or processed inside the cell and presented in the context of class I major histocompatibility (MHC) antigens, which can be recognized by T cells. One of the pathways whereby polypeptides are processed into peptides involves intracellular proteolysis of the polypeptide into peptide fragments that ultimately bind MHC molecules. One major candidate process for this pathway is that of polyubiquitination.

Ubiquitination ("Ub"), an ATP-dependent process, constitutes a preliminary step of targeting a proteolytic substrate for its eventual degradation by the proteosome, a large multi-catalytic protease. Experiments in yeast and rabbit reticulocyte lysates indicate that at least two distinct determinants can dictate the rate of its degradation: one is the identity of N-terminal residue (N-end rule) and the other is presence of specific internal lysine residue where polyubiquitin is initiated (Bachmair, A., et al. *Science* 234:179–186, 1986; Gonda, D. K., et al. *J. Biol. Chem.* 264:16700–16712, 1989; Bachmair, A., et al. *Cell* 56:1019–1032, 1989). N-terminal amino acids are largely classified into three different categories based upon their destabilizing potential and the half-life of a given protein varies significantly (from 2 min to >20h) depending on the identity of N-terminal amino acid (Bachmair, A., et al., *Science* 234:179–186, 1986; Gonda, D. K., et al. *J. Biol. Chem.* 264:16700–16712, 1989). Studies have indicated that intracellular degradation of proteins is required for antigen presentation to T cells (Townsend, A., et al. *J. Exp. Med.* 168:1211–1224, 1988; Townsend, A., et al. *Cell* 42:457–67, 1985; Germain, R. N. *Cell* 76:287–299, 1994).

Evidence that the Ub-mediated proteolytic pathway provides all of the substrates for the proteosome has remained inconclusive from temperature-sensitive UBEL mutant cells (Michalek, M. T., et al. *Nature* 363:552–554, 1993; Cox, J. H., et al. *J. Immunol.* 154:511–519, 1995). A recent study using pairs of N-end rule substrate proteins that varied in their intracellular stability provided evidence that the proteolytic turnover of endogenously synthesized proteins is not directly proportional to the generation of processed antigenic peptide/MHC class I complexes (Goth, S., et al. *J. Immunol.* 157:1894–1904, 1996). Goth et al., used the sindbis virus polymerase as the N-terminal target of the Ub-dependent degradation pathway. Earlier studies had shown that sindbis virus polymerase is a natural substrate for the N-rule (de Groot et al. *Proc. Natl. Acad. Sci. USA*, 88:8967, 1991).

Levy et al. (*Proc. Natl. Acad. Sci. USA* 93:4907, 1996) disclose a fusion protein consisting of a 21-kDa mouse DHFR moiety, an ubiquitin protein, a variable residue, 165 residues of nsP4 (Sinbis virus RNA polymerase) and β gal that is useful in a method to produce equimolar amounts of two or more specific proteins in a cell.

Grant, E. P., et al. (*J. Immunol.* 155:3750–3758, 1995) disclose that chimeric proteins comprising ubiquitin, a destabilizing amino acid, a lacI extension and β gal when loaded into LB27.4 cells (a B lymphoblastoid cell line) showed enhanced class I presentation compared to that of proteins with a stabilizing amino acid.

Bachmair et al. U.S. Pat. No. 5,496,721 disclose the use of genetic constructs that encode for ubiquitin fusion proteins with destabilizing amino acids at their N-termini.

A recent study found that ovalbumin (OVA) with methylated lysine groups which was resistant to ubiquitin-mediated degradation could still be presented via class I MHC, albeit at a reduced amount (Michalek, M. T., et al. *J. Immunol.* 157:617–624, 1996). This indicates that there may be a ubiquitin-independent pathway for class I presentation of antigens to the immune system.

WO 94/17816 disclose methods for the use of inhibitors of the ubiquitin-dependent proteolytic pathway to reduce cytolytic immune responses.

SUMMARY OF THE INVENTION

The present invention concerns methods for generating a cellular immune response by the introduction into cells DNA vectors encoding antigens that have enhanced rates of degradation. Such vectors allow for the production of a chimeric immunogen (protein) in the cell in which they are introduced. A chimeric immunogen includes a protein processing signal and a protein which is the target for a cellular immune response. The protein processing signal brings about enhanced rates of degradation of the target protein. For example, a protein processing signal may include a removable leader linked to an intervening amino acid which is linked to a ubiquitin acceptor. The protein processing signal is further linked to the target protein. In the cytoplasm the removable leader is cleaved off by proteolytic enzymes present in the cytoplasm. This exposes at the N-terminus of the protein an intervening amino acid which acts to reduce the stability of the immunogen. The chimeric immunogen contains a ubiquitin acceptor which allows for the attachment of ubiquitin by enzymes present in the cytoplasm of the cell, thus targeting the protein for degradation via the ubiquitin-proteosome pathway. Other protein processing signals that utilize the intracellular proteosome pathway for degradation (with or without ubiquitin) are encompassed in the present invention.

Applicants have unexpectedly discovered that such vectors that encode for chimeric immunogens which have enhanced rates of degradation via the ubiquitin-proteosome pathway are able to generate an enhanced cellular immune response. In addition, the response is limited to the cellular branch of the immune system and does not include the production of antibodies to the immunogen.

The present invention also concerns such vectors able to generate specific cellular immune response.

The vectors and methods of the present invention are especially useful in stimulating an immune response that can reject cancer cells or cells infected with virus. This may be particularly useful in the prevention or delay of the onset of de novo or recurrent cancer or in the treatment of viral infections.

The present invention offers several advantages over prior art methods for generating an immune response. The cellular immune response is greater than that achieved by the introduction of naked plasmid DNA encoding a target antigen. In addition, the ability to induce a cellular cytotoxic immune response against cells that express an antigen without inducing antigen specific antibodies offers other advantages. In regard to antigens that are presented by tumor cells, the production of antibodies directed to these antigens have been hypothesized to inhibit cellular immune responses to such antigens. Also, such antibodies may effect the growth/survival of tumor cells expressing an antigen that is also a signal transducing receptor by acting as agonists of the receptor. In addition, antibodies may cause pathology when cross reactive with self antigens.

In a first aspect the invention features a method for generating in a patient a cellular immune response to a target protein or portion thereof comprising the step of introducing into cells of the patient a vector containing a nucleotide sequence encoding a chimeric immunogen comprising a protein processing signal and the target protein or portion thereof, so that the chimeric immunogen is made within the cells and subsequently processed such that the target protein or portion thereof is presented to the patient's immune system so as to generate a cellular immune response.

Patients may be humans or other animals.

A cellular immune response encompasses the production of cytotoxic T lymphocytes. Cytotoxic T lymphocytes (CTLs) are a subset of T cells that can kill target cells expressing specific antigen(s) in the form of processed peptides that are presented in the context of major histocompatibility antigens (Abbas, A. K., et al. *Cellular and Molecular Immunology*, Philadelphia: W. B. Saunders Co., 1994b, p. 261–277). These cells play an important role in the immune response: (1) to intracellular infections of non-phagocytic cells, or infections that are not eradicated by phagocytosis, such as viral infections; (2) allografts; or (3) tumors (Abbas, A. K., et al. *Cellular and Molecular Immunology*, Philadelphia: W. B. Saunders Co., 1994a, p. 356–375).

A target protein or portion thereof includes any protein of interest which is subsequently degraded such that peptides of the protein are presented and generate a cellular immune response. Tumor antigens and viral antigens are especially preferred targets.

There are many tumor antigens that can be recognized by autologous CTL (Boon, T., et al. *J. Exp. Med.* 183:725–729, 1996; Disis, M. L., et al. *Curr. Opin. Immunol.* 8:637–642, 1996; Robbins, P. F., et al. *Curr. Opin. Immunol.* 8:628–636, 1996b). Such antigens are peptide fragments derived from cell proteins that either are restricted to the type of tissue from which the tumor is derived, are mutated during the course of malignant transformation, are aberrantly expressed by the tumor cell, and/or represent "neo" antigens resulting from errors in transcription, RNA processing, translation, and/or protein processing due to a mutation(s) idiosyncratic to the tumor cell. Also, viral antigens are often presented on infected cells and on some tumor cells. There are several examples of antigens that have been found to be recognized by human T cells. These antigens include, but are not restricted to, gp100 (Wolfel, T., et al. *Eur. J. Immunol.* 24:759–764, 1994; Kawakami, Y., et al. *J. Immunol.* 154:3961–3968, 1995), MART-1 (MelanA) (Castelli, C., et al. *J. Exp. Med.* 181:363–368, 1995), tyrosinase (Wolfel, T., et al. *Science* 269:1281–1284, 1995; Brichard, V. G., et al. *Eur. J. Immunol.* 26:224–230, 1996; Topalian, S. L., et al. *J. Exp. Med.* 183:1965–1971, 1996), MAGE-1 (Traversari, C., et al. *J. Exp. Med.* 176:1453–1457, 1992; van der Bruggen, P., et al. *Science* 254:1643–1647, 1991), MAGE-3 (Gaugler, B., et al. *J. Exp. Med.* 179:921–930, 1994), BAGE (Boel, P., et al. *Immunity.* 2:167–175, 1995), CAGE-1, 2 (Van den Eynde, B., et al. *J. Exp. Med.* 182:689–698, 1995), N-acetylglucosaminyltransferase-V (Guilloux, Y., et al. *J. Exp. Med.* 183:1173–1183, 1996), (Robbins, P. F., et al. *J. Immunol.* 154:5944–5950, 1995), B-catenin (Robbins, P. F., et al. *J. Exp. Med.* 183:1185–1192, 1996a), MUM-1 (Coulie, P. G., et al. *Proc. Natl. Acad. Sci. U.S.A.* 92:7976–7980, 1995), CDK4 (Kawakami, Y., et al. *Proc. Natl. Acad. Sci. U.S.A.* 91:6458–6462, 1994), Her-2 (ErbB-2)/neu (Peoples, G. E., et al. *Proc. Natl. Acad. Sci. U.S.A.* 92:432–436, 1995; Fisk, B., et al. *J. Exp. Med.* 181:2109–2117, 1995), human papillomavirus-E6, E7 (Ressing, M. E., et al. *Cancer Res.* 56:582–588, 1996; Alexander, M., et al. *Am. J. Obstet. Gynecol.* 175:1586–1593, 1996), and MUC-1 (Finn, O. J., et al. *Immunol. Rev.* 145:61–89. All references cited herein are hereby incorporated by reference. Table 1 list the GenBank accession numbers for nucleotide sequences encoding these antigens. Utilizing known techniques of recombinant DNA technology one of ordinary skill in the art could construct chimeric immunogens which contain these sequences as the target protein.

TABLE 1

EXAMPLES OF TUMOR ANTIGENS THAT CAN BE MODIFIED TO ENHANCE THEIR INTRACELLULAR PROTEOLYSIS[1]

| Antigen | GenBank Acc.# |
| --- | --- |
| gp100 | SEQ ID NO:1 |
| MART-1 | SEQ ID NO:2 |
| TYROSINASE | SEQ ID NO:3 |
| MAGE-1 | SEQ ID NO:4 |
| MAGE-2 | SEQ ID NO:5 |
| MAGE-3 | SEQ ID NO:6 |
| MAGE-3b | SEQ ID NO:7 |
| MAGE-4 | SEQ ID NO:8 |
| MAGE-4a | SEQ ID NO:9 |
| MAGE-4b | SEQ ID NO:10 |
| MAGE-5a | SEQ ID NO:11 |
| MAGE-5b | SEQ ID NO:12 |
| MAGE-6 | SEQ ID NO:13 |
| MAGE-8 | SEQ ID NO:14 |
| MAGE-9 | SEQ ID NO:15 |
| MAGE-10 | SEQ ID NO:16 |
| MAGE-11 | SEQ ID NO:17 |
| MAGE-41 | SEQ ID NO:18 |
| MAGE-Xp | SEQ ID NO:19 |
| BAGE | SEQ ID NO:20 |
| N-acetylglucosaminyltransferase-V Intron | SEQ ID NO:21 |
| p15 | SEQ ID NO:22 |
| MUM-1 | SEQ ID NO:23 |
| MUM-1b | SEQ ID NO:24 |
| MUM-1c | SEQ ID NO:25 |
| ErbB-2 (HER-2/neu) | SEQ ID NO:26 |
| CDK4 | SEQ ID NO:27 |
| Human papillomavirus | SEQ ID NO:28 |
| Human papillomavirus-E6 | SEQ ID NO:29 |

TABLE 1-continued

EXAMPLES OF TUMOR ANTIGENS THAT CAN BE MODIFIED
TO ENHANCE THEIR INTRACELLULAR PROTEOLYSIS[1]

| Antigen | GenBank Acc.# |
| --- | --- |
| Human papillomavirus-E7 | SEQ ID NO:30 |
| Prostate Specific Antigen (PSA) | SEQ ID NO:31 |

[1]All sequences included in this chart are hereby incorporated by reference.

Introduction into cells of a patient can be carried out either in vitro or in vivo. In vitro introduction entails the removal of cells from a patient and subsequent reintroduction of these cells into a patient once a vector has been introduced into the cells. Techniques for the isolation and reintroduction of cells are well known to those who practice the art. The vector can be introduced into the cells by standard DNA transfection techniques or electroporation or via liposomes (Potter, H., et al. *Proc. Natl. Acad. Sci. USA* 81:7161–715, 1984; Felgner, P. L., et al. *Nature* 337:387–388, 1989; Mannino, R. J., et al. *Biotechniques.* 6:682–690, 1988). Introduction of the vector in vivo can be carried out by direct injection of the vector into cells of the patient (Plautz, G. E., et al. *Proc. Natl. Acad. Sci. USA* 90:4645–4649, 1993; Wolff, J. A., et al. *Science* 247:1465–1468, 1990; Wu, G. Y., et al. *Biotherapy.* 3:87–95, 1991; Herweijer, Hans, et al. *Somatic Gene Therapy,* CRC Press, Inc., 1996, p. 183–202; Raz, E., et al. *Proc. Natl. Acad. Sci. USA* 91:9519–9523, 1994). Preferably, cells are of skeletal muscle origin, however other cell types are suitable for injection.

A protein processing signal is responsible for enhancing the rate of degradation of the target protein in the cytoplasm via the proteosome pathway. A preferred protein processing signal consists of a removable leader, an intervening amino acid, and an ubiquitin acceptor linked together.

The removable leader is a protein sequence which is cleaved, cotranslationally or following translation at the junction of the leader and any protein sequence to which it is attached. Cleavage is carried out by processing proteases which are specific for the leader and which are present in the cell in which the protein is expressed. The leader allows for the protein to remain in the cytoplasm prior to and subsequent to cleavage. Any sequence which can be specifically cleaved in the cytoplasm at a particular point within the expressed protein; for example, at the junction site with the adjoining intervening amino acid is useful in the present invention. Removable leaders which are useful in the present invention include ubiquitin, which is cleaved by ubiquitin specific processing proteases (Waxman, L., et al. *J. Biol. Chem.* 262:2451–2457, 1987; Orlowski, M. *Biochemistry* 29:10289–10297, 1990) and amyloid beta protein which is cleaved by secretase (Selkoe, D. J., et al. *Ann. N.Y. Acad. Sci.* 777:57–64, 1996).

The intervening amino acid present is preferably positioned at the N-terminus of the protein by the cleavage of the leader sequence. The intervening amino acid when present at the N-terminus of the chimeric immunogen destabilizes the protein and thus enhances its rate of degradation via the N-end rule. A preferred intervening amino acid is arginine. Preferably the rate of degradation is within minutes. Other suitable amino acid are described in Gonda, D. K., et al. (*J. Biol. Chem.* 264:16700–16712, 1989). The present invention also contemplates variation in the placement of the intervening amino acid, so long as the resulting protein is rapidly degraded within the target cell.

An ubiquitin acceptor is a molecule which contains a residue appropriately positioned from the N-terminal of the protein as to be able to be bound by ubiquitin molecules. Such residues preferentially have an epsilon amino group such as lysine. Physical analysis demonstrates that multiple lysine residues function as ubiquitin acceptor sites (King, R. W., et al. *Mol. Biol. Cell* 7:1343–1357, 1996b; King, R. W., et al. *Science* 274:1652–1659, 1996a). Examples of other ubiquitin acceptors include lacI or Sindis virus RNA polymerase. Ubiquitination at the N-terminal of the protein specifically targets the protein for degradation via the ubiquitin-proteosome pathway.

Other protein processing signals that destabilize the target proteins and allow for enhanced intracellular degradation via the proteosome pathway are contemplated in the present invention. These other methods to destabilize target proteins do not necessarily go through the ubiquitin pathway, but all are degraded in the cytoplasm via proteosomes.

The present invention contemplates the use of other protein processing signals which govern the rate(s) of intracellular protein degradation including, but not limited to, those described by Bohley, P., et al. (*Biol. Chem. Hoppe. Seyler* 377:425–435, 1996). Such processing signals include those that allow for phosphorylation of the target protein (Yaglom, J. A., et al. *Mol. Cell Biol.* 16:3679–3684, 1996; Yaglom, J., et al. *Mol. Cell Biol.* 15:731–741, 1995). Also contemplated by the present invention are modification of the chimeric immunogens that allow for post-translational arginylation (Ferber, S., et al. *Nature* 326:808–811, 1987; Bohley, P., et al. *Biomed. Biochim. Acta* 50:343–346, 1991) of the protein which can enhance its rate(s) of intracellular degradation. The present invention also contemplates the use of certain structural features of proteins that can influence higher rates of intracellular protein turn-over, including protein surface hydrophobicity, clusters of hydrophobic residues within the protein (Sadis, S., et al. *Mol. Cell Biol.* 15:4086–4094, 1995), certain hydrophobic pentapeptide motifs at the protein's carboxy-terminus (C-terminus) (e.g. ARINV (SEQ ID NO: 32), as found on the C-terminus of ornithine decarboxylase (Ghoda, L., et al. *Mol. Cell Biol.* 12:2178–2185, 1992; Li, X., et al. *Mol. Cell Biol.* 14:87–92, 1994), or AANDENYALAA (SEQ ID NO: 33), as found in C-terminal tags of aberrant polypeptides (Keiler, K. C., et al. *Science* 271:990–993, 1996) or PEST regions (regions rich in proline (P), glutamic acid (E), serine (S), and threonine (T) (Rogers, S. W., et al. *J. Biol. Chem.* 263:19833–19842, 1988)). Moreover, certain motifs have been identified in proteins that appear necessary and possibly sufficient for achieving rapid intracellular degradation. Such motifs include RxALGxIxN (SEQ ID NO: 34) region (where x=any amino acid) in cyclins (Glotzer, M., et al. *Nature* 349:132–138, 1991) and the KTKRNYSARD (SEQ ID NO: 35) motif in isocitrate lyase (Ordiz, I., et al. *FEBS Lett.* 385:43–46, 1996).

The present invention also contemplates enhanced cellular degradation of the chimeric immunogen which may occur by the incorporation into the target protein known protease cleavage sites. For example amyloid beta-protein can be cleaved by beta- and gamma-secretase (Iizuka, T., et al. *Biochem. Biophys. Res. Commun.* 218:238–242, 1996) and the two-chain vitamin K-dependent coagulation factor X can be cleaved by calcium-dependent endoprotease(s) in liver (Wallin, R., et al. *Thromb. Res.* 73:395–403, 1994).

The constructs of the present invention encode a target polypeptide linked to or containing a protein processing signal sequence, containing one or a combination of the aforementioned motifs and/or the required structural features, that can enhance the intracellular degradation of the polypeptide. Those of ordinary skill in the art can readily link or incorporate such protein processing signals into target proteins utilizing known techniques of recombinant DNA technology.

In preferred embodiments the target protein is greater than 25 amino acid residues; the protein is selected from the group consisting of tumor antigens or viral antigens; the vector further comprises a mammalian promoter; the cellular immune response is the predominate immune response in the patient.

A mammalian promoter is any promoter that will allow for transcription to be initiated in a mammalian cell. Examples of such promoters include the CMV (Cytomegalovirus), SV40 (Simian virus 40) and RSV (Rous Sarcoma Virus).

In a second aspect, the invention features a vector comprising a nucleotide sequence encoding a mammalian promoter and a chimeric immunogen comprising a protein processing signal and a target protein or portion thereof.

Vectors in addition to plasmids are included in the scope of the present invention such as replication-defective viral vectors including adenovirus vectors and retroviral vectors (Wu, G. Y., et al. *Biotherapy*. 3:87–95, 1991; Kipps, T. J. *J. Hematotherapy* 2:367–372, 1993).

It is also possible to attach genetic adjuvants that can enhance the ability of the host immune system to recognize cells expressing the proteolyzed polypeptide so as to enhance the efficacy of such vaccines. For example by co-injection of genes encoding interleukin-2 (IL-2) (Raz, E., et al. *Proc. Natl. Acad. Sci. USA* 90:4523–4527, 1993).

DESCRIPTION OF THE PREFERRED EMBODIMENTS

Chemicals

E64-D (2S.3S-t-epoxysuccinyl-L-leucylamido-3-methyl-butane ethyl ester) and chloroquine were purchased from Sigma (St. Louis, Mo.). LLnL (N-acetyl-L-leucinyl-L-leucinal-L-norleucinal), a proteosome inhibitor (Rock, K. L., et al. *Cell* 78:761–771, 1994), was purchased from Boehringer Mannheim (Indianapolis, Ind.). Lactacystin is a streptomyces metabolite (purchased from Dr. Cohen, Harvard University). E64-D was dissolved in DMSO, LLnL in ethanol and the final concentration of each reagent in cell culture was kept at 0.25%. Both chloroquine and lactacystin were dissolved in water.

Cell Lines

P815, a mastocytoma cell line from DBA/2 mice (H-$2^d$), was maintained in RP10 media (RPMI-1640, 10% fetal calf serum (FCS), 50 uM 2-ME, antibiotics and L-glutamine). P13.2 is P815 transfected with *Escherichia coli* β gal that was maintained in RP10 with 0.4 mg/ml G418. 0805B, a H-$2L^d$-restricted β gal-specific CTL clone, was provided by Dr. Michael Bevan (University of Washington, Seattle, Wash.) and was maintained by weekly stimulation of $5 \times 10^4$ CTL with $10^5$ irradiated P13.2 and $3 \times 10^6$ irradiated splenocytes from BALB/c (H-$2^d$) mice (Jackson Laboratories, Bar Harbor, Me.) in 2 ml RP10, containing 50 uM 2-mercaptoethanol and 50 u/ml IL2 from supernatant of P3-IL2 transfectant cells in 24-well tissue culture plates.

Plasmids & Stable Transfectants

Figure 1:
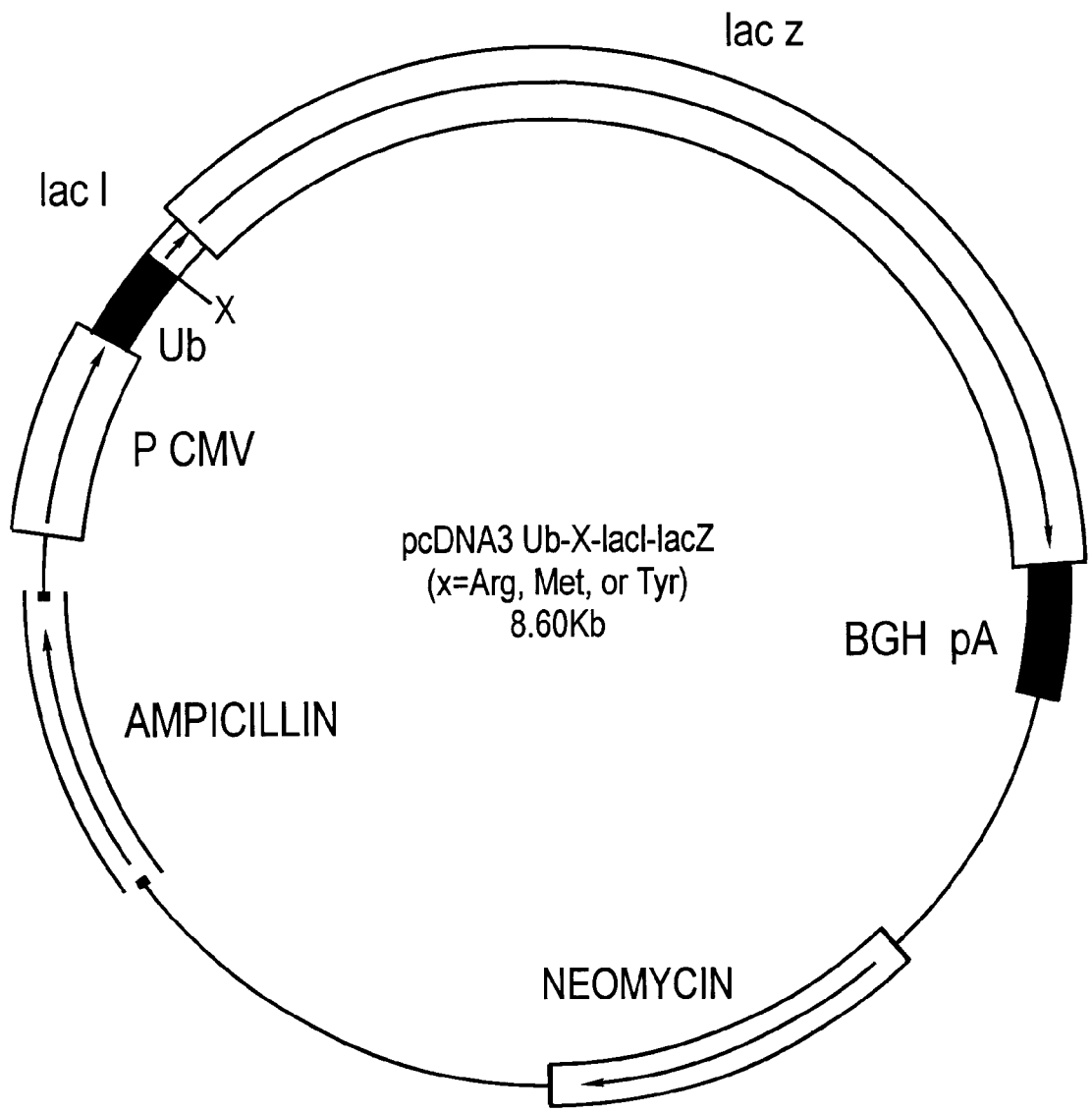
FIG. 1 shows the construct of plasmid pcDNA3 Ub-X-lacI-lacZ.

Plasmid, pUB23 (Bachmair, A., et al., *Science* 234:179–186, 1986) encodes Ub-X-lacI-lacZ, a fusion protein comprised of yeast ubiquitin, X residue (X=Arg, Met or Tyr), *Escherichia coli* lacI segment (residues 1030–1149) and β-galactosidase (β gal). Upon expression, cleavage occurs after the last residue of ubiquitin by cytosolic ubiquitin protease exposing the X-residue as the N-terminal residue. The internal lysine residue is provided in the lacI segment to serve as the ubiquitin acceptor. The chimeric genes Ub-X-lacZ were subcloned into pcDNA3, a mammalian expression vector under the control of the human CMV promoter (Invitrogen, CA) to generate pcDNA3Ub-X-lacI-lacZ (X=Arg, Tyr or Met) (See FIG. 1) (These plasmids are designated Ub-X-lacZ where X=Arg, Tyr, or Met). pRcC-MVlacZ (lacZ) is the name of the plasmid encoding the wildtype β gal. The 5' non-coding region of ubiquitin was modified by introducing a Kozak sequence (GCCACC) to direct efficient translation of the chimeric gene transcripts in mammalian cells. The plasmids were transfected into P815 by electroporation. After clonal selection, the stable transfectants were used for the described experiments.

β Gal Assay

After P815 transfectants were washed in FACS buffer (RPMI/3% FCS/0.05% sodium azide), they were resuspended in 0.1 ml of same buffer and incubated for 10 min at 37° C. Cells were then loaded with 0.1 ml prewarmed β gal substrate, fluorescein di-B-D-galactopyranoside (FDG, 2 mM in water) (Molecular Probes, OR) for 1 min. at 37° C. by hypotonic shock. The reaction was stopped by addition of 2 ml of ice-cold FACS buffer. Since nonfluorescent FDG is hydrolyzed by β gal to flurorescine monogalactoside (FMG) and then to highly fluorescent fluorescein, intracellular β gal activity can be measured by Flow Cytometric Analysis (FACS).

Preparation of Plasmid DNA

DNA was prepared using Qiagen megaprep kits (Qiagen, Chatsworth, Calif.), with the modification of adding onetenth volume 10% Triton X-114 (Sigma) to the filtered bacterial lysate for 30 min on ice before applying it to the column. Purified DNA was suspended in sterile saline and endotoxin level was tested using a limulus extract clot assay (Associates of Cape Cod, Wood Hole, Mass.).

Immunization of Mice

Six to eight-week-old BALB/c mice were injected intramuscularly in the rear quadriceps with 100 ug of either Ub-X-lacZ, lacZ, or the pcDNA3 as control vector in a total volume of 100 ul saline using a 25-gauge needle. Injections were given weekly for four times.

Antibody Assays

Anti-β gal antibodies were measured by ELISA. Microtiter plates were coated overnight with 5 ug of β gal (Calbiochem, La Jolla, Calif.) per ml of phosphate-buffered saline (PBS, pH 7.4) and then washed with PBS. Nonspecific binding sites were then blocked with 1% bovine serum albumin in PBS. After washing four times in PBS/0.5% Tween 20, serum samples diluted 1:100 in PBS were added to the wells. After 1 hr incubation at room temperature (RT), the plates were washed with PBS/Tween 20 and incubated with alkaline phosphatase-labeled goat anti-mouse IgG (Pharmingen, Calif.) for 1 hr at RT. The plates were then washed with PBS/Tween 20 and p-nitrophenyl phosphate (5 mg/ml, Sigma), an alkaline phosphatase substrate was added. The level of anti-β gal Ab was determined by absorbance at 405 nm read 30 min after addition of the substrate. Results are expressed in OD.

Cytotoxicity Assay

Splenocytes from immunized mice were isolated 12 weeks after injection. $7 \times 10^6$ responder splenocytes were incubated with $0.5 \times 10^6$ stimulator P13.2 which was irradiated at 20,000 rads in RP10. 5 days later, 25 U/ml recombinant murine IL-2 (Biosource International, CA) was added to the culture and incubated for another 2 days. Then the restimulated cells were harvested and separated from dead cells on a Lymphocyte M (Accurate Chemicals, Westbury, N.Y.) gradient. The targets were P815 and P13.2, as negative and positive control, respectively. In 96-well round-bottom plates, target cells were incubated with responder cells at different effector to target ratio for 4 h. in phenol red-free RPMI-1640 containing 2% BSA, 2 mM glutamine and 1% penicillin and streptomycin. 50 ul/well of the supernatant was then transferred to a 96-well plates and lysis was determined by measuring lactate dehydrogenase (LDH) release using the Cytotox 96 assay kit (Promega Corp., Madison, Wis.). The released LDH converts the added substrate tetrazolin salt (INT) into red formazan product and the amount of color is proportional to the number of lysed cells. The absorbance values from supernatant is recorded at O.D. 490 nm (O.D.) on an ELISA reader. Percent lysis is calculated as follows:

$$\frac{O.D._{Exp} - O.D._{Spon.\ E} - O.D._{Spon.\ T}}{O.D._{Max.\ T} - O.D._{Spon.\ T}} \times 100$$

$O.D._{Exp}$=O.D. of the supernatant containing the effector cells (e.g., CTL) and target cells (e.g., tumor cells).

$O.D._{Spon.E}$ =O.D. of the supernatant containing only effector cells.

$O.D._{Spon.\ T}$=O.D. of the supernatant containing only target cells.

$O.D._{Max.\ T}$=O.D. of the supernatant containing target cells that were lysed.

Administration

The phrase "suitable for human use" and "pharmaceutically acceptable" (physiologically tolerable) refer to molecular entities and compositions that do not typically produce an allergic or similar untoward reaction, such as gastric upset, dizziness and the like, when administered to a human.

The term "unit dose" as it pertains to the inocula of the present invention refers to physically discrete units suitable as unitary dosages for animals, each unit containing a predetermined quantity of active material calculated to produce the desired immunogenic effect in association with the required diluent; i.e., carrier, or vehicle. The specifications for the novel unit dose of an inoculum of this invention are dictated by and are directly dependent on (a) the unique characteristics of the active material and the particular immunologic effect to be achieved, and (b) the limitations inherent in the art of compounding such active material for immunologic use in animals and human subjects, as disclosed in detail herein, these being features of the present invention.

The vaccines are administered in a manner compatible with the dosage formulation, and in such amount as will be therapeutically effective and immunogenic. The quantity to be administered depends on the subject to be treated, capacity of the subject's immune system to generate a cellular immune response, and degree of protection desired. Precise amounts of active ingredient required to be administered depend on the judgment of the practitioner and are peculiar to each individual. However, suitable dosage ranges are of the order of about one hundred micrograms to about one hundred milligrams, preferably about one to about 10 milligrams and more preferably about 5 milligrams active ingredient per kilogram bodyweight individual. Suitable regimes for initial administration and booster shots are also variable, but are typified by an initial administration followed in one or two week intervals by a subsequent injection or other administration.

Ex vivo methods are contemplated wherein the cells into which the chimeric immunogen gene is to be introduced are isolated from the animal or patient and then the gene is introduced into those isolated cells using suitable methods. Examples of useful ex vivo methods have been described for example by Raper, S. E., et al. *Ann. Surg.*, 223:116, 1996; Lu, L., R. N. Shen, and H. E. Broxmeyer, *Crit. Rev. Oncol. Hematol.*, 22:61, 1996; Koc, O. N., et al. *Semin. Oncol.*, 23:46 1996; Fisher, L. J., et al. *Curr. Opin. Neurobiol.*, 4:735, 1994; and Goldspiel, B. R., et al. *Clin. Pharm.*, 12:488, 1993. Following the introduction of the gene, including any optional steps to assure that the chimeric immunogen gene has been successfully introduced into those isolated cells, the isolated cells are introduced into the patient either at a specific site or directly into the circulation of the patient. In preferred embodiments of the present invention, cell surface molecules, such as antigens that identify specific cells, are used to specifically isolate such desired cells from the patient. One of ordinary skill in the art will understand that such isolation methods are well known and include such methodologies as fluorescent activated cell sorting (FACS), immunoselection involving a variety of formats including panning, columns, or other similar methods.

The present invention also contemplates introducing the chimeric immunogen gene into the desired cells within the body of an animal or human patient without first removing those cells from the patient. Methods for introducing genes into specific cells in vivo, or within the patient's body are well known and include use of gene therapy vectors and direct injection of various genetic constructs into the animal or patient. Examples of useful methods have been described by Danko, I., et al. (*Vaccine*, 12:1499, 1994; Raz, E., et al. *Proc. Natl. Acad. Sci. U.S.A.*, 90:4523, 1993; Davis, H. L., et al. *Hum. Gene Ther.*, 4:151, 1993; Sugaya, S., et a. *Hum. Gene Ther.*, 7:223, 1996; Prentice, H., et al. *J. Mol. Cell Cardiol.*, 28:133, 1996; Soubrane, C., *Eur. J. Cancer*, 32A:691, 1996; Kass-Eisler, A., *Ann. N.Y. Acad. Sci.*, 772:232, 1995; DeMatteo, R. P., et al. *Ann. Surg.*, 222:229, 1995; Addison, C. L., et al. *Proc. Natl. Acad. Sci. U.S.A.*, 92:8522, 1995; Hengge, U. R., et al. *J. Clin. Invest.*, 97:2911, 1996; Felgner, P. L., et al. *Ann. N. Y. Acad. Sci.*, 772:126, 1995; and Furth, P. A., et al. *Hybridoma*, 14:149, 1995). In a typical application, a gene therapy vector containing a chimeric immunogen gene is introduced into the circulation or at a localized site of the patient to allow the gene therapy vector to specifically infect the desired cells. The present invention also contemplates the direct injection of DNA from a genetic construct into a patient or animal. Examples of such useful methods have been described by Vile, R. G., et al. (*Ann. Oncol.*, 5 Suppl 4:59, 1994). The genetic construct DNA is directly injected into the muscle or other sites of the animal or patient.

Genetic Constructs

The chimeric immunogens of the present invention may be constructed using standard genetic engineering methods to operatively link a protein processing signal nucleotide sequence to a nucleotide sequence encoding a target protein. In addition, standard genetic engineering methods may be used to insert man-made nucleotide sequences or sub-domain nucleotide sequences into the target protein. One of ordinary skill in the art will understand that various methods may be utilized to produce such chimeric immunogens. For example, a gene conversion method known as "SOEN" may be used to produce a chimeric immunogen. The methods for using this gene conversion method are well known in the art and have been described for example in Horton, R. M. *Mol. Biotechnol.*, 3:93, 1995; Ali, S. A., et al. *Biotechniques*, 18:746, 1995; Vilardaga, J. P., et al. *Biotechniques*, 18:604, 1995; Majumder, K., et al. *PCR. Methods Appl.*, 4:212, 1995; Boles, E., et al. *Curr. Genet.* 28:197, 1995; Vallejo, A. N., et al. *PCR. Methods Appl.*, 4:S123, 1994; Henkel, T., et al. *Anal. Biochem.*, 214:351, 1993; Tessier, D. C., et al. *Biotechniques*, 15:498, 1993; Morrison, H. G., et al. *Biotechniques*, 14:454, 1993; Cadwell, R. C., et al. *PCR. Methods Appl.*, 2:28, 1992; and Stappert, J., et al. *Nucleic Acids Res.*, 25 20:624, 1992. Alternatively, one of ordinary skill in the art will understand that site-directed mutagenesis may be used to introduce changes into a particular nucleotide sequence to directly produce or indirectly be used to produce a chimeric immunogen of the present invention. For example, the mutagen kit provided by BioRad Laboratories may be used together with the methods and protocols described within that kit to produce the desired changes in the nucleotide sequence. These methods were originally described by Kunkel (*Proc. Natl. Acad. Sci. USA*, 82:488–492, 1985) and Kunkel et al., (*Meth. Enzol. Mol.*, 154:367–382, 1987). By using the site directed mutagenesis protocols described herein and known within the art, a skilled investigator may induce individual nucleotide changes which result in an altered amino acid sequence or which preserve an amino acid sequence but introduce a desired restriction enzyme recognition sequence into a protein processing or target protein sequence. This new restriction endonuclease recognition site may then be used to cut any sequence at that particular point and to attach or insert another sequence of interest. In addition to these methods, one of ordinary skill in the art will understand that an entire chimeric immunogen molecules may be synthesized using synthetic methods known in the art. This methodology only requires that the skilled artesian generating nucleotide sequence of a chimeric immunogen molecule and provide that sequence to a company which is capable of synthesizing such a gene.

Promoters

Other promoters that are particularly useful for expressing genes and proteins within eukaryotic cells include mammalian cell promoter sequences and enhancer sequences such as those derived from polyoma virus, adenovirus, simian virus 40 (SV40), and the human cytomegalovirus. Particularly useful are the viral early and late promoters which are typically found adjacent to the viral origin of replication in viruses such as the SV40. Examples of various promoters which have been used in expression vectors have been described by Okiama and Berg (*Mol. Cell. Biol.* 3:280, 1983), the pMLSVN SV40 described by Kossman et al. (*Nature* 312:768, 1984). One of ordinary skill in the art will understand that the selection of a particular useful promoter depends on the exact cell and the other various parameters of the genetic construct to be used to express the chimeric immunogen or the chimeric immunogen gene within a particular cell. In addition, one of ordinary skill in the art will select a promoter which is known to express genes in the target cell at a sufficiently high level to be useful in the present invention.

The genetic vectors and expression vectors of the present invention optionally contain various additional regulatory sequences including ribosome binding sites which allow the efficient translation of the messenger RNA produced from an expression vector into proteins.

The genetic constructs contemplated by the present invention therefore include various forms of accessory genes which are operatively linked to either a promoter sequence or a promoter and enhancer sequence and also operatively linked to a polyadenylation sequence which directs the termination and polyadenylation of messenger RNA. It is also contemplated that the genetic constructs of the present invention will contain other genetic sequences which allow for the efficient replication and expression of that construct within the desired cells. Such sequences may include introns which are derived from native target protein genes or, for example, from a virus gene.

The present invention also contemplates gene therapy vectors which are able to directly infect mammalian cells so as to introduce the desired chimeric immunogen gene into that cell. These gene therapy vectors are useful for directly infecting cells which have been isolated from an animal or patient, or can be directly introduced into an animal or patient and thereby directly infect the desired cell within that animal or patient.

Many types of gene therapy vectors which are able to successfully transfer genes and cause the expression of desired foreign DNA sequences have been developed and described in the literature. For example, the article entitled "Gene Transfer Vectors for Mammalian Cells" in *Current Comm. Mol. Biol.*, Cold Springs Harbor Laboratory, New York (1987). Further, naked DNA can be physically introduced into eukaryotic cells including human cells by transfection using any number of techniques including calcium phosphase transfection (Berman et al., *Proc. Natl. Acad. Sci. USA*, 81:7176, 1984), DEAE-Dextran Transfection, protoplast fusion (Deans et al., *Proc. Natl. Acad. Sci. USA*, 81:1292, 1984), electroporation, liposome fusion, polybrene transfection and direct gene transfer by laser micropuncture of the cell membrane. In addition, one of ordinary skill in the art will understand that any technique which is able to successfully express the chimeric immunogen in a cell would be useful in the present invention.

Specifically, gene therapy vectors which utilize recombinant infectious virus particles for gene delivery have been widely described. See, for example, Brody, S. L., et al. *Ann. N. Y. Acad. Sci.*, 716:90, 1994; Srivastava, A. *Blood. Cells*, 20:531, 1994; Jolly, D. *Cancer Gene Ther.*, 1:51, 1994; Russell, S. J., *Eur. J. Cancer*, 30A:1165, 1994; Yee, J. K., et al. *Methods Cell Biol.*, 43 Pt A:99, 1994; Boris-Lawrie, K. A. et al. *Curr. Opin. Genet. Dev.*, 3:102, 1993; Tolstoshev, P., *Annu. Rev. Pharmacol. Toxicol.*, 33:573, 1993; and, Carter, B. J. *Curr. Opin. Biotechnol.*, 3:533, 1992). The present invention contemplates the use of gene therapy vectors to carry out the desired methodology of the present invention by introducing a gene encoding a chimeric immunogen into the cell. Many viral vectors have been defined and used as gene therapy vectors and include virus vectors derived from simian virus 40 (SV40), adenoviruses, adeno-associated viruses, and retroviruses. One of ordinary skill in the art will understand that useful gene therapy vectors are vectors which are able to directly introduce into the target cells the DNA which encodes the chimeric immunogen and allow that DNA to persist in the cell so as to express the chimeric immunogen in the desired manner within the cell.

The gene therapy vectors of the present invention are useful for introducing chimeric immunogen genes into a variety of mammalian cells including human cells. The particular cells infected by the gene therapy vector will depend on the various specifics of the vector.

A large variety of methods are contemplated in which the final result is that the chimeric immunogen gene is introduced into the desired cells. These methods include ex vivo methods, in vivo methods and various other methods which involve injection of DNA, genetic vectors or gene therapy vectors into the animal or human.

The following Examples are provided for further illustrating various aspects and embodiments of the present invention and are in no way intended to be limiting in scope.

EXAMPLE 1

β Gal Protein Expression and β Gal Activity in p815 Ub-X-lacZ Transfectants

Figure 2:
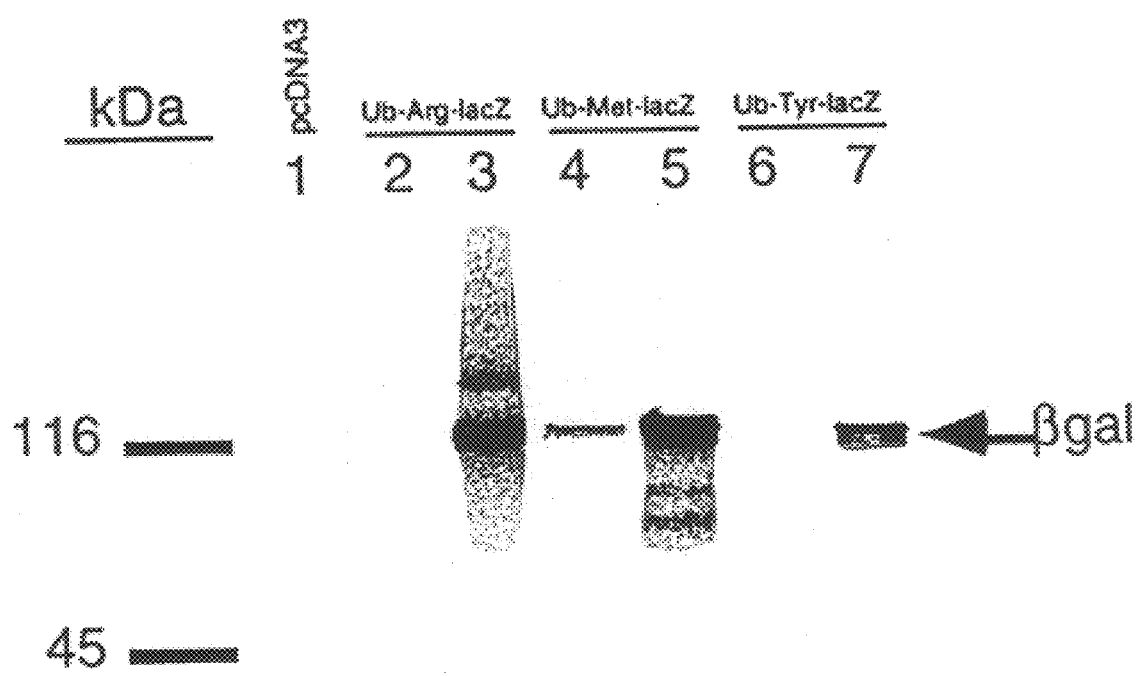
FIG. 2 shows the detection by immunoblot of β gal expression from P815 transfectants and in vitro translated protein mixture. Lane 1 is control pcDNA3, lanes 2, 4, 6 are cell lysate from P815/Ub-X-lacZ (X=Arg, Met or Tyr) transfectants and lanes 3, 5 and 7 are in vitro translated protein mixture from plasmids Ub-X-lacZ. The arrow indicates β gal protein migrating at 116 kDa.
Figure 3:
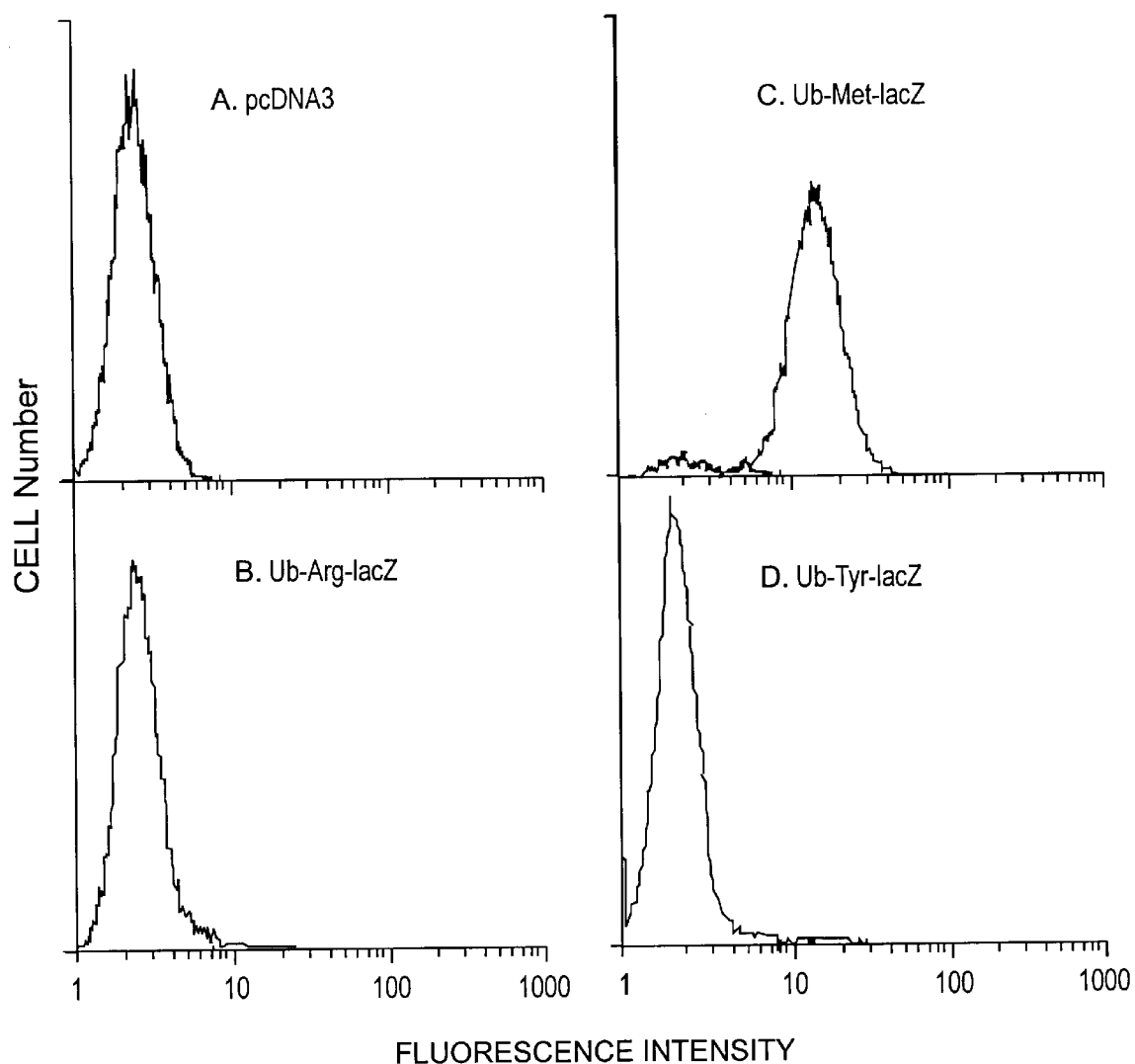
FIG. 3 shows the detection of β gal activity in four P815 transfectants by β gal assay and FACS analysis. The x and y axes represent the logarithm of the fluorescence intensity and the cell number on arbitrary scales, respectively.

To test Ub-X-β gal protein expression in mammalian cells, three different plasmids Ub-X-lacZ (X=Arg, Met, or Tyr) were transfected into P815 (a murine mastoocytoma cell line) by electroporation with pcDNA3 as a negative control. After G418 and clonal selection, cell lysates were analyzed by SDS-PAGE-immunoblot with anti-β gal monoclonal Ab and detected by Enhanced Chemiluminescense (ECL) (Amersham, Ill.). As shown in FIG. 2 (lanes 1, 2, 4 & 6), β gal protein of 116 kDa was only detected in Ub-Met-lacZ P815 transfectant. The β gal activity in these transfectants also was assayed by FACS. Cells were loaded with the β gal substrate, FDG, and analyzed for fluorescence intensity by flow cytometry as previously described. FIG. 3 shows the FACS profiles obtained with the stable transfectants. Consistent with the immunoblot, 92% Ub-Met-lacZ transfectant cells have β gal activity whereas Ub-Arg-lacZ and Ub-Tyr-lacZ are the same as negative control, pcDNA3.

Since neither β gal protein nor its activity can be detected in Ub-Arg-lacZ and Ub-Tyr-lacZ transfectants, the competence of these two constructs was determined by in vitro transcription and translation. An approximately 116 kDa band (same size of β gal ) was detected in all Ub-X-lacZ constructs (FIG. 2, lanes 3, 5, & 7). Furthermore, RNA transcripts of lacZ from these transfectants also were detected by RT-PCR (data not shown).

These data indicate that the proteins Ub-Arg-β gal and Ub-Tyr-β gal may be metabolized rapidly in the transfected P815 cell, consistent with these proteins being proteolyzed by a ubiquitin proteosome-dependent pathway. Consequently, the rate of β gal protein degradation appears much faster than that of its synthesis in P815 Ub-Arg or Tyr-lacZ transfectants.

Therefore, β-galactosidase activity in these transfectants cannot be detected.

EXAMPLE 2

Effect of Proteosome Inhibitors on the Expression of Ub-X-β Gal

Proteosome inhibitors have been shown to inhibit major peptidase activity of 20S and 26S proteosome function in cells and reduce the degradation of protein and ubiquitinated protein substrate. The effect of different kinds of cell-penetrating proteosome inhibitors on the level of β gal activity in Ub-X-lacZ transfectants was examined. Peptide aldehyde N-acetyl-L-leucinyl-L-leucinal-L-norleucinal (LLnL) (Rock, K. L., et al. *Cell* 78:761–771, 1994) is an substrate-related inhibitor of the chymotryptic site on the proteosome. Lactacystin (Mori, S., et al. *J. Biol. Chem.* 270:29447–29452, 1995) is a streptomyces metabolite specific proteosome inhibitor.

Figure 4:
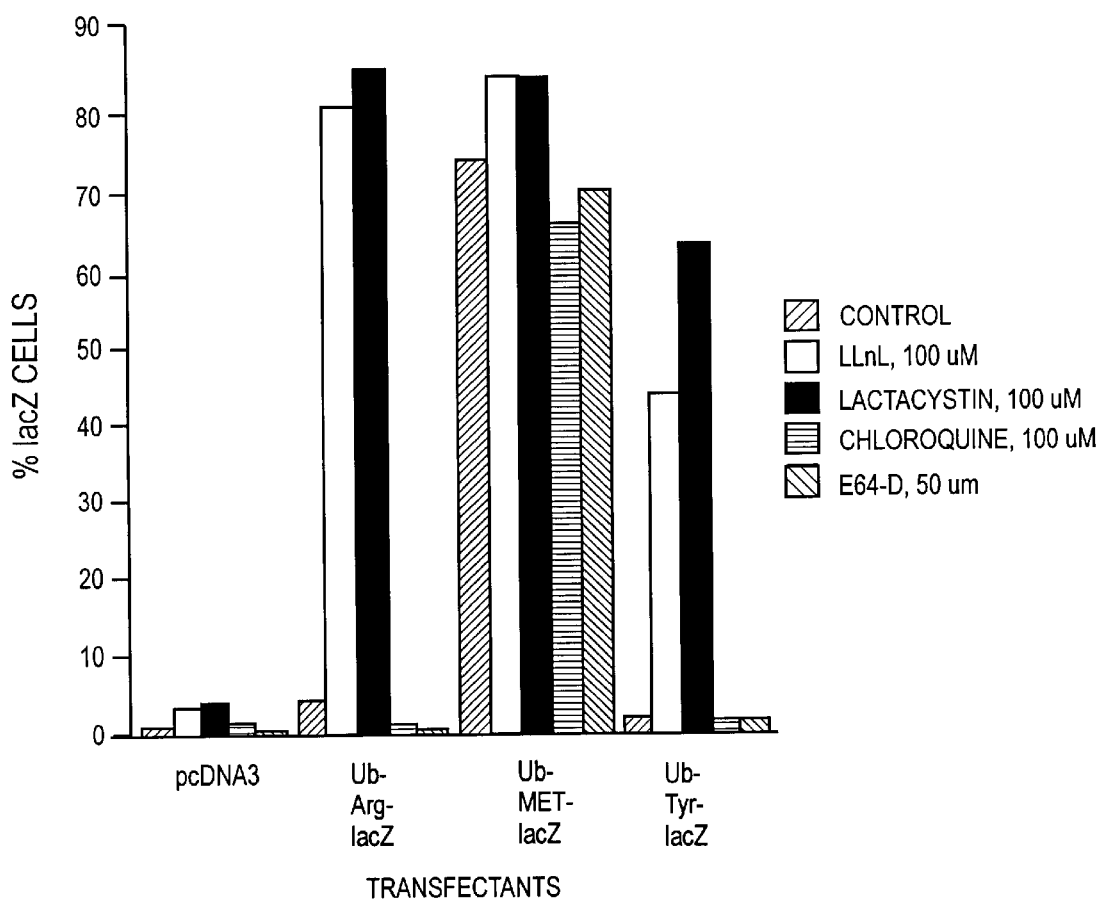
FIG. 4 shows the effects of inhibitors on β gal expression in P815 transfectants. Four different P815 transfectants (shown on the x-axis) were pre-incubated with control, proteosome inhibitors LLnL and lactacystin, lysosome inhibitor chloroquine or calpain inhibitor E64-D for 2 hours at 37° C. β gal activity is shown on the y-axis.

After different P815 transfectants were incubated with proteosome inhibitors at loo uM for 2 h at 37° C., the cells were washed and β gal activity was determined by β gal assay and FACS. LLnL caused a tremendous increase of β gal activity in both Ub-Arg-lacZ and Ub-Tyr-lacZ transfectants, with 81% and 44% of cells positive for lacZ, respectively (FIG. 4). Lactacystin had a stronger effect on β gal activity than LLnL. These data indicate that ubiquitin-proteosome is involved in the degradation process of Ub-(Arg, Tyr)-β gal. Both LLnL and lactacystin had little effect on the β gal level in the Ub-Met-lacZ transfectant, where Met is a stabilizing residue in yeast and rabbit reticulocyte (Bachmair, A., et al. *Science* 234:179–186, 1986; Gonda, D. K., et al. *J. Biol. Chem.* 264:16700–16712, 1989). Two other protein proteolysis pathway inhibitors also were used to confirm the involvement of proteosome in the degradation of Ub-Arg-β gal and Ub-Tyr-β gal. Treatment of cells with E64-D (50 $\mu$M), a specific calpain inhibitor or chloroquine (100 $\mu$M), a lysosomal degradation inhibitor, had no effect on the level of β gal activity, further suggesting that ubiquitin-proteosome dependent proteolysis, but no other pathway is involved in the rapid degradation of the N-end rule substrates Ub-Arg-β gal and Ub-Tyr-β gal.

EXAMPLE 3

Effects of Ub-X-β Gal Protein Degradation on Antigen Presentation

An important function of intracellular proteolysis is to generate the small peptides that are bound to MHC class I molecules, transported to plasma membrane and presented to cytotoxic CD8 T lymphocytes to initiate immune response. During this process, proteosomes may play a role in MHC class I presentation (Goldberg, A. L., et al. *Nature* 357:375–379, 1992). The fact that proteosome inhibitors can increase the level of β gal activity in P815 transfectants suggests that Ub-X-β gal is degraded by ubiquitin-proteosome dependent proteolysis. Therefore the effects of increased Ub-X-β gal degradation on its antigenicity was assessed through CTL assay.

Figure 5:
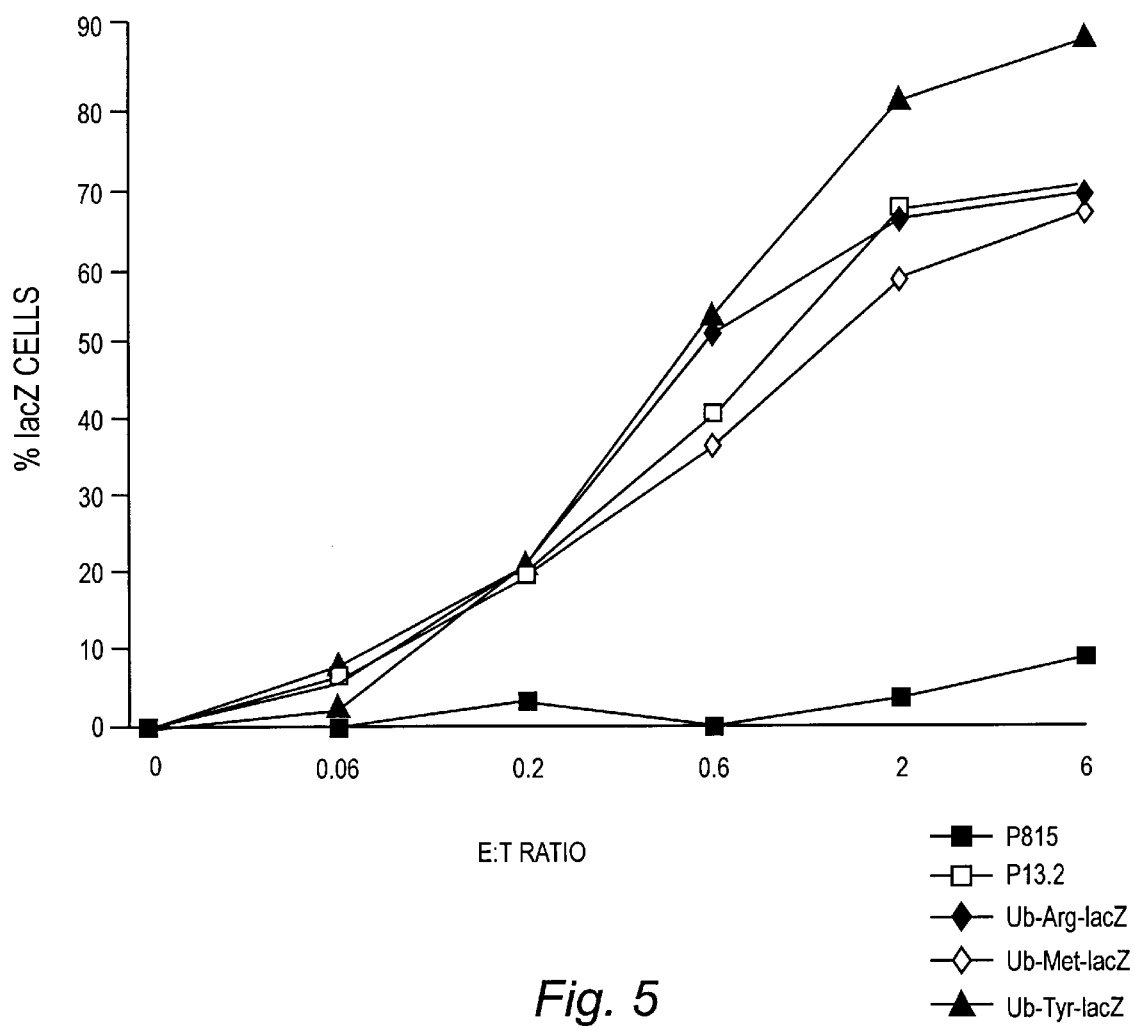
FIG. 5 shows effects of Ub-X-β gal protein degradation on antigen presentation. E:T ratio is on the x-axis. On the y-axis is shown % specific lysis.

Three different P815 Ub-X-lacZ transfectants were incubated with 080513, a H-2-$L^d$-restricted β gal specific CTL clone for 4 h at different E:T ratios. 0805B is effector. The target is the P815 Ub-X-lacZ transfectants. The ability of the P815 transfectants to generate peptides that are appropriately presented by MHC class I molecules was determined by measuring their ability to be lysed by 0805B. As shown in FIG. 5, all three Ub-X-lacZ transfectants are sensitive to specific cytolysis to a similar degree as positive control, P13.2, a lacZ transfectant of P815. The fact that transfectants expressing β gal with destabilizing residues Arg and Tyr did not show any detectable β gal protein expression and activity but were presented at a high degree to a CTL clone, indicate that ubiquitin-proteosome-mediated proteolysis is an important pathway of protein degradation leading to MHC class I antigen presentation.

Figure 6:
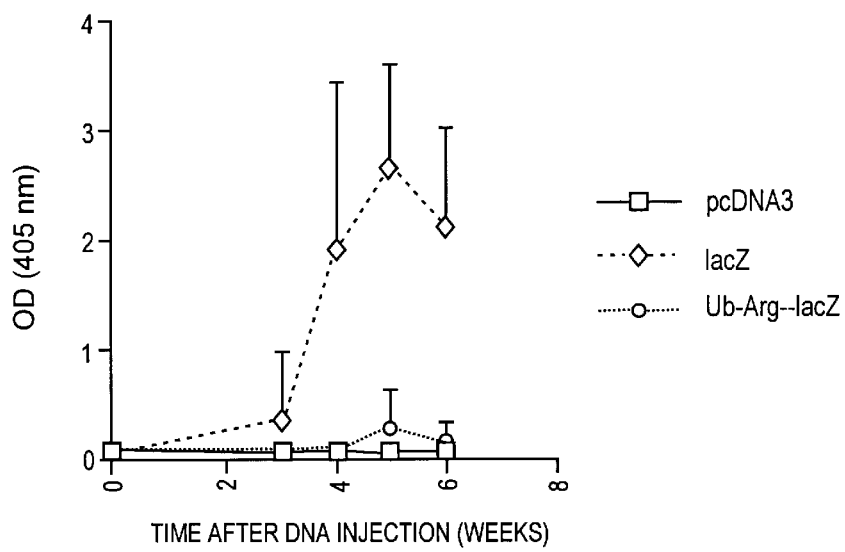
FIG. 6 shows detection of anti-β gal antibodies from mice immunized with different plasmids. Time after DNA injection (weeks) is shown on the x-axis. $OD_{405}$ is shown on the y-axis.

EXAMPLE 4
The Effect of Increased Ub-X-lacZ Degradation on Functional Immunity in vivo The effect of engineering proteins so as to achieve rapid degradation via the ubiquitin processing pathway on antibody response and cytotoxic activity was examined. Mice were immunized with Ub-X-lacZ (X=Arg or Met), lacZ, or pcDNA3. Four BALB/c mice per group were injected intramuscularly with 100 ug of plasmid DNA each week for four weeks. The animals were bled prior to the first injection and then each week starting 3 weeks thereafter. The levels of anti-β gal Ab were detected by ELISA and shown as O.D.+Standard Deviation (Error Bar). Only the mice injected with lacZ have significant Ab production. As shown in FIG. 6, anti-β gal Ab was detected by three weeks after the first injection from mice injected with lacZ. The levels of anti-β gal continuously increased in such mice for another 3 weeks. Injection of Ub-Arg-lacZ did not induce production of detectable anti-β gal Ab. One mouse injected with Ub-Met-lacZ stimulated antibody production significantly (data not shown). This may reflect the differences in the intracellular stability of protein and the need for a larger protein to produce an antibody response.

Figure 7:
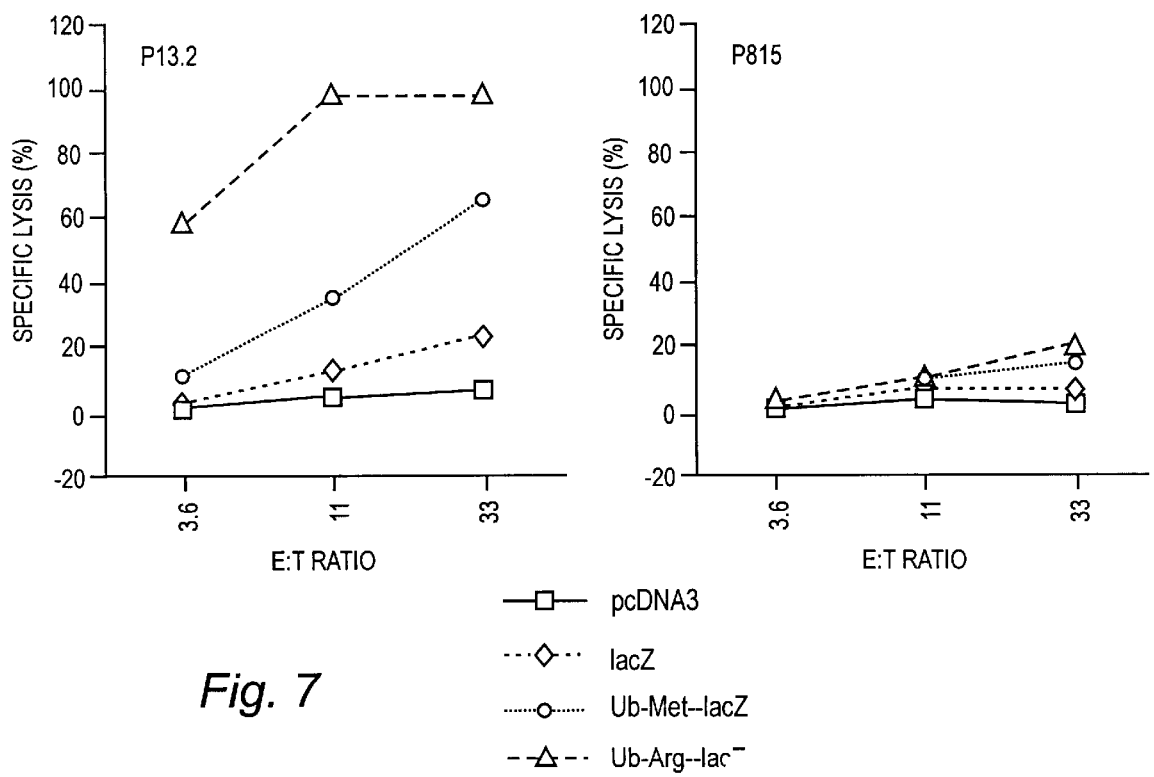
FIG. 7 shows cellular immune responses to β gal in BALB/c mice immunized with various plasmids. E:T ratio is on the x-axis. On the y-axis is shown % specific lysis.

To determine if Ub-X-lacZ gene could induce a specific CTL response, mice were sacrificed 12 weeks after injection. Splenocytes were restimulated in the presence of P13.2, a lacZ transfectant of p815 that presents $H-2^d$-restricted CTL epitopes of the β gal protein. The spleen cells were assayed 7 days later for their ability to lyse the lacZ-expressing target cell-line, P13.2, or P815, the lacZ negative parental cell line. Ub-Arg-lacZ induced much stronger specific CTL than both Ub-Met-lacZ or lacZ (FIG. 7).

This indicates that the Ub-Arg-lacZ construct is not only able to specifically generate a cellular immune response, but that this immune response is significantly greater than that induced by lacZ constructs with greater intracellular stability.

EXAMPLE 5
Her-2

Over-expression of proto-oncogenes can lead to neoplastic transformation. The neu oncogene originally was identified by its ability to transform NIH 3T3 cells in vitro (Padhy, L. C., et al. *Cell* 28:865–871, 1982). Subsequently, neu was found to be highly homologous to a gene on human chromosome 17 (17q21), designated erbB-2 (HER-2/neu) (Schechter, A. L., et al. *Science* 229:976–978, 1985), which is a cell surface growth factor receptor. ErbB-2 is over-expressed in 15–40% of all human breast cancers (Slamon, D. J., et al. *Science* 235:177–182, 1987; van de Vijver, M. J., et al. *N. Engl. J. Med.* 319:1239–1245, 1988; Kraus, M. H., et al. *EMBO J.* 6:605:619, 1987; King, C. R., et al. *Cancer Res.* 49:4185–4191, 1989). This association may define a causal relationship as indicated by studies on mice transgenic for the activated or wild-type neu proto-oncogene under the control of the mouse mammary tumor virus (MMTV) promoter. Transgenic mice expressing activated-neu develop multiple mammary tumors at an early age (Muller, W. J., et al. *Cell* 54:105–115, 1988; Bouchard, L., et al. *Cell* 57:931–936, 1989). Moreover, transgenic mice with the wild-type neu gene under the MMTV promoter also develop focal mammary tumors, albeit with slower kinetics (Guy, C. T., et al. *Proc. Natl. Acad. Sci USA* 89:10578–10582, 1992). The relative selectivity of erbB-2 overexpression in human adenocarcinomas and the association of erbB-2 and neu with a pathogenic mechanism responsible for neoplasia, make the protein product of these genes an attractive target for immunotherapy (Fendly, B. M., et al. *J. Biol. Response Mod.* 9:449–455, 1990; Fendly, B. M., et al. *Vaccine Res.* 2:129–139, 1993).

Figure 8:
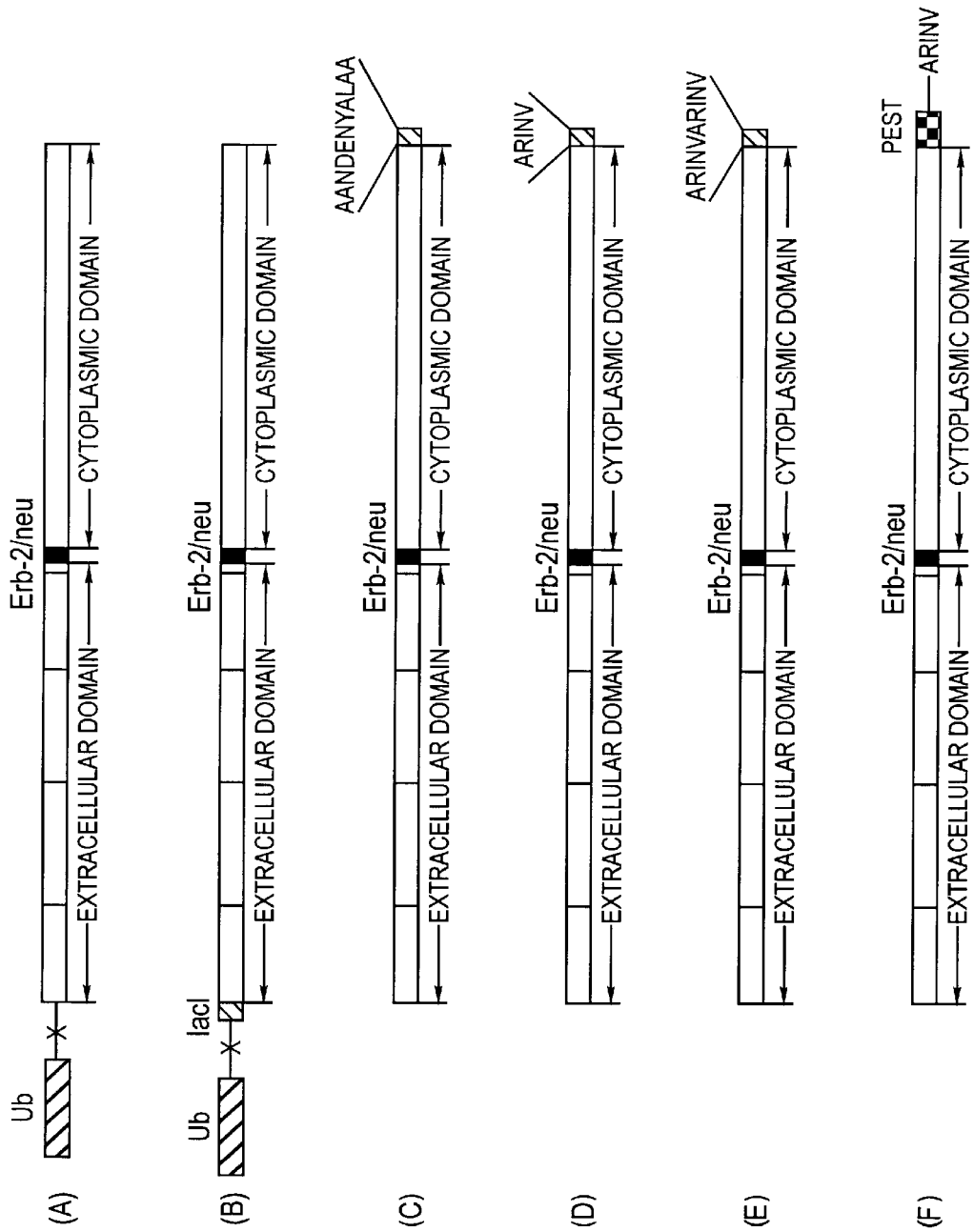
FIGS. 8(A–F) show a diagramatic representations of a chimeric genes encoding different protein processing signals affixed to ErbB-2/Neu (Peoples, G. E., et al. *Proc. Natl. Acad. Sci. U.S.A.* 92:432–436, 1995; Fisk, B. et al. *J. Exp. Med.* 181:2109–2117, 1995).

Depicted in FIG. 8 are constructs of the proto-oncogene product of ErbB-2/neu that are engineered to have enhanced rates of intracellular proteolysis. One or a combination of the various motifs may be used to optimize the ability of genes encoding the chimeric protein to induce a cellular immune response when injected into somatic cells of the animal. Construct (A) (FIG. 8A) has the ubiquitin (Ub) encoded by the 5' end of the gene. X is for the desired intervening amino acid (e.g. Arg) that will become the amino terminus after removal of the ubiquitin moiety. This construct relies on internal ubiquitin acceptor site(s) within the target antigen (e.g. in this case erbB-2/neu) for subsequent poly-ubiquination. Construct (B) (FIG. 8B) has an ubiquitin acceptor sequence of the lacI region interposed between the Ub-X and the target antigen (e.g. erbB-2/neu). Construct (C) (FIG. 8C) encodes the target antigen with an altered carboxy-terminus containing one or more "AANDENYA-LAA (SEQ ID NO: 33)" motifs. Construct (D) (FIG. 8D) encodes the target antigen with an altered carboxy terminus containing a "ARINV (SEQ ID NO: 32)" motif. Construct (E) encodes the target antigen with an altered carboxy terminus containing two or more "ARINV (SEQ ID NO: 32)" motifs. Construct (F) (FIG. 8F) encodes the target antigen with an altered carboxy terminus containing one or more "PEST" domains and one or more "ARINV (SEQ ID NO: 32)" motifs.

These constructs are useful for the generation of a CTL response specific to the neu protein expressed on tumor cells. Immunotherapy would entail injection of such constructs into patients having tumor cells over-expressing neu on their cell surface.

Other embodiments are within the claims.

What is claimed is:

1. A pharmaceutical composition for generating in a patient an MHC-I-mediated cellular immune response to a target antigen(s) comprising a vector comprising a nucleotide sequence encoding a chimeric immunogen, wherein said chimeric immunogen comprises a) a ubiquitin molecule,
   b) an intervening amino acid, selected from the group consisting of arginine and tyrosine, positioned at the carboxy terminal end of the ubiquitin molecule, and
   c) a target antigen, or portion thereof, positioned at the carboxy terminal end of said intervening amino acid, wherein said target antigen is selected from the group consisting of gp100, MART-1, tyrosinase, MAGE-1, MAGE-2, MAGE-3, MAGE-3b, MAGE-4, MAGE-4a, MAGE-4b, MAGE-5a, MAGE-5b, MAGE-6, MAGE-8, MAGE-9, MAGE-10, MAGE-11, MAGE-41, MAGE-Xp, BAGE, N-acetylglucosaminyltransferase-V Intron, p15, MUM-1, MUM-1b, MUM-1c, ErbB-2 (Her-2/neu), CDK4, Human papillomavirus, Human papillomavirus-E6, Human papillomavirus-E7, and Prostate Specific Antigen (PSA).

2. The pharmaceutical composition of claim 1, wherein said chimeric immunogen further comprises a ubiquitin acceptor molecule that is not the target antigen, wherein said ubiquitin acceptor molecule is positioned at the carboxy terminal end of said intervening amino acid.

3. Method for generating in a patient an MHC-I-mediated cellular immune response to a target antigen(s) comprising the step of:

introducing into the cells of said patient a vector comprising a nucleotide sequence encoding a chimeric immunogen, wherein said chimeric immunogen comprises a) a ubiquitin molecule,
   b) an intervening amino acid, selected from the group consisting of arginine and tyrosine, positioned at the carboxy terminal end of the ubiquitin molecule, and
   c) a target antigen, or portion thereof, positioned at the carboxy terminal end of said intervening amino acid, wherein said target antigen is selected from the group consisting of gp100, MART-1, tyrosinase, MAGE-1, MAGE-2, MAGE-3, MAGE-3b, MAGE-4, MAGE-4a, MAGE-4b, MAGE-5a, MAGE-5b, MAGE-6, MAGE-8, MAGE-9, MAGE-10, MAGE-11, MAGE-41, MAGE-Xp, BAGE, N-acetylglucosaminyltransferase-V Intron, p15, MUM-1, MUM-1b, MUM-1c, ErbB-2 (Her-2/neu), CDK4, Human papillomavirus, Human papillomavirus-E6, Human papillomavirus-E7, and Prostate Specific Antigen (PSA), wherein said chimeric immunogen is made within said cells, and said chimeric immunogen is subsequently processed by the proteosome pathway for presentation of said target antigen(s) to said patient's immune system to generate an MHC-I-mediated cellular immune response in said patient.

4. The method of claim 3, wherein said target antigen comprises greater than 25 amino acid residues.

5. The method of claim 3, wherein said target antigen is derived from the ErbB-2 gene product.

6. The method of claim 3, wherein said chimeric immunogen further comprises a ubiquitin acceptor molecule that is not the target antigen, wherein said ubiquitin acceptor molecule is positioned at the carboxy terminal end of said intervening amino acid.

7. The method of claim 6, wherein said ubiquitin acceptable molecule is lac I or Sindbis virus RNA polymerase.

* * * * *